(12) United States Patent
Baker, Jr. et al.

(10) Patent No.: US 6,506,803 B1
(45) Date of Patent: Jan. 14, 2003

(54) METHODS OF PREVENTING AND TREATING MICROBIAL INFECTIONS

(75) Inventors: James R. Baker, Jr., Ann Arbor, MI (US); Tarek Hamouda, Ypsilanti, MI (US); Amy Shih, Ann Arbor, MI (US); Andrzej Myc, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/561,111

(22) Filed: Apr. 28, 2000

Related U.S. Application Data

(63) Continuation-in-part of application No. 09/474,866, filed on Dec. 30, 1999.
(60) Provisional application No. 60/131,638, filed on Apr. 28, 1999.

(51) Int. Cl.$^7$ ............................................... A01N 25/00
(52) U.S. Cl. ....................................... 514/937; 514/938
(58) Field of Search ................................ 424/93.1, 450, 424/234.1, 78.17, 489; 514/546, 937, 938

(56) References Cited

U.S. PATENT DOCUMENTS

| | | | |
|---|---|---|---|
| 4,451,267 A | * 5/1984 | Schwab et al. ................. | 44/53 |
| 4,599,088 A | * 7/1986 | Davis et al. .................... | 44/51 |
| 4,895,452 A | 1/1990 | Yiournas et al. ............. | 366/173 |
| 5,103,497 A | 4/1992 | Hicks ......................... | 385/117 |
| 5,108,660 A | 4/1992 | Michael ...................... | 252/545 |
| 5,368,837 A | 11/1994 | Baker et al. ................... | 424/5 |
| 5,510,104 A | 4/1996 | Allen ......................... | 424/94.4 |
| 5,547,677 A | 8/1996 | Wright ........................ | 424/401 |
| 5,549,901 A | 8/1996 | Wright ........................ | 424/401 |
| 5,618,840 A | 4/1997 | Wright ........................ | 514/549 |
| 5,662,957 A | 9/1997 | Wright ........................ | 426/605 |
| 5,700,679 A | 12/1997 | Wright ........................ | 435/238 |
| 5,709,879 A | 1/1998 | Barchfeld et al. ........... | 424/450 |
| 5,961,970 A | 10/1999 | Lowell et al. ............. | 424/93.1 |
| 5,985,309 A | * 11/1999 | Edwards et al. ............. | 424/426 |
| 6,015,832 A | * 1/2000 | Baker, Jr. et al. ........... | 514/546 |
| 6,348,187 B1 | 2/2002 | Pan et al. ..................... | 424/53 |
| 6,361,787 B1 | 3/2002 | Shaheen et al. ............. | 424/406 |

OTHER PUBLICATIONS

Hamouda et al., Microbicidal Effects of Lipsome–Like Nanoemulsion on Pathogenic Gram Negative Bacteria, *98th ASM General Meeting*, Atlanta, Abstract # A–52 p. 47 (11 pages).

Alasri et al., "Sporicidal properties of peracetic acid and hydrogen peroxide, alone and in combination, in comparison with chlorine and formaldehyde for ultrafiltration membrane disinfection." *Can. J. Microbiol* 1993; 39: 52–60.

Barrett and Inglis "Growth purification and titration of influenza viruses." In: Mahy WJ. ed. Virology. a Practical approach. IRL. Press, 1985; 119–151. This reference is a book and is not being submitted at this time but if the Examiner requests the reference it will be submitted.

Baragi et al., "Transplantation of transdiced Chondrocytes protects articular cartilage from intedeukin 1 –induced extracellular matrix degradation." *J Clin Invest* 1995;96: 2454–2460.

Beauchamp et al., "A Critical review of the toxicology of glutaraldphyde." *Crit. Rev. ToxicoL* 1992; 22:143–174.

(List continued on next page.)

*Primary Examiner*—Thurman K. Page
*Assistant Examiner*—Blessing Fubara
(74) *Attorney, Agent, or Firm*—Medlen & Carroll, LLP

(57) ABSTRACT

The present invention provides methods and compositions for inactivating bacteria including bacterial spores using an oil-in-water emulsion are provided. The oil-in-water emulsion comprises an oil, a surfactant and an organic phosphate-based solvent. These methods can be used to inactivate a wide variety of microorganisms including bacteria, bacterial spores, fungi, fungal spores and enveloped viruses.

35 Claims, 35 Drawing Sheets

Time Zero

OTHER PUBLICATIONS

Berkelman et al., "Emerging infectious diseases in the United States, 1993." *J Infect Dis.* Aug. 1994; 170(2):272–7.

Burdon et al., "Experimental infection of mice with Bacillus cereus: studies of pathogenesis and pathologic changes." *J. Infect. Dis.* 1967; 117:307–316.

Burdon and Wende. "On the differentiation of anthrax bacilli from *Bacillus cereus.*" *J. Infect. Dis.* 1960; 107: 224–234.

Chatlyyne et al., "A lipid emulsion with effective virucidal activity against HIV–1 and other common viruses." *Foundation for Retrovirology and Human Health*, 3rd Conference on Retroviruses and Opportunistic Infections, Washington D.C., U.S.A., 1996; Abstract #351. This reference is a book and is not being submitted at this time but if the Examiner requests the reference it will be submitted.

Dragon and Rennie "The ecology and anthrax spores: Tough but not invincible." *Can. Vet. J.* 1995; 36: 295–301.

Drobniewski "*Bacillus cereus* and related species." *Clin. Microbiol. Rev.* 1993; 6: 324–338.

Eriksson et al., "Virus validation of plasma–derived products produced by Pharmacia, with particular reference to immuno Globulins." *Blood Coagulation and Fibtinolysis 1994*; 5 (Suppl. 3): S37–S44. This reference is a book and is not being submitted at this time but if the Examiner requests the reference it will be submitted.

Florence "Non–ionic surfactant vesicles: preparation and characterization." In: Gregoriadis G. ed. Liposome Technology. Liposome Preparations and Related Techniques. 2nd ed. vol. 1. CRC Press, 1993. This reference is a book and is not being submitted at this time but if the Examiner requests the reference it will be submitted.

Foster and Johnstone "Pulling the trigger: the mechanism of bacterial spore germination." *MolecularMicrobiology* 1990;4:137–141.

Franz et al., "Clinical recognition and management of patients exposed to biological warfare agents." *JAMA* 1997; 278: 399–411.

Fritz et al., "Pathology of experimental anthrax in'the rhesus monkey." *Lab.* Invest. 1995; 73: 691–702.

Goodman & Gilman's "The Pharmacological Basis of Therapeutics" Eds. Hardman et al., 9th Edition, Pubi. McGraw Hill, 1996; chapters 43 through 50. This reference is a book and is not being submitted at this time but if the Examiner requests the reference it will be submitted.

Graham et al., "Characteristics of a human cell line transformed by DNA from human adenovirus type 5." *J Gen Virol* 1977; 36: 59–74.

Halvorson and Church, Bacteriol Rev 1957, 21:112.

Hamouda et al., "Microbiocidal effects of liposome–like microemulsions on pathogenic Gram negative bacteria." In: American Society for *Microbiology*, 98th General Meeting, Atlanta, Georgia, U.S.A., 1998; Abstract A–52. This reference is a book and is not being submitted at this time but if the Examiner requests the reference it will be submitted.

Hamouda et al., "A novel surfactant nanoemulsion with broad–spectrum sporicidal activity against Bacillus species". Journal Infectious Disease 1999. 180:1939–1949.

Hayden et al., "Plaque inhibition assay for drug susceptibility testing of influenza viruses." *Antimicrob Agents* Chemother. 1980 17: 865–870.

Herlocher et al., "Sequence comparison of AIAA/6/60 influenza viruses: mutations, which may contribute to attenuation." *Virus Res.* 1996; 42:11–25.

Hermonat et al., "The spermicide nonoxynol–9 does not inactivate papillomavirus." *Sexually Trans Dis* 1992; 19: 203–205.

Hess et al., "Epidermal toxicity of disinfectants." *Amer. J. Dent.* 1991; 4: 51–56.

Hills, *J Gen Microbiol* 4:38,1950.

Horowitz et al., "Solvent/detergent–treated plasma: a virus–in activated substitute for fresh frozen plasma." *Blood* 1992; 79: 826–831.

Huang et al., "Antiviral activity of some natural and synthetic sugar analogues." *FEBS* Letters. 1991; 291: 199–202.

Ivins et al., "Experimental anthrax vaccines: efficacy of adjuvants combined with protective antigen against an aerosol *Bacillus anthracis* spore challenge in guinea pigs." *Vaccine* 1995; 13: 1779–1784.

Jackson et al., "PCR analysis of tissue samples from the 1979 Sverdlovsk anthrax victims: The presence of multiple *Bacillus anthracis* strains in 10 different victims." *PNAS* 1998; 95:1224–1229.

Karalvanova and Spiro RG. "Sulphation of N–linked oligosacchaddes of vesicular stomatitis and influenza virus envelope glycoproteins: host cell specificity, subcellular localization and identification of substituted saccharides." *Bioch J* 1998; 329: 511–518.

Lamanna and Jones "Lethality for mice of vegetative and spore forms of *Bacillus cereus* and *Bacillus cereus*–like insect pathogens injected intraperitoneally and subcutaneously." *J. Bact.* 1963; 85: 532–535.

Lamb and Krug "Orthomyxoviride: The viruses and their replication." In: Fields BN. Knipe DM. Howley PM. eds. Fields Virology, 3rd ed., Philadelphia Pennsylvania, U.S.A., Lippincoft–Raven Publishers, 1996; 1353–1395.

Lee "Review: in vitro spermicidal tests." *Contraception* 1996; 54: 131–147.

Lim and Chae "A simple assay for DNA transfection by incubation of the cells in culture dishes with substrates for beta–galactosidase." *Biotechniques* 1989; 7: 576–579.

Lineaweaver et al., "Topical antimicrobial toxicity." *Arch. Surg.* 1985; 120: 267–270.

Maha and Igarashi "The effect of nonionic detergent on dengue and Japanese encephalitis virus antigens in antigen detection ELISA and IgM–capture ELISA." *Southeast Asian J Trop Med Pub Health* 1997; 28: 718–722. This reference is a book and is not being submitted at this time but if the Examiner requests it will be submitted.

Mammen et al., "Effective inhibitors of hemagglutination by influenza virus synthesized from polymers having active ester groups. Insight into mechanism of inhibition." *J Med Chem* 1995; 38: 4179–4190.

Mendel et al., "Oral administration of a prodrug of the influenza virus neuraminidase inhibitor GS 4071 protects mice and ferrets against influenza infection." *Antimicrob Agents Chemother* 1998; 42: 640–646.

Meselson et al., "The Sverdlovsk anthrax outbreak of 1979." *Science* 1994; 266:1202–1208.

Mobley "Biological warfare in the twentieth century: lessons from the past, challenges for the future." *Military Med.* 1995; 160: 547–553.

Morgan "A brief review of formaldehyde carcinogenesis in relation to rat nasal pathology and human health risk assessment." *ToxicoL PathoL* 1997; 25: 291–307.

Mosmann J. Immun. *Methods 1983*, 65, 55–63 Mulder and Hers "Influenza." Wolter–Noordhoff Publishing, 1972.

O'Hagan "Recent advances in vaccine adjuvants for systemic and mucosal administration." *J Pharmacy Pharmacol* 1998; 50: 1–10.

Pile et al., "Anthrax as a potential biological weapon." *Arch. Intem. Med.* 1998; 158: 429–434.

Portocala et al., "Immunoelectrophoretic characterization of Sendai virus antigens." *Virologie* 1976; 27: 261–264.

Russell "Bacterial spores and chemical sporicidal agents." *Clin. Micro* 1990; 3: 99–119.

Schulze "Effects of glycolysation on the properties and functions of influenza virus hemagglutinin." *J Infect Dis* 1997; 176 (Suppl. 1): S24–28.

Shibata "Germination of inactivated spores of *Bacillus cereus* T. Effect of preincubation with L–alanine or inosine on the subsequent germination." *Japan. J. Microbiol.* 1976; 20: 529–535.

Smith et al., "Dihydropyrancarboxamides related to Zanamivir: a new series of inhibitors of influenza virus sialidases. 1. Discovery, synthesis biological activity, and structure–activity relationships of 4–guanidino and 4–amino–4H–pyran–6–carboxamides." *J Med Chem* 1998; 41: 787–797.

Titball and Manchee "Factors affecting the germination of spores of *Bacillus anthracis*." *J. Appi. Bact.* 1987; 62: 269–273.

Waghorn and Goa, "Zanamivir." *Drugs* 1998; 55: 721–725.

Welkos and Friedlander "Pathogenesis and genetic control of resistance to the Steme strain of *Bacillus anthracis.*" *Microb. Path.* 1988; 4: 53–69.

Welkos et al., "Differences in susceptibility of inbred mice to *Bacillus anthracis*" *Infect. Immun.* 1986; 51: 795–800.

Yanagita, 1957, *Arch Mikrobiol* 26:329.

Zeitlin et al., "Tests of vaginal microbicides in the mouse genital herpes model." *Contraception* 1997; 56: 329–335.

* cited by examiner

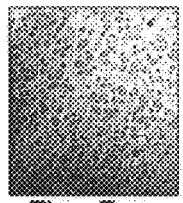
FIG. 2A
Time Zero
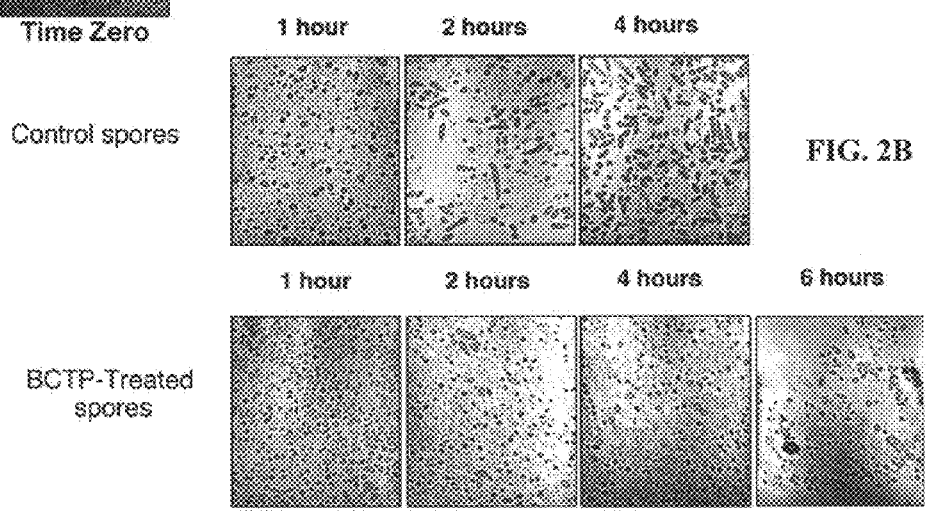
FIG. 2B
FIG. 2C

% Sporicidal activity in 4 hours at room temp.

% Sporicidal activity in 4 hours at room temp.

Effect of BCTP, P10 and BCTP401 on influenza A infectivity

| MICROBE | |
|---|---|
| Bacteria | *Bacillus* (including *B. cereus, B. anthracis, B. circulans B. subtilis,* and *B. megaterium);*<br>*Clostridium* (including *C. botulinum, C. tetani,* and *C. perfringens);*<br>*E. coli;*<br>*Haemophilus* (including *H. influenzae);*<br>*Listeria monocytogenes;*<br>*Neisseria* (including *N. gonorrhoeae);*<br>*Proteus* (including *P. mirabilis);*<br>*Psuedomonas* (including *P. aeruginosa);*<br>*Shigella* (including *S. dysenteriae);*<br>*Salmonella* (including *S. typhimurium);*<br>*Staphlococcus (including S. aureus)*<br>*Streptococcus* (including *S. agalactiae, S. pneumonia, S. pyogenes);*<br>*Vibrio* (including *V. cholerae* classical and Eltor); and<br>*Yersinea* (including *Y. enterocolitica and Y. pseudotuberculosis);* and |
| Enveloped virus | Influenza (including A, B and C);<br>Herpes (including H. simplex);<br>Sendai;<br>Sindbis; and<br>Pox virus (including vaccinia) |
| Fungi | *Candida* (including *C. albicans* and *C. tropicalis);*<br>Trichophyton (including T. rubrum and T. mentagrophytes);<br>Microsporum gypseum;<br>Byussochlymus fulva |

FIG. 29A

| Emulsion Formulas | | Result |
|---|---|---|
| ATB-X100 | | Effective against enveloped viruses, all Gram positive bacteria, all Gram negative bacteria and fungi |
| 8% | Triton X-100 | |
| 8% | Tributyl Phosphate | |
| 64% | Soybean Oil | |
| 1% | CPC | |
| 19% | DiH2O | |
| ATB-T60 | | Slightly less effective than ATB-X100; Effective against enveloped viruses, all Gram positive bacteria, all Gram negative bacteria and fungi |
| 5% | Tween 60 | |
| 8% | Tributyl Phosphate | |
| 64% | Soybean Oil | |
| 1% | CPC | |
| 22% | DiH2O | |
| ATB-XT160 | | Effective against enveloped viruses, all Gram positive bacteria, all Gram negative bacteria and fungi |
| 0.71% | Tween 60 | |
| 8% | Triton X-100 | |
| 8% | Tributyl Phosphate | |
| 64% | Soybean Oil | |
| 1% | CPC | |
| 18.29% | DiH2O | |
| ATB-X | | Effective against enveloped viruses, all Gram positive bacteria, all Gram negative bacteria and fungi; |
| 5% | Triton X-100 | |
| 5% | Tributyl Phosphate | |
| 40% | Soybean Oil | |
| 1% | CPC | |
| 49% | DiH2O | |
| ATB-X1001 | | Effective against enveloped viruses, all Gram positive bacteria, all Gram negative bacteria and fungi |
| 8% | Triton X-100 | |
| 8% | Tributyl Phosphate | |
| 50% | Soybean Oil | |
| 1% | CPC | |
| 33% | DiH2O | |

FIG. 29B

| Emulsion Formulas | | Result |
|---|---|---|
| ATB-X1002 | | Effective against enveloped viruses, all Gram positive bacteria, all Gram negative bacteria and fungi; more irritating than ATB-X100. |
| 8% | Triton X-100 | |
| 8% | Tributyl Phosphate | |
| 50% | Soybean Oil | |
| 2% | CPC | |
| 32% | DiH2O | |
| ATB-2 | | Effective against enveloped viruses, all Gram positive bacteria, all Gram negative bacteria and fungi |
| 0.1% | Peppermint Oil | |
| 8% | Triton X-100 | |
| 8% | Tributyl Phosphate | |
| 64% | Soybean Oil | |
| 2% | CPC | |
| 17.9% | DiH2O | |
| ATB-CPB | | Effective against enveloped viruses, all Gram positive bacteria, all Gram negative bacteria. |
| 0.1% | Peppermint Oil | |
| 8% | Triton X-100 | |
| 8% | Tributyl Phosphate | |
| 64% | Soybean Oil | |
| 1% | CPB | |
| 18.9% | DiH2O | |
| ATB-1/2 | | Effective against enveloped viruses, all Gram positive bacteria, all Gram negative bacteria and fungi, demonstrates that dilution doesn't effective efficacy of ATB-X100 |
| 0.05% | Peppermint Oil | |
| 4% | Triton X-100 | |
| 4% | Tributyl Phosphate | |
| 32% | Soybean Oil | |
| 0.5% | CPC | |
| 59.45% | DiH2O | |
| ATB-T3 | | Effective against enveloped viruses, all Gram positive bacteria, all Gram negative bacteria and fungi |
| 3% | Tyloxapol | |
| 8% | Tributyl Phosphate | |
| 64% | Soybean Oil | |
| 1% | CPC | |
| 0.1% | Peppermint Oil | |
| 23.9% | DiH2O | |

FIG. 29C

| Emulsion Formulas | | Result |
|---|---|---|
| ATB-T3E pH7.1 | | Effective against, all Gram positive bacteria, all Gram negative bacteria and spores. |
| 3% | Tyloxapol | |
| 8% | Ethanol | |
| 64% | Soybean Oil | |
| 1% | CPC | |
| 0.1% | Peppermint Oil | |
| 23.8% | DiH2O | |
| 0.1% | 10N NaOH | |
| | | |
| ATB-T22 | | Effective against enveloped viruses, all Gram positive bacteria, all Gram negative bacteria and fungi; stable despite lower amount of detergent |
| 2% | Triton X-100 | |
| 2% | Tyloxapol | |
| 8% | Tributyl Phosphate | |
| 64% | Soybean Oil | |
| 1% | CPC | |
| 0.1% | Peppermint Oil | |
| 22.9% | DiH2O | |
| | | |
| ATB-1X | | Effective against enveloped viruses, all Gram positive bacteria, all Gram negative bacteria, and bacterial spores |
| 8% | Triton X-100 | |
| 8% | Tributyl Phosphate | |
| 64% | Soybean Oil | |
| 1% | CPC | |
| 0.1% | Peppermint Oil | |
| 5 mM | Inosine | |
| 5 mM | L-Alanine | |
| 10 mM | Ammonium Chloride | |
| 1 mM | Sodium Phosphate | |
| 13 mM | Sodium Chloride | |
| 18.9% | DiH2O | |

FIG. 29D

| Emulsion Formulas | | Result |
|---|---|---|
| ATB-T22/GE | | Effective against enveloped viruses, all Gram positive bacteria, Gram negative bacteria, and bacterial spores |
| 2% | Triton X-100 | |
| 2% | Tyloxapol | |
| 8% | Tributyl Phosphate | |
| 64% | Soybean Oil | |
| 1% | CPC | |
| 0.1% | Peppermint Oil | |
| 5 mM | Inosine | |
| 5 mM | L-Alanine | |
| 10 mM | Ammonium Chloride | |
| 1 mM | Sodium Phosphate | |
| 13 mM | Sodium Chloride | |
| 22.9% | DiH2O | |
| 90% ATB-T22/GE | | Effective against enveloped viruses, Gram negative bacteria, all Gram positive bacteria, and bacterial spores; liquid enough to spray |
| 1.8% | Triton X-100 | |
| 1.8% | Tyloxapol | |
| 7.2% | Tributyl Phosphate | |
| 57.6% | Soybean Oil | |
| 0.9% | CPC | |
| 0.09% | Peppermint Oil | |
| 5 mM | Inosine | |
| 5 mM | L-Alanine | |
| 10 mM | Ammonium Chloride | |
| 1 mM | Sodium Phosphate | |
| 13 mM | Sodium Chloride | |
| 30.61% | DiH2O | |
| ATB-T22E | | Effective against enveloped viruses, all Gram positive bacteria, all Gram negative bacteria and fungi; Increased safety for oral uptake |
| 2% | Triton X-100 | |
| 2% | Tyloxapol | |
| 8% | Ethanol (200 Proof) | |
| 64% | Soybean Oil | |
| 1% | CPC | |
| 0.1% | Peppermint Oil | |
| 22.9% | DiH2O | |

FIG. 29E

| Emulsion Formulas | | Result |
|---|---|---|
| 90% ATB-T22E/GE | | Effective against enveloped viruses, all Gram positive bacteria, all Gram negative bacteria and fungi; Increased safety for oral uptake |
| 1.8% | Triton X-100 | |
| 1.8% | Tyloxapol | |
| 7.2% | Ethanol (200 Proof) | |
| 57.6% | Soybean Oil | |
| 0.9% | CPC | |
| 0.09% | Peppermint Oil | |
| 5 mM | Inosine | |
| 5 mM | L-Alanine | |
| 10 mM | Ammonium Chloride | |
| 1 mM | Sodium Phosphate | |
| 13 mM | Sodium Chloride | |
| 30.61% | DiH2O | |
| | | |
| ATB-T3E | | Effective against all Gram positive bacteria, all Gram negative bacteria; Increased safety for oral uptake |
| 3% | Tyloxapol | |
| 8% | Ethanol | |
| 64% | Soybean Oil | |
| 1% | CPC | |
| 0.1% | Peppermint Oil | |
| 23.9% | DiH2O | |
| | | |
| ATB-X100E | | |
| 8% | Triton X-100 | |
| 8% | Ethanol | |
| 64% | Soybean Oil | |
| 1% | CPC | |
| 19% | DiH2O | |
| | | |
| ATB_Tween 20 E | | Effective against all Gram negative bacteria. |
| 5% | Tween 20 | |
| 1% | CPC | |
| 64% | Soybean Oil | |
| 8% | Ethanol | |
| 22% | DiH2O | |

METHODS OF PREVENTING AND TREATING MICROBIAL INFECTIONS

The following application is a Continuation-in-Part of U.S. application Ser. No. 09/474,866, filed Dec. 30, 1999, pending, which is hereby incorporated herein by reference in its entirety; this application also claims priority to U.S. provisional application No. 60/131,638, filed Apr. 28, 1999.

This invention was made in part during work partially supported by the U.S. government under DARPA grant No. MDA972-97-1-0007. The government has certain rights in the invention.

FIELD OF THE INVENTION

The present invention relates to compositions and methods for decreasing the infectivity, morbidity, and rate of mortality associated with a variety of pathogenic organisms. The present invention also relates to methods and compositions for decontaminating areas colonized or otherwise infected by pathogenic organisms. Moreover, the present invention relates to methods and compositions for decreasing the infectivity of pathogenic organisms in foodstuffs. In particular, decreased pathogenic organism infectivity, morbidity, and mortality is accomplished by contacting the pathogenic organism with an oil-in-water nanoemulsion comprising an oil, an organic solvent, and a surfactant dispersed in an aqueous phase.

BACKGROUND OF THE INVENTION

Pathogens such as bacteria, fungi, viruses and bacterial spores are responsible for a plethora of human and animal ills. The first step in microbial infections is generally attachment or colonization of skin or mucus membranes, followed by subsequent invasion and dissemination of the infectious microbe. The portals of entry of pathogenic bacteria are predominantly the skin and mucus membranes.

In particular, bacteria of the Bacillus genus form stable spores that resist harsh conditions and extreme temperatures. Contamination of farmlands with *B. anthracis* leads to a fatal disease in domestic, agricultural, and wild animals (Dragon and Rennie, 1995). Human infection with this organism usually results from contact with infected animals or infected animal products (Welkos et al., 1986). Human clinical syndromes include a pulmonary form that has a rapid onset and is frequently fatal. The gastrointestinal and cutaneous forms of anthrax, although less rapid, can result in fatalities unless treated aggressively (Franz et al., 1997; Pile et al., 1998). *Bacillus anthracis* infection in humans is no longer common due to effective animal controls that include vaccines, antibiotics and appropriate disposal of infected livestock. However, animal anthrax infection still represents a significant problem due to the difficulty in decontamination of land and farms.

While an anthrax vaccine is available (Ivins et al., 1995) and can be used for the prevention of classic anthrax, genetic mixing of different strains can render it ineffective (Mobley, 1995). The potential consequences of the use of Anthrax spores as a biological weapon was demonstrated by the accidental release of *Bacillus anthracis* from a military microbiology laboratory in the former Soviet Union. Seventy-seven cases of human anthrax, including 66 deaths, were attributed to the accident. Some anthrax infections occurred as far as 4 kilometers from the laboratory (Meselson et al., 1994). Genetic analysis of infected victims revealed the presence of either multiple strains or a genetically altered *B. anthracis* (Jackson et al, 1998).

Other members of the Bacillus genus are also reported to be etiological agents for many human diseases. *Bacillus cereus* is a common pathogen. It is involved in food borne diseases due to the ability of the spores to survive cooking procedures. It is also associated with local sepsis, wound and systemic infection (Drobniewski, 1993). Many bacteria readily develop resistance to antibiotics. An organism infected with an antibiotic resistant strain of bacteria faces serious and potentially life-threatening consequences.

Examples of bacteria that develop resistance include staphylococcus which often cause fatal infections, pneumococci that cause pneumonia and meningitis; Salmonella and *E. coli* that cause diarrhea; and enterococci that cause blood-stream, surgical wound and urinary tract infections (Berkelman et. al., 1994).

Although an invaluable advance, antibiotic and antimicrobial therapy suffers from several problems, particularly when strains of various bacteria appear that are resistant to antibiotics. In addition, disinfectants/biocides (e.g., sodium hypochlorite, formaldehyde and phenols) which are highly effective against Bacillus spores, are not well suited for decontamination of the environment, equipment, or casualties. This is due to toxicity that leads to tissue necrosis and severe pulmonary injury following inhalation of volatile fumes. The corrosive nature of these compounds also renders them unsuitable for decontamination of sensitive equipment (Alasfl et al. 1993; Beauchamp et al., 1992; Hess et al., 1991; Lineaweaver et al. 1985; Morgan, 1997; Russell, 1990).

Influenza A virus is a common respirator pathogen that is widely used as a model system to test anti-viral agents in vitro (Karaivanova and Spiro, 1998; Mammen et al., 1995; Huang et al. 1991) and in vivo (Waghorn and Goa, 1998; Mendel et al. 1998; Smith et al. 1998). The envelope glycoproteins, hemagglutinin (HA) and neuraminidase (NA), which determine the antigenic specificity of viral subtypes, are able to readily mutate, allowing the virus to evade neutralizing antibodies. Current anti-viral compounds and neuraminidase inhibitors are minimally effective and viral resistance is common (Lamb and Krug, 1996; Schulze, 1997).

Clearly, antipathogenic compositions and methods that decrease the infectivity, morbidity, and mortality associated with pathogenic exposure are needed. Such compositions and methods should preferably not have the undesirable properties of promoting microbial resistance, or of being toxic to the recipient.

DESCRIPTION OF THE FIGURES

The following figures form part of the present specification and are included to further demonstrate certain aspects and embodiments of the present invention. The invention may be better understood by reference to one or more of these figures in combination with the detailed description of specific embodiments presented herein.

FIG. 2A–FIG. 2C illustrate bacterial smears showing the bactericidal efficacy of an emulsion of the present invention on *B. cereus* spores.

FIG. 20A–FIG. 20F depict gross and histologic photographs of animals injected subcutaneously with different combinations of BCTP and *B. cereus* spores. FIG. 20A and FIG. 20B illustrate animals that were injected with BCTP alone at a dilution of 1:10. There was no gross tissue damage and histology showed no inflammation. FIG. 20 C and FIG. 20D illustrate animals that were injected with 4×10$^7$ *Bacillus cereus* spores alone subcutaneously. A large necrotic area resulted with an average area of 1.68 cm$^2$. Histology of this area showed essentially complete tissue necrosis of the epidermis and dermis including subcutaneous fat and muscle. FIG. 20E and FIG. 20F depict mice that were injected with 4×10$^7$ Bacillus spores which had been immediately premixed with the BCTP nanoemulsion at final dilution 1:10. These animals showed minimal skin lesions with average area 0.02 cm$^2$ (an approximate 98% reduction from those lesions resulting from an untreated infection with spores). Histology in FIG. 20F indicates some inflammation, however most of the cellular structures in the epidermis and dermis were intact. All histopathology is shown at 4× magnification.

FIG. 21A and FIG. 21B depict mice with experimental wounds that were infected with 2.5×10$^7$ *Bacillus cereus* spores but not treated. Histological examination of these wounds indicated extensive necrosis and a marked inflammatory response.

FIG. 21C and FIG. 21D depict mice with wounds that were infected with 2.5×10$^7$ *Bacillus cereus* spores and irrigated 1 hour later with saline. By 48 hours, there were large necrotic areas surrounding the wounds with an average area of 4.86 cm$^2$. In addition, 80% of the animals in this group died as a result of the infection. Histology of these lesions indicated total necrosis of the dermis and subdermis and large numbers of vegetative Bacillus organisms.

FIG. 21E and FIG. 21F depict mice with wounds that were infected with 2.5×10$^7$ *Bacillus cereus* spores and irrigated 1 hour later with a 1:10 dilution of BCTP. There were small areas of necrosis adjacent to the wounds (0.06 cm$^2$) which was reduced 98% compared to animals receiving spores and saline irrigation. In addition, only 20% of animals died from these wounds. histology of these lesions showed no evidence of vegetative Bacillus illustrates several particular embodiments the various emulsions of the present invention.

FIG. 22 illustrates the inhibition of influenza A infection by surfactant lipid preparations. FIG. 22B: BCTP and SS. Virus was incubated with SLPs for 30 min. and subsequently diluted and overlaid on cells. Inhibition of influenza A infection was measured using cellular ELISA. Each data point represents the mean of three replicates +/− one standard error.

FIG. 25A illustrates the influenza A virus untreated; FIG. 25B illustrates influenza A virus incubated with BCTP for 15 min; FIG. 25C illustrates the adenovirus untreated; and FIG. 25D illustrates the adenovirus incubated with BCTP for 60 min. For all images magnification=200, 000×. The bar represents 200nm.

FIG. 26 illustrates the antibacterial properties of 1% and 10% BCTP. The bactericidal effect (% killing) was calculated as:

$$cfu(initial) - cfu(post-treatment) \times 100 \; cfu(initial)$$

Figure 27:
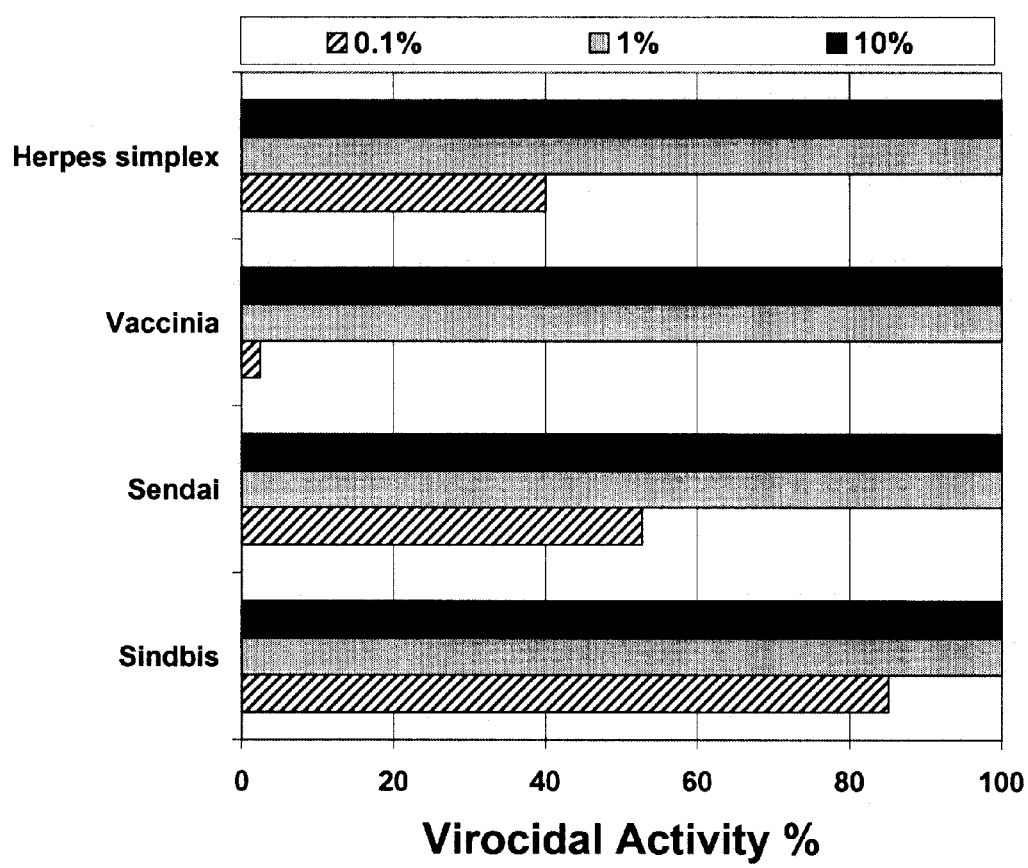

FIG. 27 illustrates the antiviral properties of 10% and 1% BCTP as assessed by plaque reduction assays.

FIG. 28 illustrates several particular embodiments the various emulsions of the present invention.

FIG. 29 illustrates several particular embodiments of the various emulsion compositions invention experimented tried.

Figure 30:
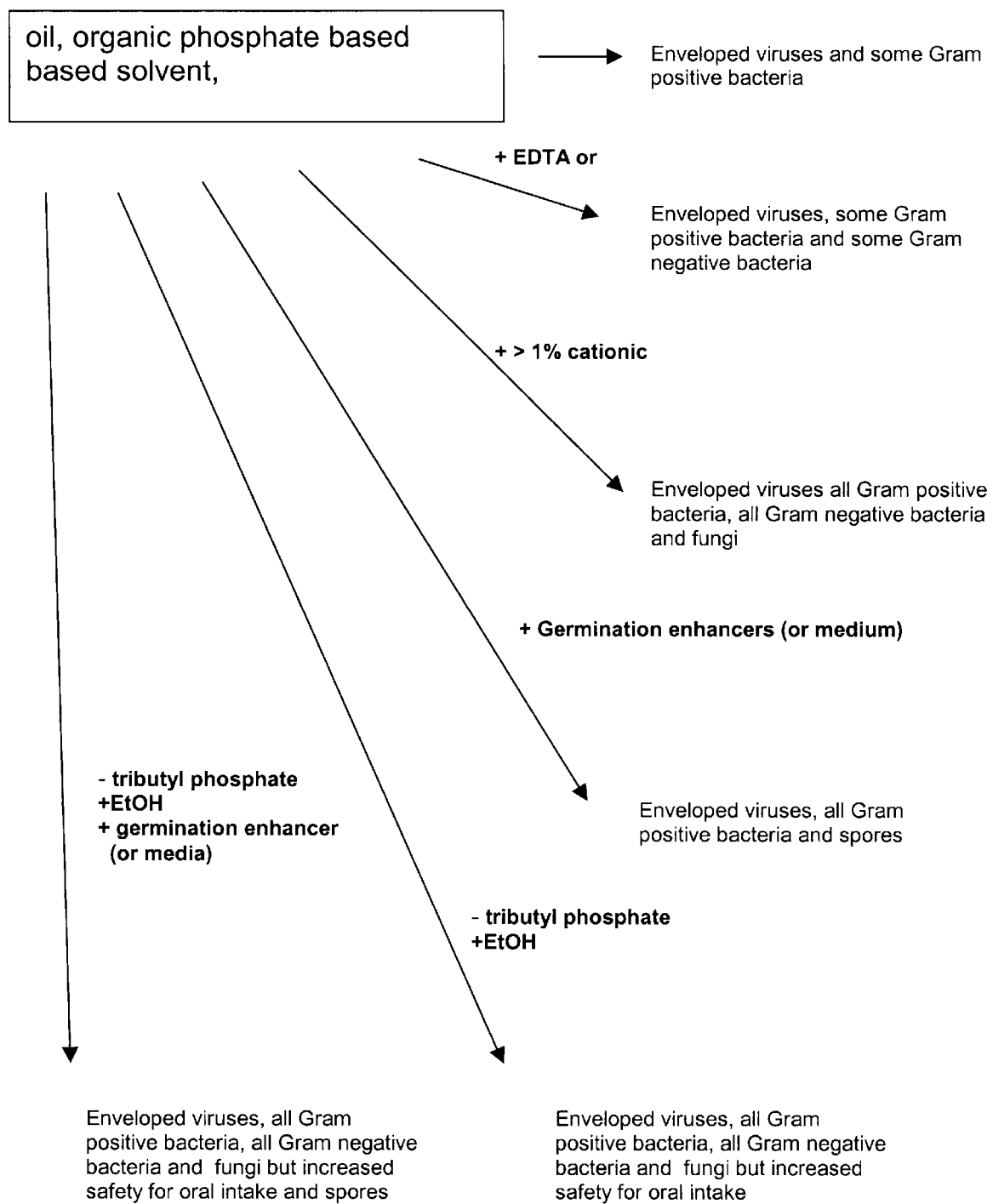

FIG. 30 schematically depicts various generalized formulations and uses of certain embodiments of the present invention.

SUMMARY OF THE INVENTION

The present invention relates to emulsions useful in the treatment, inactivation, decontamination and other methods of preventing microbial infections and/or contaminations.

The present invention also provides a method of inhibiting the infectivity of a microbial agent by contacting the microbes with the emulsion of the present invention.

In certain embodiments, the present invention relates to compositions and methods for decreasing the infectivity, morbidity, and rate of mortality associated with a variety of pathogenic organisms. The present invention also relates to methods and compositions for decontaminating areas colonized or otherwise infected by pathogenic organisms. Moreover, the present invention relates to methods and compositions for decreasing the infectivity of pathogenic organisms in foodstuffs. In particular, decreased pathogenic organism infectivity, morbidity, and mortality is accomplished by contacting the pathogenic organism with an oil-in-water nanoemulsion comprising an oil, an organic solvent, and a surfactant dispersed in an aqueous phase.

It is known that if a water-immiscible lipid phase is mixed into an aqueous phase by mechanical agitation, for example, by means of an ultra dispenser, a dispersion, such as an oil-in-water emulsion, will develop. The stability of the resulting dispersion may require the addition of an emulsifying agent, the molecules of which are adsorbed onto the oil/water interface to form a kind of continuous membrane that prevents direct contact between two adjacent droplets. One advantage of oil-in-water emulsions is that they may readily be diluted with water to a desired concentration and stay stable and retain their structure unchanged.

In addition to discrete oil droplets dispersed in an aqueous phase, oil-in-water emulsions can also contain other lipid structures, such as small lipid vesicles (i.e., lipid spheres which often consist of several substantially concentric lipid bilayers separated from each other by layers of aqueous phase), micelles (i.e., amphiphilic molecules in small clusters of 50–200 molecules arranged so that the polar head groups face outward toward the aqueous phase and the apolar tails are sequestered inward away from the aqueous phase), or lamellar phases (lipid dispersions in which each particle consists of parallel amphiphilic bilayers separated by thin films of water).

These lipid structures are formed as a result of hydrophobic forces which drive apolar residues (i.e., long hydrocarbon chains) away from water. The above lipid preparations can generally be described as surfactant lipid preparations (SLPs). SLPs are minimally toxic to mucous membranes and are believed to be metabolized within the small intestine (Hamouda et al., 1998). SLPs are non-corrosive on plastics and metals in contrast to disinfectants such as bleach. As such, formulations based on SLPs may be particularly useful against bacteria, fungi, viruses and other pathogenic entities.

Certain embodiments of the present invention contemplate compositions and methods for decreasing the infectivity of a pathogenic agent comprising contacting the pathogen with a composition comprising an oil-in-water emulsion in the form of an oil phase distributed in an aqueous phase with a surfactant stabilizer, the oil phase includes an organic phosphate based solvent and a carrier oil, wherein the first emulsion is fusigenic and the second emulsion is lysogenic. In specific embodiments, the contacting is performed for a time sufficient to kill the pathogenic agent or to inhibit the growth of the agent. In other particular embodiments, the present invention provides a method of decontaminating an environmental surface. In such embodiments, the microbial agent is on an environmental surface and contacting the environmental surface with the composition decontaminates the surface of the microbial agent. In some embodiments, the compositions and methods further comprise dyes, paints, and other marking and identification compounds.

In other embodiments, the composition further may comprise a germination enhancer. In particular embodiments, the germination enhancer is selected from the group consisting of L-alanine and inosine or combinations thereof. Other embodiments of the composition further comprise $CaCl_2$ and $NH_4Cl$. Still further embodiments contemplate that the composition further comprises NaCl.

In preferred embodiments, the fusigenic composition is selected from the group consisting of NP9 and P10. In other preferred embodiments, the lysogenic emulsion is bicomponent triton tri-n-butyl phosphate (BCTP). In specific embodiments the oil phase in the emulsion is composed of droplets having a mean particle size in the range from 0.5 to 5 microns. It is contemplated that the surfactant is a non-anionic detergent. In preferred embodiments, the non-anionic detergent is a polysorbate surfactant. In other embodiments, the non-anionic detergent is a polyoxyethylene ether.

In other embodiments, the organic phosphate-based solvent is selected from the group consisting of dialkyl phosphates and trialkyl phosphates. In particularly preferred embodiments, the trialkyl phosphate comprises tri-n-butyl phosphate. The carrier oil may be selected from the group consisting of soybean oil, avocado oil, squalane oil, squalene oil, olive oil, canola oil, com oil, rapeseed oil, safflower oil, sunflower oil, fish oils, flavor oils, water insoluble vitamins and mixtures thereof. In particularly preferred embodiments the carrier oil comprises soybean oil.

In other embodiments, the present invention provides methods of inactivating Gram positive bacteria comprising the step of contacting the bacteria with a composition comprising an oil-in-water emulsion in the form of an oil phase distributed in an aqueous phase with a surfactant stabilizer, the oil phase including an organic phosphate-based solvent and a carrier oil, wherein the first emulsion is fuisigenic and the second emulsion is lysogenic. The Gram positive bacteria may be from the Bacillus family. More specifically the Gram positive bacteria may be *Bacillus anthracis*. In still further embodiments, the present invention provides methods of preventing bacterial infection caused by a Gram positive bacteria in a host, the method comprising the step of administering to the subject a composition comprising a first and a second oil-in-water emulsion in the form of an oil phase distributed in an aqueous phase with a surfactant stabilizer, the oil phase including an organic phosphate-based solvent and a carrier oil, wherein the first emulsion is fusigenic and the second emulsion is lysogenic, wherein administering the composition prevents bacteria infection in the subject. In specific embodiments, the composition may be administered topically, orally, through a porous pad or any other effective administration commonly used by those of skill in the art. In certain embodiments, the present invention contemplates that the emulsion composition is non-toxic and/or non-irritant to the affected subject.

Other embodiments of the present invention provide a method of inactivating bacterial spores comprising contacting the spores with a composition comprising an oil-in-water emulsion in the form of an oil phase distributed in an aqueous phase with a surfactant stabilizer, the oil phase including an organic phosphate-based solvent and a carrier oil, wherein the first emulsion is fusigenic and the second emulsion is lysogenic.

Another aspect of the invention provides a method of inactivating a Gram negative bacteria comprising contacting the Gram negative bacteria with a composition comprising a bacteria-inactivating emulsion comprising an oil-in-water emulsion, in the form of an oil phase distributed in an aqueous phase with a surfactant stabilizer, the oil phase including an organic phosphate-based solvent and a carrier oil; and a compound which enhances interaction of the emulsion by the bacteria, wherein the first emulsion is fusigenic and the second emulsion is lysogenic, such that the Gram negative bacteria is inactivated. In specific embodiments, the Gram negative bacteria are selected from the group consisting of Vibrio, Salmonella, Shigella and Pseudomonas. In preferred embodiments, compounds that enhances the uptake of the emulsion into the bacteria's cells are provided (e.g., ethylenediaminetetraacetic acid [EDTA]). The present invention further contemplates that the disclosed compositions and methods may further comprise other uptake enhancing compounds known those skilled in the art. In particularly preferred embodiments, the EDTA is at a concentration of about 50 to about 250 μM. Of course this is an exemplary range of concentration and any and all concentrations are specifically contemplated herein, including but not limited to 50 μM, 60 μM, 70 μM, 80 μM, 90 μM, 100 μM, 110 μM, 120 μM, 130 μM, 140 μM, 150 μM, 160 μM, 170 μM, 180 μM, 190 μM, 200 μM, 210 μM, 220 μM 230 μM 240 μM and 250 μM.

A further embodiment contemplates a method of preventing bacterial infection caused by a Gram negative bacteria in a subject, the method comprising administering to the subject a composition comprising an oil-in-water emulsion in the form of an oil phase distributed in an aqueous phase with a surfactant stabilizer, the oil phase including an organic phosphate-based solvent and a carrier oil, and a compound which enhances interaction of the emulsion by the bacteria; wherein the first emulsion is fusigenic and the second emulsion is lysogenic, wherein administering the composition prevents bacterial infection in the subject.

Another embodiment of the present invention provides a composition comprising an emulsion wherein the emulsion comprises an oil-in-water emulsion in the form of an oil phase distributed in an aqueous phase with a surfactant stabilizer, the oil phase including an organic phosphate-based solvent and a carrier oil, wherein the first emulsion is fusigenic and the second emulsion is lysogenic. In certain preferred embodiments, the fusigenic emulsion is NP9 or P10. In other preferred embodiments, the lysogenic emulsion is BCTP. In specific embodiments, the composition further comprises a germination enhancer.

Also contemplated are compositions and methods for inactivating a virus comprising the step of contacting the virus with a composition comprising an oil-in-water emulsion in the form of an oil phase distributed in an aqueous phase with a surfactant stabilizer, the oil phase including an organic phosphate-based solvent and a carrier oil, wherein the first emulsion is fusigenic and the second emulsion is lysogenic.

In another embodiment, the present invention contemplates compositions and methods of treating a microbial infection in an animal comprising contacting the animal with a composition comprising a composition comprising an oil-in-water emulsion in the form of an oil phase distributed in an aqueous phase with a surfactant stabilizer, the oil phase including an organic phosphate-based solvent and a carrier oil, wherein the first emulsion is fusigenic and the second emulsion is lysogenic. In certain embodiments, the contacting is via intradernal, subcutaneous, intramuscular or intraperitoneal injection. In other embodiments, the contacting is via oral, nasal, buccal, rectal, vaginal or topical administration. When administered as a pharmaceutical, the present invention contemplates compositions and methods further comprising pharmaceutically acceptable adjutants, excipients, stabilizers, diluents, and the like. In still further embodiments, the present invention contemplates compositions and methods further comprising additional pharmaceutically acceptable bioactive molecules (e.g., antibodies, antibiotics, means for nucleic acid transfection, and vitamins, minerals and co-factors, etc.).

In still further embodiments, the present invention contemplates methods and compositions for decreasing the infectivity, morbidity, and rate of mortality associated with a variety of pathogenic organisms in foodstuffs and food processing facilities.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Definitions

To facilitate the understanding of the present invention, a number of terms and phrases are defined below:

As used herein, the term "pathogen" or "microbe" refers to any agent that is capable of producing an undesirable effect upon a host animal. As such, the terms "pathogen" and "microbe" refer to a class of agents that include bacteria, viruses, bacterial spores, fungi and the like.

As used herein, the term "inactivating," means having the ability to kill, eliminate or reduce the capacity of the agent to infect a host on contact. Without being bound to any theory (an understanding of the mechanism is not necessary to practice the present invention, and the present invention is not limited to any particular mechanism), it appears that inactivation is achieved by surfactant and solvent interactions with microbial cell membranes, which disrupt the cell membrane and cause cell death.

As used herein, the term "fusigenic" is intended to refer to an emulsion that is capable of fusing with the membrane of a microbial agent. Specific examples of fusigenic emulsions are known to those skilled in the art (See e.g., P10 [U.S. Pat. Nos. 5,618,840;5,547,677; and 5,549,901] and NP9 [U.S. Pat. No. 5,700,679] herein incorporated by reference in their entireties). NP9 is a branched poly(oxy-1,2 ethaneolyl),alpha-(4-nonylphenal)-omega-hydroxy-surfactant. This and other surfactants that may be useful in the present invention are described in Table 1 of U.S. Pat. No. 5,662,957, (herein incorporated by reference in its entirety).

As used herein, the term "lysogenic" is intended to refer to an emulsion that is capable of disrupting the membrane of a microbial agent. An exemplary lysogenic composition is BCTP. The present invention shows that the presence of both a lysogenic and a fusigenic agent in the same composition produces a better antimicrobial effect than either composition alone. Methods and compositions of using this improved antimicrobial composition are described in detail herein.

The term "emulsion," as used herein, includes classic oil-in-water dispersions or droplets, as well as other lipid structures which can form as a result of hydrophobic forces which drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Similarly, the term "nanoemulsion," as used herein, includes oil-in-water dispersions comprising smaller lipid structures than those encompassed by the term "emulsion." The present invention contemplates that one skilled in the art will appreciate this distinction when necessary for understanding the specific embodiments herein disclosed.

As used herein, the terms "contacted" and "exposed," when applied to a cell, are used to describe the process by which a composition comprising an emulsion or a nanoemulsion agent are delivered to a target cell or are placed in direct juxtaposition with the pathogenic target organism. To kill or inactivate the pathogen, the agent is delivered to the pathogenic organism in an amount effective to kill or inactivate the organism.

As used herein, the term "germination enhancers" describe compounds that act to enhance germination.

As used herein the term "interaction enhancers" describes compounds that act to enhance interaction of the emulsion with the cell wall of a bacteria (e.g., a Gram negative bacteria).

As used herein, the terms "chemotherapeutic agent" and "therapeutic agent," and grammatical equivalents, are used to describe methods and compositions of the present invention that decrease the infectivity, morbidity, and rate of mortality associated with a variety of pathogenic organisms when administered to a subject detrimentally affected by pathogenic organisms. Such "chemotherapeutic agents" and "therapeutic agents" may or may not further comprise common pharmaceutical acceptable compositions. The therapeutic agents of the present invention are advantageously administered in the form of topical emulsions, injectable compositions and the like. Indeed the therapeutic agents described above may be placed within the nanoemulsion formulations of the present invention. A typical composition for such purpose comprises a pharmaceutically acceptable carrier. When the route is topical, the form may be a cream, ointment, salve or spray.

The terms "pharmaceutically acceptable" or "pharmacologically acceptable," as used herein, refer to compositions that do not produce adverse, allergic or other untoward reactions when administered to an animal or a human. As used herein, "pharmaceutically acceptable carrier" includes any and all solvents, dispersion media, coatings, isotonic and absorption delaying agents and the like.

As used herein, the term "topically" means application to the surface of the skin, mucosa, viscera, etc.

As used herein, the term "topically active agents" indicates a substance or composition which elicits a pharmacological response at the site of application but which is not necessarily an antimicrobial agent.

As used herein, the term "systemically active drugs" is used broadly to indicate a substance or composition which will produce a pharmacological response at a site remote from the point of application or entry into a subject.

As used herein, the term "medical devices" includes any material or device that is used on, in, or through a patient's body in the course of medical treatment (e.g., for a disease or injury). Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incise drapes. Drug delivery devices include, but are not limited to, drug delivery skin patches, drug delivery mucosal patches and medical sponges. Body cavity and personal protection devices, include, but are not limited to, tampons, sponges, surgical and examination gloves, and toothbrushes. Birth control devices include, but are not limited to, IUD's and IUD strings, diaphragms and condoms.

As used herein, the term "purified" or "to purify" refers to the removal of contaminants from a sample.

As used herein, the term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DETAILED DESCRIPTION OF THE INVENTION

The present comprises compositions and methods for the decreasing the infectivity, morbidity, and rate of mortality associated with a variety of pathogenic organisms. The present invention also relates to methods and compositions for decontaminating areas colonized or otherwise infected by pathogenic organisms. Moreover, the present invention relates to methods and compositions for decreasing the infectivity of pathogenic organisms in foodstuffs. In particular, decreased pathogenic organism infectivity, morbidity, and mortality is accomplished by contacting the pathogenic organism with an oil-in-water nanoemulsion comprising an oil, an organic solvent, and a surfactant dispersed in an aqueous phase. Certain preferred embodiments of the present invention are described below. The present invention is not limited to these specific embodiments. The description is provided in the following sections: I) Emulsions and Compositions Thereof; II) Nanoemulsion Compositions Useful as Antimicrobial Agents; III) Decontamination; IV) Pharmaceutical Compositions; V) Foods; VI) Interaction and Germination Enhancers; VII) Kits; and VIII) Examples.

I) Emulsions and Compositions Thereof

In preferred embodiments, the emulsions of the present invention comprise (i) an aqueous phase and (ii) an oil phase and (iii) at least one surfactant. The oil phase comprises oil and an organic solvent.

In certain preferred embodiments, the emulsion comprises about 5 to 50, preferably 10 to 40, more preferably 15 to 30, vol. % aqueous phase, based on the total volume of the emulsion. The aqueous phase comprises water at a pH of about 4 to 10, preferably about 6 to 8. When the emulsions of the present invention contain a germination enhancer, the pH is preferably 6 to 8. The water is preferably deionized (hereinafter "diH$_2$O"). In particular embodiments, the oil phase of the emulsion of the present invention comprises 30–90, preferably 60–80, and more preferably 60–70, vol. % of oil, based on the total volume of the emulsion. Suitable oils include, but are not limited to, soybean oil, avocado oil, squalane oil, squalene oil, olive oil, canola oil, corn oil, rapeseed oil, safflower oil, sunflower oil, fish oils, flavor oils, water insoluble vitamins and mixtures thereof. Preferably soybean oil is used. The oil phase comprises 3–15, preferably 5–10 vol. % of an organic solvent, based on the total volume of the emulsion. Suitable organic solvents include, but are not limited to, organic phosphate based solvents or alcohols. Suitable organic phosphate based solvents include, but are not limited to, dialkyl phosphates and trialkyl phosphates (e.g., tri-n-butyl phosphate). Suitable organic phosphate-based solvents useful in forming the oil-in-water emulsions include, but are not limited to, dialkyl and trialkyl phosphates. In a preferred embodiment, each alkyl group of the di- or trialkyl phosphate has one to ten carbon atoms, more preferably two to eight carbon atoms. The alkyl groups of the di- or trialkyl phosphate can all be the same or can be different. A particularly preferred trialkyl phosphate is tri-n-butyl phosphate, which is a plasticizer. Mixtures of different dialkyl and trialkyl phosphates can be employed. Suitable alcohols include methanol, ethanol, propanol and octanol. In a particularly preferred embodiment, the alcohol is ethanol. The emulsion of the present invention is stabilized with about 3 to 15, preferably about 10% of at least one surfactant, based on the total amount of the composition. The surfactant can be in either the aqueous or the oil phase. Suitable surfactants include, but are not limited to, a variety of ionic and nonionic surfactants, as well as other emulsifiers capable of promoting the formation of oil-in-water emulsions. Any surfactant that allows the oil phase to remain suspended in the water phase can be used. Nonionic surfactants have advantages over ionic emulsifiers they are compatible with a broad pH range and often form more stable emulsions than do ionic (e.g., soap-type) emulsifiers. Preferably, the emulsion of the present invention comprises a non-ionic surfactant such as a polysorbate surfactant such as polyoxyethylene ether. Particularly useful surfactants include the polysorbate detergents sold under the trademarks TWEEN 20, TWEEN 40, TWEEN 60, TWEEN 80, and the phenoxypolyethoxyethanols and polymers thereof including Triton (i.e., X-100, X-301, X-165, X-102, X-200) and Tyloxapol. Other detergents such as those in the Brij family also may be useful. Other particularly preferred surfactants include Triton X-100 (t-octylphenoxypolyethoxyethanol) and Tyloxapol. Nonoxynol-9 can also be used.

Optionally, the emulsions of the present invention may contain a compound capable of increasing the interaction of the emulsion ("interaction enhancer") with the cell wall of Gram negative bacteria such as Vibrio, Salmonella, Shigella and Pseudomonas. The interaction enhancer is preferably premixed with the oil phase; however, it should be understood that the interaction enhancer may be provided in combination with the emulsion in a distinct formulation. In certain preferred embodiments, the interaction enhancer is a chelating agent, e.g., ethylenediaminetetraacetic acid (EDTA) or ethylenebis(oxyethylenenitrilo)tetraacetic acid (EGTA), in a buffer, e.g. tris buffer. In particularly preferred embodiments, the interaction enhancer is at a concentration of about 50 to about 250 $\mu$M. This is an exemplary range of concentrations and any and all concentrations are specifically contemplated herein, including but not limited to 50 $\mu$M, 60 $\mu$M, 70 $\mu$M, 80 $\mu$M, 90 $\mu$M, 100 $\mu$M, 110 $\mu$M, 120 $\mu$M, 130 $\mu$M, 140 $\mu$M, 150 $\mu$M, 160 $\mu$M, 170 $\mu$M, 180 $\mu$M, 190 $\mu$M, 200 $\mu$M, 210 $\mu$M, 220 230 $\mu$M, 240 $\mu$M, and 250 $\mu$M. It is understood that this is merely an exemplary list of agents that act as enhancers of interactions and that any agent that increases the interaction of the bacterial cell wall with the emulsions of the present invention will be useful in the present invention. One skilled in the art will readily be able to determine whether a particular agent has the desired function of action as an interaction enhancer by applying such an agent to a bacterial composition in combination with the emulsion and comparing the effects of the emulsion in the presence and absence of the interaction enhancer. Any agent that increases the interaction and thereby decrease or inhibits the growth of the bacteria in comparison to that parameter in its absence is considered an uptake enhancer. Given the teachings of the present invention, such monitoring should be possible in vitro and in vivo by routine experimentation.

Optionally, the emulsions of the present invention may contain about 0.5, preferably >1.0, more preferably 1.0 wt. % of a cationic halogen containing compound, based on the total weight of the emulsion. The cationic halogen-containing compound is preferably premixed with the oil phase; however, it should be understood that the cationic halogen-containing compound may be provided in combination with the emulsion in a distinct formulation. Suitable cationic halogen containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. Suitable halides include chloride, fluoride, bromide and iodide. Preferably, the halide is chloride. Suitable cationic halogen containing compounds include, but are not limited to, cetylpyridinium chloride (CPC), cetylpyridinium bromide (CPB), and cetyltrimethylammonium bromide (CTAB). In preferred embodiments, the cationic containing compound is cetylpyridinium chloride.

In preferred embodiments, the emulsions of the present invention also contain a germination enhancer. The germination enhancer is preferably incorporated into the aqueous phase prior to formation of the emulsion. It is contemplated that when germination enhancers are added to the emulsions of the present invention, the emulsions are practically suitable for inactivating spores. It is further contemplated that such germination enhancers initiate sporicidal activity only near neutral pH (between pH 6–8 and preferably 7) which can be achieved either by dilution of the emulsions in PBS or by preparations of neutral emulsions. This sporicidal activity can only occur when the spores initiate germination. In certain embodiments, suitable germination enhancing agents of the invention include $\alpha$-amino acids selected from the group consisting of glycine and the L-enantiomers of alanine, valine, leucine, isoleucine, serine, threonine, lysine, phenylalanine, tyrosine, and the alkyl esters thereof. Additional information on the effects of amino acids on germination may be found in U.S. Pat. No. 5,510,104 (herein incorporated by reference in its entirety). A mixture of glucose, fructose, asparagine, sodium chloride (NaCl), ammonium chloride ($NH_4Cl$), calcium chloride ($CaCl_2$) and potassium chloride (KCl) also may be used. In particularly preferred embodiments of the present invention, the formulation comprises the germination enhancers L-alanine, $CaCl_2$, inosine and $NH_4Cl$. Certain growth media also contain germination enhancers and buffers. Thus, when testing the emulsions of the present invention for their ability to inactivate spores, the addition of germination enhancers may not be required, if the tests are conducted using media containing such germination enhancers. Alternatively, the addition of certain growth media to the compositions of the present invention will provide sporicidal activity. The above compounds are merely exemplary germination enhancers and it is understood that germination enhancers commonly used in the art will also be useful in the compositions of the present invention.

Some embodiments of the present invention employ an oil phase containing ethanol. For example, in some embodiments, the emulsions of the present invention contain (i) an aqueous phase and (ii) an oil phase containing ethanol as the organic solvent and optionally a germination enhancer, and (iii) Tyloxapol as the surfactant (preferably 2–5%, more preferably 3%). This formulation is highly efficacious against microbes and is also non-irritating and non-toxic to mammalian users (and can thus be contacted with mucual membranes).

In preferred embodiments, the emulsions of the present invention, the oil phase is preferably distributed throughout the (1) aqueous phase as droplets having a mean particle size in the range from about 1–2 microns, preferably 0.2 to 0.8, and more preferably about 0.8 microns.

In other embodiments, the aqueous phase can be distributed in the oil phase.

In still other embodiments, the emulsions of the present invention comprise a first emulsion emulsified within a second emulsion, wherein (a) the first emulsion comprises (i) an aqueous phase; and (ii) an oil phase comprising an oil and an organic solvent; and (iii) a surfactant; and (b) the second emulsion comprises (i) an aqueous phase; and (ii) an oil phase comprising an oil and a cationic containing compound; and (iii) a surfactant.

The bacteria inactivating oil-in-water emulsions used in the methods of the present invention can be formed using classic emulsion forming techniques known in the art. In brief, the oily phase is mixed with the aqueous phase under relatively high shear forces to obtain an oil-in-water emulsion containing oil droplets, which are approximately 0.5 to 5 microns, preferably 1–2 microns, in diameter. The emulsion is formed by blending the oily phase with an aqueous phase (e.g., water) on a volume-to-volume basis ranging from about 1:9 to 5:1, preferably about 5:1 to 3:1, most preferably 4:1, oily phase to aqueous phase. The oil and aqueous phases can be blended using any apparatus capable of producing shear forces sufficient to form an emulsion (e.g., French Press or commercial high shear mixers). Methods of producing such emulsions are described in U.S. Pat. Nos. 5,103,497 and 4,895,452 (herein incorporated by reference in their entireties).

The emulsions used in the methods of the present invention consists primarily of droplets of an oily discontinuous phase dispersed in an aqueous continuous phase, such as water. The emulsions are highly stable, and do not decompose even after long storage periods. The bacteria inactivating emulsions are non-toxic and safe when swallowed, inhaled, or applied to the skin. This is in contrast to certain chemical microbicides, which are known irritants. The bacteria-inactivating emulsions of the present invention are also non-toxic to plants.

The emulsions of the present invention can be rapidly produced in large quantities and are stable for many months at a broad range of temperatures. Undiluted, they tend to have the texture of a semi-solid cream and can be applied topically by hand or mixed with water. Diluted, they tend to have a consistency and appearance similar to skim milk, and can be sprayed to decontaminate surfaces or potentially interact with aerosolized spores before inhalation. These properties provide a flexibility that is useful for a broad range of antimicrobial applications. Additionally, these properties make the emulsions of the present invention particularly well suited to decontamination applications.

As stated above, at least a portion of the emulsion may be in the form of lipid structures including, but not limited to, unilamellar, multilamellar, and paucliamellar lipid vesicles, micelles, and lamellar phases.

The emulsions of the present invention can be formulated into sprays and lotions by including a carrier. Suitable carriers include, but are not limited to, a cream, an ointment, a bioadhesive, an oil, an alkene, a terpene, a glycol, an ester, an ether, or an alcohol or a mixture thereof. When the methods and compositions are intended for human use, the carrier is preferably a pharmaceutically acceptable carrier such as acetate, benzoate, boric acid, calcium carbonate, carboxymethylcellulose, cellulose, citric acid, dextrate, dextrose, ethyl alcohol, glucose, hydroxymethylcellulose, lactose, magnesium stearate, maltodextrin, mannitol, microcrystalline cellulose, oleate, polyethylene glycols, potassium diphosphate, potassium phosphate, saccharose, sodium diphosphate, sodium phosphate, sorbitol, starch, stearic acid and its salts, sucrose, talc, vegetable oils, or water.

More particularly in other embodiments, the present invention provides a number of exemplary emulsions including BCTP and Novaclor 401. BCTP is a water-in oil nanoemulsion, in which the oil phase was made from soybean oil, tri-n-butyl phosphate, and Triton X-100 in 80% water. Novaclor 401 is prepared by mixing equal volumes of BCTP with P10 which is a liposome-like compound made of glycerol monostearate, refined oya sterols, TWEEN 60, soybean oil, a cationic ion halogen-containing CPC and peppermint oil. The GENEROL family are a group of a polyethoxylated soya sterols (Henkel Corporation, Ambler, Pa.). Emulsion formulations are given in Table 1 for certain embodiments of the present invention. These particular formulations may be found in U.S. Pat. Nos. 5,700,679 (NN); 5,618,840;5,549,901 (P10); and 5,547,677 (herein incorporated by reference in their entireties). Certain other emulsion formulations experimented with are presented in FIG. 29. Moreover, FIG. 30 schematically presents generalized formulations and uses of certain embodiments of the present invention.

TABLE 1

| Surfactant Name | Lipid Preparations Oil Phase Formula | Water to Oil Phase Ratio (Vol/Vol) |
| --- | --- | --- |
| BCTP | 1 vol. Tri(N-butyl)phosphate<br>1 vol. Triton X-100<br>8 vol. Soybean oil | 4:1 |
| NN | 86.5 g Glycerol monooleate<br>60.1 ml Nonoxynol-9<br>24.2 g GENEROL 122<br>3.27 g Cetylpyridinium chloride<br>554 g Soybean oil | 3:1 |
| P10 | 86.5 g Glycerol monooleate<br>21.2 g Polysorbate 60<br>24.2 g GENEROL 122<br>3.27 g Cetylpyddinium chloride<br>4 ml Peppermint oil<br>554 g Soybean oil | 3.2:1 |
| SS | 86.5 g Glycerol monooleate<br>21.2 g Polysorbate 60<br>24.2 g GENEROL 122<br>3.27 g Cetylpyridinium chloride<br>554 g Soybean oil | 3.2:1<br>(1% bismuth in water) |

Of course the compositions listed above are only exemplary and those of skill in the art will be able to alter the amounts of the components to arrive at a nanoemulsion composition suitable for the purposes of the present invention. Those skilled in the art will understand that the ratio of oil phase to water as well as the individual oil carrier, surfactant CPC and organic phosphate buffer, components of each composition may vary.

Although certain composition comprising BCTP have a water to oil ratio of 4:1, it is understood that the BCTP may be formulated to have more or less of a water phase. For example, there could be 3, 4, 5, 6, 7, 8, 9, 10, or more parts of the water phase to each part of the oil phase. The same holds true for the P10 formulation. Similarly, the ratio of Tri(N-butyl)phosphate: Triton X-100: soybean oil also may be varied.

Although Table 1 lists specific amounts of glycerol monooleate, polysorbate 60, GENEROL 122, cetylpyridinium chloride, and carrier oil for P10, these are merely exemplary. An emulsion that has the properties of P10 may be formulated that has different concentrations of each of these components or indeed different components that will fulfill the same function.

For example, the emulsion may have between about 80 to about 100 g of glycerol monooleate in the initial oil phase. In other embodiments, the emulsion may have between about 15 to about 30 g polysorbate 60 in the initial oil phase. In yet another embodiments the emulsion may comprise between about 20 to about 30 g of a GENEROL sterol, in the initial oil phase.

In certain embodiments of the emulsions comprising CPC, the CPC content may be varied from between about 2.5 g to about 4 g. In still other embodiments, the amount of carrier oil in which the other components are located may be varied to be between about 500 g to about 1000 g. The CPC is only an exemplary cationic halogen-containing compound; other compounds that may be useful instead of CPC include, but are not limited to, cetypridinium bromide (CPB), and cetyltrimethylammonium bromide (CTAB). Other cationic halogen containing compounds having a which can be used include, for example, cetyltrimethylammonium chloride, cetyidimethylethylammonium bromide, cetylbenzyldimethylammonium chloride, cetyltributylphosphonium bromide, dodecyltrimethylammonium bromide, and tetrad ecyltrimethylammonium bromide.

In general, the invention contemplates that BCTP and its derivative Novaclor 401 appear to have great potential as environmental decontamination agents and for treatment of casualties in both military and terrorist attack. The inactivation of a broad range of pathogens, including vegetative bacteria and enveloped viruses (Chatlyyne et al, 1996) and bacterial spores, combined with low toxicity in experimental animals, make these emulsions suitable for use as a general decontamination agent before a specific pathogen is identified. The nanoemulsions can be rapidly produced in large quantities and are stable for many months at a broad range of temperatures. These properties provide a flexibility that is useful for a broad range of decontamination applications.

While not limited to any particular proposed mechanism (an understanding of the mechanism is not needed to practice the invention, and the invention is not limited to any particular mechanism(s)), it is contemplated that the emulsions of the present invention remove proteins from the bacterial membranes. Thus any surfactant that will "strip" the membrane of its proteins may be considered useful in the methods and compositions of the present invention. Surfactants useful in forming the emulsions used in the methods of the present invention include a variety of anionic and nonionic surfactants, as well as other emulsifiers capable of promoting the formation of oil-in-water emulsions. In general, the emulsifier are relatively hydrophilic, and blends of emulsifiers can be used to achieve the necessary qualities. Nonionic surfactants have advantages over ionic emulsifiers they are compatible with a broad pH range and often form more stable emulsions than do ionic (e.g., soap-type) emulsifiers. In some embodiments, particularly useful surfactants include the detergents sold under the trademarks TWEEN 20, TWEEN 40, TWEEN 60, TWEEN 80, and the phenoxypolyethoxyethanols like Triton (e.g., X-100, X-301, X-165, X-102, and X-200). Other detergents such as those in the Brij family also may be useful. A particularly preferred surfactant is Triton X-100 (t-octylphenoxypolyethoxyethanol).

BCTP contains Triton X-100 while SS and P10 contain TWEEN 60, and NN contained nonoxynol-9 surfactant. Each is a non-ionic surfactant, but differs in its chemistry and biological characteristics. Nonoxynol-9 has strong spermicidal activity and it is widely used as a component of vaginally delivered contraceptive products (Lee, 1996). It has been claimed to have virucidal effect against enveloped viruses (Hermonat et al., 1992; Zeitlin et al, 1997). However, nanoxynol-9 has not been shown to be effective against nonenveloped viruses (Hermonat et al., 1992). TWEEN 60 (polyoxyethylenesorbitan monostearate), together with TWEEN 20, TWEEN 40 and TWEEN 80, belongs to polysorbates which are used as emulsifiers in a number of pharmaceuticals. Some are also used as compounds of adjuvants, which possess significant potential for the development of new vaccines (O'Hagan, 1998). These surfactants also appear to have virucidal effects on lipid-enveloped viruses (Eriksson et al., 1994). Triton X-100 is a strong non-ionic detergent and dispersing agent widely used to extract lipids and proteins from biological structures. It also has virucidal effect against broad spectrum of enveloped viruses (Maha and Igarashi, 1997; Portocala et al., 1976; Horowitz et al., 1992). Due to this anti-viral activity; it is employed to inactivate viral pathogens in fresh frozen human plasma (Horowitz et al., 1992).

Again, while not limited to any particular proposed mechanism, the invention contemplates that the organic phosphate-based solvents employed in the emulsions serve to remove or disrupt the lipids in the membranes of the pathogens. Thus, any such solvent that removes the sterols or phospholipids in the membranes will be useful in the emulsions. Organic phosphate-based solvents useful in forming the oil-in-water emulsions include dialkyl and trialkyl phosphates. In a preferred embodiment, each alkyl group of the di- or trialkyl phosphate has one to ten carbon atoms, more preferably two to eight carbon atoms. The alkyl groups of the di- or trialkyl phosphate can all be the same or can be different. A particularly preferred embodiment comprises a trialkyl phosphate, and more particularly, tri-n-butyl phosphate (a plasticizer). Mixtures of different dialkyl and trialkyl phosphates can be employed. In addition, alcohols may be employed as a solvent (e.g., octanol, or ethanol).

II) Nanoemulsion Compositions Useful as Antimicrobial Agents

The nanoemulsions structure of the certain embodiments of the emulsions of the present invention may play an important role in their biocidal activity as well as contributing to the non-toxicity of these emulsions. The active component in BCTP, Triton-X100 shows less biocidal activity against virus at concentrations equivalent to 11% BCTP. Adding the oil phase to the detergent and solvent markedly reduces the toxicity of these agents in tissue culture at the same concentrations. While not being bound to any theory (an understanding of the mechanism is not necessary to practice the present invention, and the present invention is not limited to any particular mechanism), it is suggested that the nanoemulsion enhances the interaction of its components with the pathogens thereby facilitating the inactivation of the pathogen and reducing the toxicity of the individual components. It should be noted that when all the components of BCTP are combined in one composition but are not in a nanoemulsion structure, the mixture is not as effective as an antimicrobial as when the components are in a nanoemulsion structure.

As shown in FIG. 28 the base emulsion which comprises an oil, an organic solvent and a surfactant is useful in treating enveloped viruses and some Gram positive bacteria.

In some embodiments, the addition of an interaction enhancer to the base emulsion produces a composition which is useful in treating enveloped viruses, some Gram positive bacteria and some Gram negative bacteria.

In some embodiments, addition of greater than or equal to 1% of a cationic containing compound to the base emulsion produces a product which is usefuil in treating enveloped viruses, Gram positive bacteria, Gram negative bacteria and fungi.

In still other embodiments, addition of a germination enhancer (or growth medium) to neutral emulsion produces a composition that is useful in treating bacterial spores in addition to enveloped viruses, Gram negative bacteria, and Gram positive bacteria.

FIG. 28 exemplifies some of the microbes that can be treated with the inventive emulsions.

In certain embodiments of the present invention, the nanoemulsion comprises BCTP. Another preferred embodiment comprises Novaclor 401. BCTP is a nanoemulsion made of soybean oil, Triton X-100 detergent and tri-n-butyl phosphate in 80% water.

Novaclor 401 is mix of this emulsion (BCTP) and an additional liposome-like compound containing cetylpyridinium chloride (CPC), this compound is described herein as P10). The Novaclor 401 emulsion is manufactured by first making the P10 emulsion and BCTP emulsions separately. A mixture of these two emulsions is then re-emulsified to produce a fresh emulsion composition termed Novaclor 401, also known to those skilled in the art as BCTP401. Methods of producing such emulsions are described in U.S. Pat. Nos. 5,103,497 and 4,895,452 (herein incorporated by reference in their entireties). These compounds have broad-spectrum antimicrobial activity, and are able to inactivate vegetative bacteria through membrane disruption.

The antibacterial, sporicidal, antiviral, and antifungal properties, as well as the in vivo effectiveness of certain embodiments of the methods and compositions of the present invention are discussed below.

Antibacterial Properties

The methods of the present invention can rapidly inactivate Gram positive bacteria. In preferred embodiments, the inactivation of bacteria occurs after no more than five to ten minutes. Thus, bacteria may be contacted with an emulsion according to the present invention and will be inactivated in a rapid and efficient manner. It is expected that the period of time between the contacting and inactivation may be as little as 5–10 minutes where the bacteria is directly exposed to the emulsion. However, it is understood that when the emulsions of the present invention are employed in a therapeutic context and applied systemically, the inactivation may occur over a longer period of time including, but not limited to, 5, 10, 15, 20, 25 30, 60 minutes post application. Further, in additional embodiments it may be that the inactivation may take two, three, four, five or six hours to occur.

In other embodiments, the compositions and methods of the invention can also rapidly inactivate certain Gram negative bacteria. In such methods, the bacteria inactivating emulsions are premixed with a compound which increases the interaction of the emulsion by the cell wall. The use of these enhancers in the compositions of the present invention is discussed herein below. It should be noted that certain emulsions especially those comprising enhancers are effective against certain Gram positive and negative bacteria and may be administered orally where they will come in contact with necessary gut bacteria.

Figure 26:
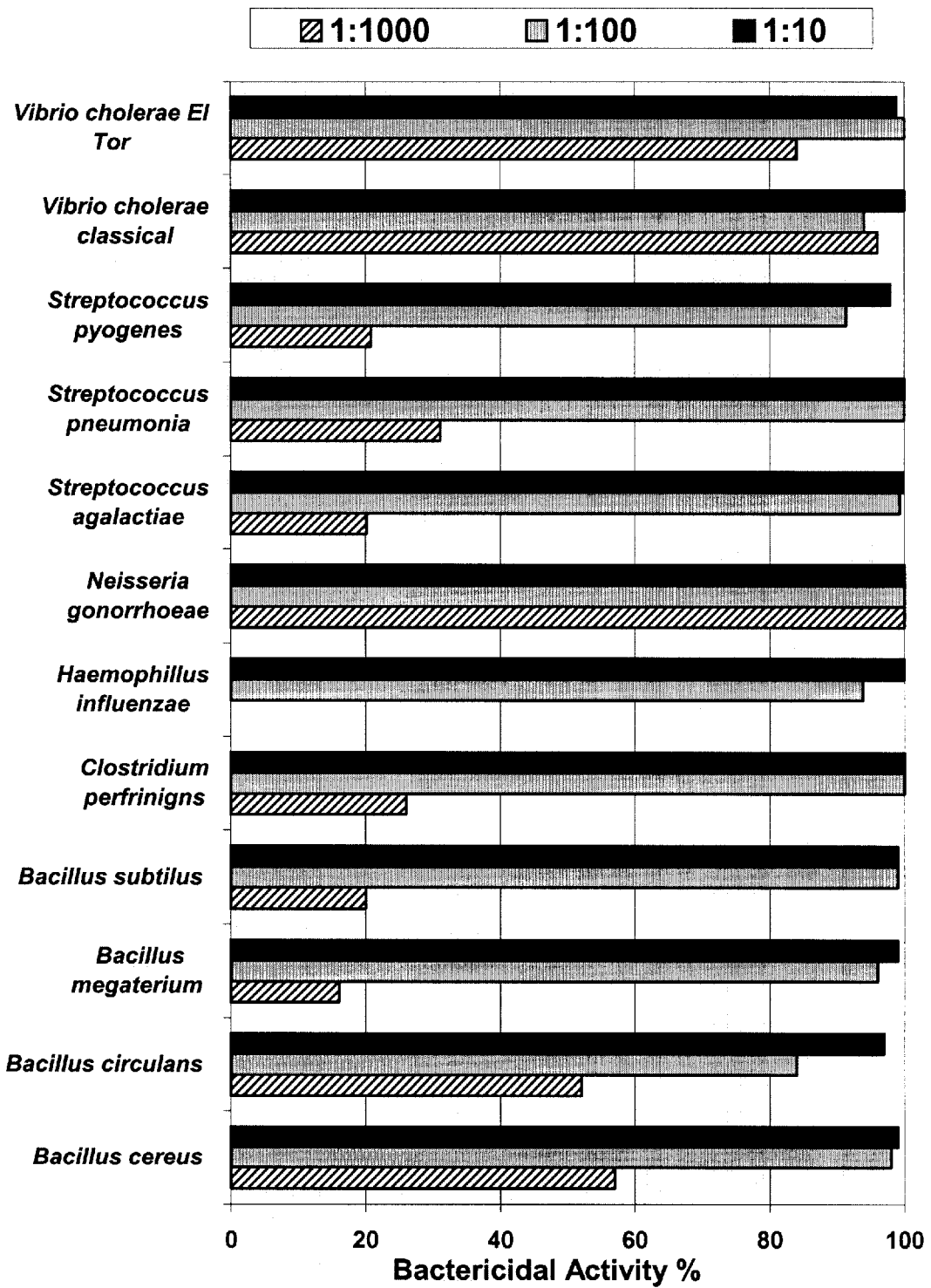

In specific embodiments, the present invention has shown that the emulsions of the present invention have potent, selective biocidal activity with minimal toxicity against vegetative bacteria. BCTP was highly effective against B. cereus, B. circulans and B. megaterium, C perfringens, H. influenzae, N. gonorrhoeae, S. agalactiae, S. pneumonia, S. pyogenes and V. cholerae classical and Eltor (FIG. 26). This inactivation starts immediately on contact and is complete within 15 to 30 minutes for most of the susceptible microorganisms.

Sporicidal Properties

In certain specific embodiments, the present invention has demonstrated that the emulsions of the present invention have sporicidal activity. Without being bound to any theory (an understanding of the mechanism is not necessary to practice the present invention, and the present invention is not limited to any particular mechanism), it is proposed the inventors propose that the sporicidal ability of these emulsions occurs through initiation of germination without complete reversion to the vegetative form leaving the spore susceptible to disruption by the emulsions. The initiation of germination could be mediated by the action of the emulsion or its components.

The results of electron microscopy studies show disruption of the spore coat and cortex with disintegration of the core contents following BCTP treatment. Sporicidal activity appears to be mediated by both the Triton X-100 and tri-n-butyl phosphate components since nanoemulsions lacking either component are inactive in vivo. This unique action of the emulsions, which is similar in efficiency to 1% bleach, is interesting because Bacillus spores are generally resistant to most disinfectants including many commonly used detergents (Russell, 1990).

The present invention demonstrates that mixing BCTP with B. cereus spores before injecting into mice prevented the pathological effect of B. cereus. Further, the present invention shows that BCTP treatment of simulated wounds contaminated with B. oereus spores markedly reduced the risk of infection and mortality in mice. The control animals, which were injected with BCTP alone diluted 1:10, did not show any inflammatory effects proving that BCTP does not have cutaneous toxicity in mice. These results suggest that immediate treatment of spores prior to or following exposure can effectively reduce the severity of tissue damage of the experimental cutaneous infection.

Other experiments conducted during the development of the present invention compared the effects of BCTP and other emulsions derived from BCTP to inactivate different Bacillus spores. BCTP diluted up to 1:1000 (v/v) inactivated more than 90% of B. anthracis spores in four hours, and was also sporicidal against three other Bacillus species through the apparent disruption of spore coat. Novaclor 401 diluted 1:1000 had more sporicidal activity against B. anthracis, B. cereus, and B. subtilis and had an onset of action in less than 30 minutes. In mice, mixing BCTP with B. cereus before subcutaneous injection or wound irrigation with BCTP 1 hour following spore inoculation resulted in over 98% reduction in skin lesion size. Mortality was reduced 4-fold in the latter experiment. The present compositions are stable, easily dispersed, non-irritant and nontoxic compared to the other available sporicidal agents.

The bacteria-inactivating oil-in-water emulsions used in the methods of the present invention can be used to inactivate a variety of bacteria and bacterial spores upon contact.

For example, the presently disclosed emulsions can be used to inactivate Bacillus including *B. cereus, B. circulans* and *B. megatetium*, also including Clostridium (e.g., *C. botulinum* and *C. tetani*). The methods of the present invention may be particularly useful in inactivating certain biological warfare agents (e.g., *B. anthracis*). In addition, the formulations of the present invention also find use in combating *C. perftingens, H. influenzae, N. gonorrhoeae, S. agalactiae, S. pneumonia, S. pyogenes* and *V. cholerae* classical and Eltor (FIG. 26).

Antiviral Properties

In additional embodiments, it was demonstrated that the nanoemulsion compositions of the present invention have anti-viral properties. The effect of these emulsions on viral agents was monitored using plaque reduction assay (PRA), cellular enzyme-linked immunosorbent assay (ELISA), P-galactosidase assay, and electron microscopy (EM) and the cellular toxicity of lipid preparations was assessed using a (4,5-dimethylthiazole-2-yl)-2,5 diphenyltetrazolium (MTT) staining assay (Mosmann 1983).

There was a marked reduction of influenza A infectivity of MDCK cells as measured by cellular ELISA with subsequent confirmation by PRA. BCTP and SS at dilution 1:10 reduced virus infectivity over 95%. Two other emulsions showed only intermediate effects on the virus reducing infectivity by approximately 40% at dilution 1:10. BCTP was the most potent preparation and showed undiminished virucidal effect even at dilution 1:100. Kinetic studies showed that 5 min incubation of virus with BCTP at 1:10 dilution completely abolished its infectivity. Triton X-100, an active compound of BCTP, at dilution 1:5000 only partially inhibited the infectivity of virus as compared to BCTP, indicating that the nanoemulsion itself contributes to the anti-viral efficacy. To further examine the anti-viral properties of BCTP, its action on non-enveloped viruses was investigated. The BCTP treatment did not affect the replication of lacZ adenovirus construct in 293 cells as measured using β-galactosidase assay. When examined with EM, influenza A virus was completely disrupted after incubation with BCTP while adenovirus remained intact.

In addition, pre-incubation of virus with 10% and 1% BCTP in PBS completely eliminates herpes, sendai, sindbis and vaccinia viruses as assessed by plaque reduction assays (FIG. 27). Time course analyses showed the onset of inactivation to be rapid and complete within 5 minutes of incubation with 10% BCTP and within 30 minutes with 1% BCTP. Adenovirus treated with different dilutions of BCTP showed no reduction in infectivity.

The efficacy of certain BCTP based compositions against various viral onslaught and their minimal toxicity to mucous membranes demonstrate their potential as effective disinfectants and agents for prevention of diseases resulting from infection with enveloped viruses.

Antifungal Properties

Yet another property of the nanoemulsions of the present invention is that they possess antifungal activity. Common agents of fungal infections include various species of the genii Candida and Aspergillus, and types thereof, as well as others. While external fungus infections can be relatively minor, systemic fungal infections can give rise to serious medical consequences. There is an increasing incidence of fungal infections in humans, attributable in part to an increasing number of patients having impaired immune systems. Fungal disease, particularly when systemic, can be life threatening to patients having an impaired immune system.

Experiments conducted during the development of the present invention have shown that 1% BCTP has a greater than 92% fungistatic activity when applied to *Candida albicans*. Candida was grown at 37° C. overnight. Cells were then washed and counted using a hemacytometer. A known amount of cells were mixed with different concentrations of BCTP and incubated for 24 hours. The Candida was then grown on dextrose agar, incubated overnight, and the colonies were counted. The fungistatic effect of the BCTP was determined as follows:

$$\text{Fungistatic Effect } (FSE) = \left(1 - \frac{\text{\# of treated cells} - \text{Initial \# of cells}}{\text{\# of untreated cells} - \text{Initial \# of cells}}\right) \times 100$$

Given that the present invention demonstrates that BCTP is fungistatic, it is contemplated that other formulations of the present invention (e.g., composition comprising Novaclor 401) are also fungistatic. One of skill in the art will be able to take the formulations of the present invention and place them into appropriate formulations for the treatment of fungal disease. The nanoemulsions of the present invention could be used to combat infections such as athletes foot, candidosis and other acute or systemic fungal infections.

In Vivo Effects

Animal studies demonstrated the protective and therapeutic effect of BCTP in vivo. *Bacillus cereus* infection in experimental animals has been used previously as a model system for the study of anthrax (See e.g., Burdon and Wende, 1960; Burdon et al, 1967; Lamanna and Jones, 1963). The disease syndrome induced in animals experimentally infected with *B. cereus* is in some respects similar to anthrax (Drobniewski, 1993; Fritz et al., 1995). Experiments conducted during the development of the invention present invention demonstrated that mixing BCTP with *B. cereus* spores before injecting into mice prevented the pathological effect of *B. cereus*. Further, it was demonstrated that BCTP treatment of simulated wounds contaminated with *B. cereus* spores markedly reduced the risk of infection and mortality in mice. The control animals, which were injected with BCTP alone diluted 1:10, did not show any inflammatory effects proving that BCTP does not have cutaneous toxicity in mice. These results suggest that immediate treatment of spores prior to or following exposure can effectively reduce the severity of tissue damage of the experimental cutaneous infection.

In a particular example, Guinea Pigs were employed as experimental animals for the study of *C. perftingens* infection. A 1.5 cm skin wound was made, the underlying muscle was crushed and infected with $5 \times 10^7$ cfu of *C. perftingens* without any further treatment. Another group was infected with the same number of bacteria, then 1 hour later it was irrigated with either saline or BCTP to simulate post-exposure decontamination. Irrigation of experimentally infected wounds with saline did not result in any apparent benefit. BCTP irrigation of the wound infected with *C. perffingens* showed marked reduction of edema, inflammatory reaction and necrosis. As such, it was demonstrated that certain formulations of the present invention can be used to combat a bacterial infection.

Further, a subcutaneous injection of 10% BCTP did not cause distress in experimental animals and resulted in no gross histological tissue damage. All rats in the oral toxicity study showed weight gain over the study period. No adverse clinical signs were noted and all tissues appeared within normal limits on gross examination. Bacterial cultures from the stools of treated animals were not significantly different from those of untreated animals.

III) Decontamination

As described earlier, the contamination of farmlands with *B. anthracis* leads to a fatal disease in domestic, agricultural, and wild animals (Dragon and Rennie, 1995) as well as human infection caused by contact with infected animals or infected animal products (Welkos et al., 1986). Although *Bacillus anthracis* infection in humans is no longer common, animal anthrax infections still represent a significant problem due to the difficulty in decontaminating infected land and farms. Despite the fact that there is an available vaccine, resistance resulting from genetic mixing of different strains often renders this vaccine largely ineffective (Mobley, 1995). In addition, spore producing bacteria that cause diseases such as anthrax, botulism, gas gangrene and tetanus have potential uses as biological weapons. The release of such agents as biological weapons could be catastrophic in light of the fact that such diseases will readily spread through the air.

In light of the foregoing discussion, it becomes increasingly clear that cheap, fast and effective methods of killing bacterial spores are needed for decontaminating purposes. The inventive compounds have great potential as environmental decontamination agents and for treatment of casualties in both military and terrorist attacks. The inactivation of a broad range of pathogens, including vegetative bacteria and enveloped viruses (Chatlyyne et al., 1996) and bacterial spores (Hamouda et al., 1999), combined with low toxicity in experimental animals, make them (i.e., the inventive compounds) particularly well suited for use as general decontamination agents before a specific pathogen is identified.

The sporicidal effect starts almost immediately and occurs within 30 minutes of incubation with the emulsions. Induction of germination using Inosine and L-alanine resulted in acceleration of the sporicidal activity of the emulsion and inhibition of initiation of germination with D-alanine delayed sporicidal activity. While an understanding of the mechanism is not necessary to practice the present invention, and the present invention is not limited to any particular mechanism, based on these observations, it appears that the sporicidal ability of these emulsions occurs through initiation of germination without complete reversion to the vegetative form leaving the spore susceptible to disruption by the emulsions. The initiation of germination could be mediated by the action of the emulsion or its components (Hamouda et al., 1999). This unique action of the emulsions, which is better in efficiency than 1% bleach, is interesting because Bacillus spores are generally resistant to most disinfectants including many commonly used detergents (Russell, 1990).

Thus, certain embodiments of the present invention specifically contemplate the use of these emulsions in disinfectants and detergents to decontaminate soil, machinery, vehicles and other equipment, and waterways that may have been subject to a biological warfare attack. Such decontamination procedures are well known to those of skill in the art and may involve simple application of the formulation in the form of a liquid spray or may require a more rigorous regimen. Also, the present emulsions could be used to treat crops for various plant viruses (in place of or for use with conventional antibiotics).

In addition to their use in decontamination of land and equipment, it is envisioned that these formulations are also employed in household detergents for general disinfectant purposes. Moreover, some embodiments of the present invention can be used to prevent contamination of food with bacteria or fungi. This can be done either in the food preparation process, or by addition to the food as an additive, disinfectant, or preservative.

The inventive emulsions are preferably used on hard surfaces in liquid form. Accordingly, the foregoing components are admixed with an aqueous carrier liquid. The choice of aqueous carrier liquid is not critical. It should be safe and it should be chemically compatible with the inventive emulsions. The aqueous carrier liquid can comprise solvents commonly used in hard surface cleaning compositions. Such solvents should be compatible with the inventive emulsions and must be chemically stable at the pH of the emulsions. They should also have good filming/residue properties. Solvents for use in hard surface cleaners are described, for example, in U.S. Pat. No. 5,108,660 (herein incorporated by reference in its entirety).

Preferably, the aqueous carrier liquid is water or a miscible mixture of alcohol and water. The alcohol can be used to adjust the viscosity of the compositions. The alcohols are preferably C2–C4 alcohols. Ethanol is most preferred. Preferably, the aqueous carrier liquid is water or a water-ethanol mixture containing from about 0 to about 50% ethanol. The present invention also embodies a non-liquid composition. The non-liquid compositions can be in granular, powder or gel forms, preferably in granular forms.

Optionally, some compositions herein contain auxiliary materials that augment cleaning and aesthetics so long as they do not interfere with the activity of the inventive emulsions. The compositions can optionally comprise a non-interfering auxiliary surfactant. A wide variety of organic, water-soluble surfactants can optionally be employed. The choice of auxiliary surfactant depends on the desires of the user with regard to the intended purpose of the compositions and the commercial availability of the surfactant. Other optional additives such as perfumes, brighteners, enzymes, colorants, and the like can be employed in the compositions to enhance aesthetics and/or cleaning performance. Detergent builders can also be employed in the compositions.

Detergent builders sequester calcium and magnesium hardness ions that might otherwise bind with and render less effective the auxiliary surfactants or co-surfactants. Builders are especially useful when auxiliary surfactants or cosurfactants are employed, and are even more useful when the compositions are diluted prior to use with exceptionally hard tap water e.g., above about 12 grains/gallon. Suds suppressors can also be included. The compositions therefore preferably comprise a sufficient amount of a suds suppressor to prevent excessive sudsing during employment of the compositions on hard surfaces. Suds suppressors are especially useful in formulations for no-rinse application of the composition. The suds suppressor can be provided by known and conventional means. Selection of the suds suppressor depends on its ability to formulate in the compositions, and the residue and cleaning profile of the compositions. The suds suppressor must be chemically compatible with the components in the compositions, it must be functional at the pH range described herein, and it should not leave a visible residue on cleaned surfaces. Low-foaming cosurfactants can be used as suds suppressor to mediate the suds profile in the compositions. Co-surfactant concentrations between about 1 part and about 3% are normally sufficient.

Examples of suitable cosurfactants for use herein include block copolymers (e.g., Pluronic and Tetronic (BASF Company) and alkylated (e.g., ethoxylated/propoxylated) primary and secondary alcohols (e.g., Tergitol [Union Carbide]; Poly-Tergento [Olin Corporation]). The optional suds suppressor preferably comprises a silicone-based material. These materials are effective as suds suppressors at very low concentrations. At low concentrations, the silicone-based suds suppressor is less likely to interfere with the cleaning performance of the compositions. An example of suitable silicone-based suds suppressors for use in the compositions is Dow Corning DSE. These optional but preferred silicone-based suds suppressors can be incorporated into the composition by known and conventional means.

IV) Pharmaceutical Compositions

The present invention also contemplates that the fusigenic and lysogenic emulsions described herein may be employed in pharmaceutical compositions to be advantageously employed in combating and/or treating microbial infections. Thus, such compositions may be employed to reduce infection, kill microbes, inhibit microbial growth or otherwise abrogate the deleterious effects of microbial infection.

For in vivo applications, the emulsion compositions can be administered in any effective pharmaceutically acceptable form to warm blooded animals, including human and animal subjects. Generally, this entails preparing compositions that are essentially free of pyrogens, as well as other impurities that could be harmfuil to humans or animals. For example, in yet another embodiment, the inventive emulsions can be used in various applications with animals.

Particular examples of pharmaceutically acceptable forms include but are not limited to oral, nasal, buccal, rectal, vaginal, topical or nasal spray or in any other form effective to deliver active compositions of the present invention to a site of microorganism infection. The route of administration is preferably designed to obtain direct contact of the pharmaceutical compositions with the infecting microorganisms. Alternatively, administration may be by orthotopic, intradermal, subcutaneous, intramuscular or intraperitoneal injection. The active compounds may also be administered parenterally or intraperitonealy. Such compositions would normally be administered as pharmaceutically acceptable compositions.

The use of such media and agents for pharmaceutically active substances is well known in the art. Except insofar as any conventional media or agent is incompatible with the emulsions of the present invention, their use in therapeutic compositions is contemplated. Supplementary active ingredients also can be incorporated into the compositions.

For topical applications, the pharmaceutically acceptable carrier may take the form of a liquid, cream, foam, lotion, or gel, and may additionally comprise organic solvents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration.

Tablet dosage forms in which the emulsions are formulated for oral or topical administration include liquid capsules, and suppositories. In solid dosage forms for oral administration, the compositions may be admixed with at least one inert diluent such as sucrose, lactose, or starch, and may additionally comprise lubricating agents, buffering agents, enteric coatings, and other components well known to those skilled in the art.

In another embodiment of the invention, the compositions of the invention may be specifically designed for in vitro applications, such as disinfecting or sterilization of medical devices, contact lenses and the like, particularly when the devices or lenses are intended to be used in contact with a patient or wearer. For applications of this type, the compositions may be conveniently provided in the form of a liquid or foam, and may be provided with emulsifiers, surfactants, buffering agents, wetting agents, preservatives, and other components commonly found in compositions of this type.

Compositions of the invention may be impregnated into absorptive materials, such as sutures, bandages, and gauze, or coated onto the surface of solid phase materials, such as staples, zippers and catheters to deliver the compositions to a site for the prevention of microbial infection. Other delivery systems of this type will be readily apparent to those skilled in the art.

In yet another embodiment, the emulsions can be used in the personal health care industry in deodorants, soaps, acne/dermatophyte treatment agents, treatments for halitosis, treatments for vaginal yeast infections, etc. The emulsions can also be used to treat other internal and external microbial infections (such as influenza, H. simplex, etc.). In these applications, the emulsions can be formulated with therapeutic carriers as described above.

Actual amounts of emulsions and enhancing agents in the compositions of the invention may be varied so as to obtain amounts of emulsion and enhancing agents at the site of treatment which are effective in killing vegetative as well as sporular microorganisms and neutralizing their toxic products. Accordingly, the selected amounts will depend on the nature and site for treatment, the desired response, the desired duration of biocidal action and other factors. Generally, the emulsion compositions of the invention will comprise at least 0.001% to 100%, preferably 0.01 to 90%, of emulsion per ml of liquid composition. It is envisioned that viral infections may be treated using between about 0.01% to 100% of emulsion per ml of liquid composition. Bacterial infections may be attacked with compositions comprising between about 0.001% to about 100% of emulsion per ml of liquid composition. Spores can be killed by emulsions comprising from about 0.001% to about 100% of emulsion per ml of liquid composition. These are merely exemplary ranges. It is envisioned that the formulations may comprise about 0.001%, about 0.0025%, about 0.005%, about 0.0075%, about 0.01%, about 0.025%, about 0.05%, about 0.075%, about 0.1%, about 0.25%, about 0.5%, about 1.0%, about 2.5%, about 5%, about 7.5%, about 10%, about 12.5%, about 15%, about 20%, about 25%, about 30%, about 35%, about 40%, about 50%, about 55%, about 60%, about 65%, about 70%, about 75%, about 80%, about 85%, about 90%, about 95% or about 100% of emulsion per ml of liquid composition. It should be understood that a range between any two figures listed above is specifically contemplated to be encompassed within the metes and bounds of the present invention. Some variation in dosage will necessarily occur depending on the condition of the subject being treated.

The person responsible for administration will, in any event, determine the appropriate dose for the individual subject. Moreover, for human administration, preparations should meet sterility, pyrogenicity, general safety and purity standards as required by the FDA Office of Biologics standards.

Combination Therapy

In certain embodiments, the antimicrobial compositions and methods of the present invention also include a variety of combination therapies. It is known in the art that often single antimicrobial agents are much less effective at inhibiting microbes than are several agents employed in conjunction with each other. This approach is often advantageous in avoiding the problems encountered as a result of multidrug resistance. This is particularly prevalent in bacteria that have drug transporters that mediate the efflux of drugs from the organism. The present invention further contemplates the use of the present methods and compositions in such combination therapies.

There are an enormous amount of antimicrobial agents currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al, 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g. chloramphenicol, the tetracyclines, erthromycin and clindamycin); agents that alter protein synthesis and lead to cell death (e.g. aminoglycosides); agents that affect nucleic acid metabolism (e.g. the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

The therapeutic agents of the present invention may be advantageously administered in the form of topical emulsions, injectable compositions and the like. Indeed, in some embodiments, the compositions of the present invention may further comprise various antimicrobial agents described above. A typical composition for such purpose comprises a pharmaceutically acceptable carrier. When the route is topical, the form may be a cream, ointment, salve or spray.

V) Foods

The present invention also contemplates that the fusigenic and lysogenic emulsions described herein may be employed in the food industry in preventing and treating food contaminated with food born bacteria, fungi and toxins. Thus, such compositions may be employed to reduce or inhibit microbial growth or otherwise abrogate the deleterious effects of microbial contamination of food. For these applications, the emulsion compositions are applied in food industry acceptable forms such as additives, preservatives or seasonings.

The use of media and agents for additives, preservatives and seasonings which are acceptable in food industry is well known in the art.

The phrase acceptable in food industry refers to compositions that do not produce adverse, allergic, or other untoward reactions when taken orally by humans or animals. As used herein, "acceptable in food industry media" includes any and all solvents, dispersion substances, any and all spices and herbs and their extracts. The use of such media and agents in food industry is well known in the art. Except insofar as any conventional additives, preservatives and seasonings are incompatible with the emulsions of the present invention, their use in preventing or treating food born microbes and their toxic products is contemplated.

Supplementary active ingredients may also be incorporated into the compositions. For such applications, acceptable carriers may take the form of liquids, creams, foams, gels and may additionally comprise solvents, emulsifiers, gelling agents, moisturizers, stabilizers, wetting agents, preservatives, sequestering agents, dyes, perfumes and other components commonly employed in food processing industry.

In another embodiment of the invention, the compositions of the invention may be specifically designed for applications such as disinfecting or sterilization of any food industry devices and equipment and areas where food is processed, packaged and stored. For applications of this type, the compositions of the emulsions may be conveniently provided in the form of a liquid or foam, and may be provided with emulsifiers, surfactants, buffering agents, wetting agents, preservatives, and other components commonly found in compositions of this type. Compositions of the invention may be impregnated into absorptive materials commonly used in packaging material for the prevention of food contamination during transport and storage. Other delivery systems of this type will be readily apparent to those skilled in the art.

Actual amounts of the emulsions and enhancing agents in the compositions of the invention may be varied so as to obtain appropriate concentrations of emulsion and enhancing agents to effectively prevent or inhibit food contamination caused by food born microbes and their toxic products. Accordingly, the selected concentrations will depend on the nature of the food product, packaging, storage procedure and other factors. Generally, the emulsion compositions of the invention will comprise at least 0.01% to about 90% of emulsion in liquid composition. It is envisioned that the formulations may comprise about 0.001%, about 0.0025%, about 0.005%, about 0.0075%, about 0.01%, about 0.025%, about 0.05%, about 0.075%, about 0.1%, about 0.25%, about 0.5%, about 1.0%, about 2.5%, about 5%, about 7.5%, about 10%, about 12.5%, about 15%, about 20%, about 25%, about 30%, about 35%, about 40%, about 50%, about 55%, about 60%, about 65%, about 70%, about 75%, about 80%, about 85%, about 90%, about 95% or about 100% of emulsion per ml of liquid composition. It should be understood that a range between any two figures listed above is specifically contemplated to be encompassed within the metes and bounds of the present invention.

In particular embodiments, emulsions can be used as disinfectants and detergents to decontaminate and prevent microbial infection of food, soil and water, machinery and other equipment, and animals.

The inventive emulsions can be used by the food industry to prevent contamination. For example, inclusion of the emulsion within the food product itself would be effective in killing bacteria that may have been accidentally contaminated meat or poultry. This could also allow the industry to use a potentially broader spectrum of food products and reduce costs.

Certain embodiments of the present invention can also be used in the beverage industry. For example, the inventive emulsions could be included in juice products to prevent growth of certain fungi, which cause contamination and lead to production of mycotoxins, which are dangerous to consumers. Through the addition of small amounts of the inventive emulsions, the most common fungal contaminants in fruit juice were prevented. This effect was achieved with as little as one part in 10,000 of the emulsion (an amount which did not alter the flavor or the composition of the juice product).

The inventive emulsions can be used to essentially remove infectious agents on machinery and other equipment. For example, the emulsions can be used to eliminate contaminations in meat processing plants, particularly of organisms such as *Listeria monocytogenes*, by cleaning slaughterhouses or food packaging facilities on a continual basis with the emulsion. In addition, the inventive emulsions can be formulated into sprays for hospital and household uses such as cleaning and disinfecting medical devices and patient rooms, household appliances, kitchen and bath surfaces, etc.

The person responsible for administration will, in any event, determine the appropriate dose for individual application. Moreover, said above application should meet general safety and purity standards as required by the FDA office.

VI) Interaction and Germination Enhancers

In specific embodiments, the present invention provides compositions with improved properties of inhibiting the growth of Gram negative bacteria and of bacterial spores further comprising interaction and/or germination enhancing compounds. These embodiments are described in further detail herein below.

Interaction Enhancers

In particular embodiments, it has been ascertained that using the emulsion in combination with a compound capable of increasing the interaction of the emulsion with the cell wall of Gram negative bacteria. In a specific embodiment, the bacteria-inactivating emulsion is premixed with a compound capable of increasing the interaction of the emulsion with the cell wall, however, it should be understood that the interaction enhancer may be provided in combination with the emulsion but in a distinct formulation.

In certain preferred embodiments, the interaction enhancing compound is a chelating agent (e.g., ethylenediaminetetraacetic acid [EDTA]) in tris buffer. Of course, it in understood that any agent that increases the interaction of the bacterial cell wall with the emulsions of the present invention will be useful in the present invention. One of skill in the art will readily be able to determine whether a particular agent has the desired function of acting as an interaction enhancer by applying such an agent to a bacterial composition in combination with the emulsion and comparing the effects of the emulsion in the presence and absence of the interaction enhancer. Any agent that increases the interaction and thereby decrease or inhibits the growth or infectivity of the bacteria in comparison to that parameter in its absence will be considered an interaction enhancer. Given the teachings of the present invention, such monitoring should be possible in vitro and in vivo by routine experimentation.

Germination Enhancers

In specific embodiments, it has been demonstrated that the emulsions of the present invention have sporicidal activity. As discussed above, it is believed that the fusigenic component of the emulsion acts to initiate germination and before reversion to the vegetative form is complete the lysogenic component of the emulsion acts to lyse the newly germinating spore. These components of the emulsion thus act in concert to leave the spore susceptible to disruption by the emulsions. In specific embodiments, compositions are contemplated in which the emulsion further comprise a component that acts to enhance germination. Such a germination enhancer acts to speed up the rate at which the sporicidal activity occurs.

Germination of bacterial endospores and fungal spores is associated with increased metabolism and decreased resistance to heat and chemical reactants. For germination to occur, the spore must sense that the environment is adequate to support vegetation and reproduction. The amino acid L-alanine is reported to stimulate bacterial spore germination (Hills, 1950; Halvorson and Church, 1957). L-alanine and L-proline have also been reported to initiate fungal spore germination (Yanagita, 1957).

Simple α-amino acids, such as glycine and L-alanine, occupy a central position in metabolism. Transamination or deamination of α-amino acids yields the glycogenic or ketogenic carbohydrates and the nitrogen needed for metabolism and growth. For example, transamination or deamination of L-alanine yields pyruvate which is the end product of glycolytic metabolism (Embden-Meyerhof-Pamas Pathway). Oxidation of pyruvate by pyruvate dehydrogenase complex yields acetyl-CoA, NADH, $H^+$, and $CO_2$. Acetyl-CoA is the initiator substrate for the tricarboxylic acid cycle (Kreb's Cycle) which in turns feeds the mitochondrial electron transport chain. Acetyl-CoA is also the ultimate carbon source for fatty acid synthesis as well as for sterol synthesis. Simple α-amino acids can provide the nitrogen, $CO_2$, glycogenic and/or ketogenic equivalents required for germination and the metabolic activity that follows.

Representative germination enhancing agents of the invention include, but are not limited to, α-amino acids including glycine and the L-enantiomers of alanine, valine, leucine, isoleucine, serine, threonine, lysine, phenylalanine, tyrosine, and the alkyl esters thereof. Additional information on the effects of amino acids on germination may be found in U.S. Pat. No. 5,510,104 (herein incorporated by reference in its entirety). In some embodiments, a mixture of glucose, fructose, asparagine, NaCl, $NH_4Cl$, $CaCl_2$, and KCl also may be an effective germination enhancer. In particularly preferred embodiments of the present invention, the formulation comprises the germination enhancers L-alanine, $CaCl_2$, inosine and $NH_4Cl$. Of course, these are merely exemplary germination enhancers and it is understood that germination enhancer commonly used in the art will also be useful in the compositions of the present invention.

VII) Kits

In other embodiments of the present invention, the methods and compositions, or components of the methods and compositions may be formulated in a single formulation, or may be separated into binary formulations for later mixing during use, as may be desired for a particular application. Such components may advantageously be placed in kits for use against microbial infections, decontaminating instruments and the like. In some embodiment, such kits contain all the essential materials and reagents required for the delivery of the formulations of the present invention to the site of their intended action.

In some embodiments, for in vivo use, the methods and compositions of the present invention may be formulated into a single or separate pharmaceutically acceptable syringeable composition. In this case, the container means may itself be an inhalant, syringe, pipette, eye dropper, or other like apparatus, from which the formulation may be applied to an infected area of the body, such as the lungs, injected into an animal, or even applied to and mixed with the other components of the kit.

The kits of the present invention also typically include a means for containing the vials in close confinement for commercial sale (e.g., injection or blow-molded plastic containers into which the desired vials are retained). Irrespective of the number or type of containers, the kits of the invention also may comprise, or be packaged with, an instrument for assisting with the injection/ad ministration or placement of the ultimate complex composition within the body of an animal. Such an instrument may be an inhalant, syringe, pipette, forceps, measured spoon, eyedropper or any such medically approved delivery vehicle.

VIII) EXAMPLE

The following examples serve to illustrate certain preferred embodiments and aspects of the present invention and are not to be construed as limiting the scope thereof.

In the experimental disclosure which follows, the following abbreviations apply: eq (equivalents); $\mu$ (micron); M (Molar); $\mu$M (micromolar); mM (millimolar); N (Normal); mol (moles); mmol (millimoles); $\mu$mol (micromoles); nmol (nanomoles); g (grams); mg (milligrams); $\mu$g (micrograms); ng (nanograms); L (liters); ml (milliliters); $\mu$l (microliters); cm (centimeters); mm (millimeters); $\mu$m (micrometers); nM (nanomolar); ° C. (degrees Centigrade); and PBS (phosphate buffered saline).

Example 1

Methods of Formulating Emulsions

The emulsion is produced as follows: an oil phase is made by blending organic solvent, oil, and surfactant and then heating the resulting mixture at 37–90° C. for up to one hour. The emulsion is formed either with a reciprocating syringe instrumentation or Silverson high sheer mixer. The water phase is added to the oil phase and mixed for 1–30 minutes, preferably for 5 minutes. For emulsions containing volatile ingredients, the volatile ingredients are added along with the aqueous phase.

In a particular embodiment, the emulsion was formed as follows: an oil phase was made by blending tri-butyl phosphate, soybean oil, and a surfactant (e.g., Triton X-100) and then heating the resulting mixture at 86° C. for one hour. An emulsion was then produced by injecting water into the oil phase at a volume/volume ratio of one part oil phase to four parts water. The emulsion can be produced manually, with reciprocating syringe instrumentation, or with batch or continuous flow instrumentation. Methods of producing these emulsions are well known to those of skill in the art and are described in e.g., U.S. Pat. Nos. 5,103,497; and 4,895,452, (herein incorporated by reference in their entireties). Table 2 shows the proportions of each component, the pH, and the size of the emulsion as measured on a Coulter LS 130 laser sizing instrument equipped with a circulating water bath.

TABLE 2

| Chemical Components of Emulsion | Percentage of Each Component | pH | Mean Coulter Size (in Microns) | Mean Coulter Range (in Microns) |
|---|---|---|---|---|
| BCTP | | | | |
| Triton X-100 | 2% | | | |
| Tributyl phosphate | 2% | 5.16 | 1.074 | 0.758–1.428 |
| Oil (ex. Soy bean) | 16% | | | |
| Water | 80% | | | |
| BCTP 0.1* | | | | |
| Triton X-100 | 0.20% | 5.37 | 0.944 | 0.625–1.333 |
| Tributyl phosphate | 0.20% | | | |
| Oil (ex. Soy bean) | 1.60% | | | |
| Water | 98% | | | |

*This emulsion was obtained by diluting the BCTP emulsion with water in a ratio of 1:9

The emulsions of the present invention are highly stable. Indeed, emulsions were produced as described above and allowed to stand overnight at room temperature in sealed 50 to 1000 mL polypropylene tubes. The emulsions were then monitored for signs of separation. Emulsions that showed no signs of separation were considered "stable." Stable emulsions were then monitored over 1 year and were found to maintain stability.

Emulsions were again produced as described above and allowed to stand overnight at −20° C. in sealed 50 mL polypropylene tubes. The emulsions were then monitored for signs of separation. Emulsions that showed no signs of separation were considered "stable." The BCTP and BCTP 0.1, emulsions have been found to be substantially unchanged after storage at room temperature for at least 24 months.

Example 2

Characterization Of An Exemplary Bacteria-inactivating Emulsion Of The Present Invention As An Emulsified Liposome Formed In Lipid Droplets A bacteria inactivating emulsion of the present invention, designated Novaclor 401, was formed by mixing a lipid-containing oil-in-water emulsion with BCTP. In particular, a lipid-containing oil-in-water emulsion having glycerol monooleate (GMO) as the primary lipid and cetylpyridinium chloride (CPC) as a positive charge producing agent (referred to herein as GMO/CPC lipid emulsion or "P10") and BCTP were mixed in a 1:1 (volume to volume) ratio. U.S. Pat. No. 5,547,677 (herein incorporated by reference in its entirety), describes the GMO/CPC lipid emulsion and other related lipid emulsions that may be combined with BCTP to provide the bacteria-inactivating oil-in-water emulsions of the present invention.

Example 3

In Vitro Bactericidal Efficacy Study I—Gram Positive Bacteria

In order to study the bactericidal efficacy of the emulsions of the present invention, the emulsions were mixed with various bacteria for 10 minutes and then plated on standard microbiological media at varying dilutions. Colony counts were then compared to untreated cultures to determine the percent of bacteria killed by the treatment. Table 3 summarizes the results of the experiment.

TABLE 3

| Organism | Inoculum (CFU) | % Killing | Emulsion Tested |
|---|---|---|---|
| Vibrio cholerae classical | $1.3 \times 10^8$ | 100 | BCTP |
| Vibrio cholerae Eltor | $5.1 \times 10^8$ | 100 | BCTP |
| Vibtio parahemolytica | $4.0 \times 10^7$ | 98–100 | BCTP |

In order to study the bactericidal effect of the emulsions of the present invention on various vegetative forms of Bacillus species, an emulsion at three dilutions was mixed with four Bacillus species for 10 minutes and then plated on microbiological medium. Colony counts were then compared with untreated cultures to determine the percent of bacteria killed by the treatment. Table 4 contains a summary of the bactericidal results from several experiments with the mean percentage kill in parenthesis.

TABLE 4

| BCTP/ Dilution | B. cerous | B. circulans | B. megaterium | B. subtilus |
|---|---|---|---|---|
| 1:10 | 99% (99%) | 95–99% (97%) | 99% (99%) | 99% (99%) |
| 1:100 | 97–99% (98%) | 74–93% (84%) | 96–97% (96%) | 99% (99%) |
| 1:1000 | 0% (0%) | 45–60% (52%) | 0–32% (16%) | 0–39% (20%) |

Example 4

In Vitro Bactericidal Efficacy Study II—Gram Negative Bacteria

To increase the uptake of the bacteria inactivating emulsions by the cell walls of Gram negative bacteria, thereby enhancing the microbicidal effect of the emulsions on the resistant Gram negative bacteria, EDTA (ethylenediaminetetraacetic acid) was premixed with the emulsions. The EDTA was used in low concentration (50–25 $\mu$M) and the mix was incubated with the various Gram negative bacteria for 15 minutes. The microbicidal effect of the mix was then measured on Trypticase soy broth. The results are set forth in Table 5 below. There was over 99% reduction of the bacterial count using BCTP in 1/100 dilutions. This reduction of count was not due to the killing effect of EDTA alone as shown from the control group in which 250 $\mu$M of EDTA alone could not reduce the bacterial count in 15 minutes.

TABLE 5

| Bacterium | Bacteria alone (CFU) | Bacteria + BCTP (CFU) | Bacteria + BCTP + EDTA (CFU) | Bacteria + EDTA (CFU) |
|---|---|---|---|---|
| S. typhimunium | 1,830,000 | 1,370,000 | 40 | 790,000 |
| S. dysenteriae | 910,000 | 690,000 | 0 | 320,000 |

Example 5

In Vitro Bactericidal Efficacy Study III—Vegetative And Spore Forms

Bacillus cereus (B. cereus, ATCC #14579) was utilized as a model system for Bacillus anthracis. Experiments with BCTP diluted preparations to study the bactericidal effect of the compounds of the present invention on the vegetative form (actively growing) of B. cereus were performed. Treatment in medium for 10 minutes at 37° C. was evaluated. As summarized in Table 6, the BCTP emulsion is efficacious against the vegetative form of B. cereus. A 10 minute exposure with this preparation is sufficient for virtually complete killing of vegetative forms of B. cereus at all concentrations tested including dilutions as high as 1:100.

TABLE 6

| Emulsion | Undiluted | 1:10 | 1:100 |
|---|---|---|---|
| BCTP | >99% Avg = >99% | >99% Avg = >99% | 59 - >99% Avg = 82% |

Number of experiments = 4

The spore form of B. anthracis is one of the most likely organisms to be used as a biological weapon. Spores are well known to be highly resistant to most disinfectants. As describe above, effective killing of spores usually requires the use of toxic and irritating chemicals such as formaldehyde or sodium hypochlorite (i.e., bleach). The same experiment was therefore performed with the spore form of B. cereus. As shown in Table 7, treatment in both medium for 10 minutes at 37° C. was not sufficient to kill B. cereus spores.

TABLE 7

| Emulsion | Undiluted | 1:10 | 1:100 |
|---|---|---|---|
| BCTP | 0%–12% Avg = 6% | 0% Avg = 0% | 0% Avg = 0% |

Number of experiments = 2

To evaluate the efficacy of the compounds of the present invention on the spore form of B. cereus over a period of time, BCTP was incorporated into solid agar medium at 1:100 dilution and the spores spread uniformly on the surface and incubated for 96 hours at 37° C. No growth occurred on solid agar medium wherein BCTP had been incorporated, out to 96 hours (i.e., >99% killing, average >99% killing, 3 experiments).

Figure 1:
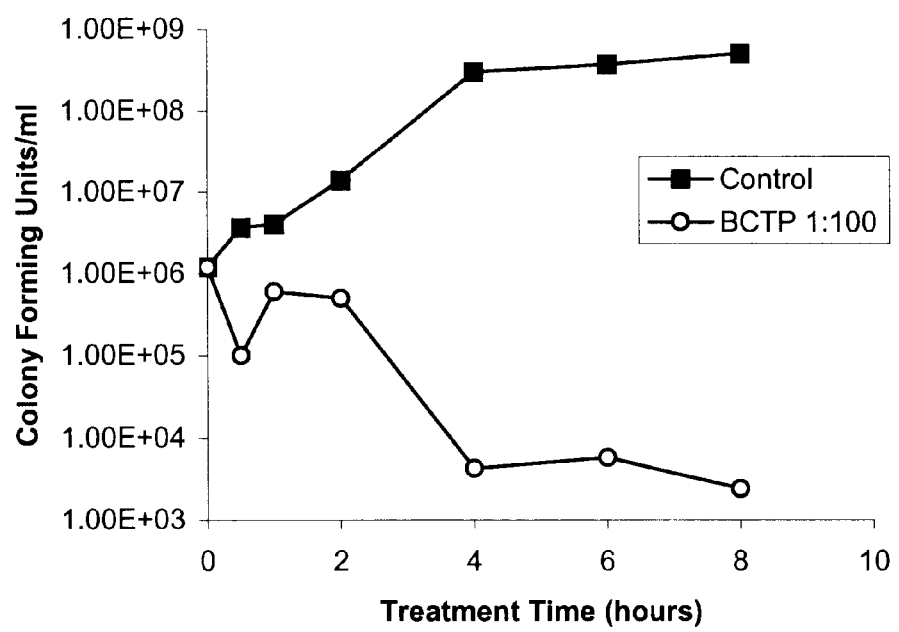
FIG. 1 illustrates the bactericidal efficacy of an emulsion of the present invention on *B. cereus* spores.

In an attempt to more closely define the time at which killing of spores by BCTP occurred, the following experiment was performed. Briefly, a spore preparation was treated with BCTP at a dilution of 1:100 and compared to an untreated control. The number of colony forming units per milliliter (CFU/ml) was quantitated after 0.5, 1, 2, 4, 6, and 8 hours. As shown in FIG. 1, CFU/ml in the untreated control increased over the first 4 hours of incubation and then reached a plateau. Bacterial smears prepared at time zero, 1, 2, 4 and 6 hours, and stained for spore structures, revealed that by 2 hours no spore structures remained (FIGS. 2A–2C). Thus, 100% germination of spores occurred in the untreated control by the 2 hour time point. In the spore preparation treated with BCTP, CFU/ml showed no increase over the first 2 hours and then declined rapidly over the time period from 2–4 hours. The decline from baseline CFU/ml over 2–4 hours was approximately 1000-fold. Bacterial smears prepared at the same time points and stained for spore structures revealed that spore structures remained to the end of the experiment at 8 hours. Hence, germination of spores did not occur in the BCTP treated culture due to either inhibition of the germination process or because the spores were damaged and unable to germinate. In order to determine whether the emulsions were effective in killing other Bacillus species in addition to B. cereus, a similar experiment was performed as described above, wherein spore preparations were treated with emulsions and compared to an untreated control after four hours of incubation. The following Table 8 shows the results wherein the numbers represent the mean sporicidal activity from several experiments.

TABLE 8

| BCTP/ Dilution | B. cereus | B. circulans | B. megaterium | B. subtlius |
|---|---|---|---|---|
| 1:10 | 82% | 61% | 93% | 31% |
| 1:100 | 91% | 80% | 92% | 39% |
| 1:1000 | 47% | 73% | 94% | 22% |

Example 6

In Vivo Bactericidal Efficacy Study

Animal studies were preformed to demonstrate the protective and therapeutic effect of the inventive emulsions in vivo. *Bacillus cereus* infection in experimental animals has been used previously as a model system for the study of anthrax (Burdon and Wende, 1960; Burdon et al., 1967; Lamanna and Jones, 1963). The disease syndrome induced in animals experimentally infected with *B. cereusis* in some respects similar to anthrax (Drobniewski, 1993; Fritz et aL, 1995). The inventive emulsions were mixed with *B. cereus* spores before injecting into mice.

Irrigation of Skin Wounds

A 1 cm skin wound was infected with $2.5 \times 10^7$ *B. cereus* spores then closed without any further treatment. The other groups were infected with the same number of spores. One hour later, the wounds were irrigated with either inventive emulsion or saline to simulate post-exposure decontamination. By 48 hours, there were large necrotic areas surrounding the wounds with an average area of 4.86 $cm^2$. In addition, 60% of the animals in this group died as a result of the infection. Histology of these lesions indicated total necrosis of the dernis and subdermis and large numbers of vegetative Bacillus organisms. Irrigation of experimentally infected wounds with saline did not result in any apparent benefit.

Irrigation of wounds infected with *B. cereus* spores with inventive emulsion showed substantial benefit, resulting in a consistent 98% reduction in the lesion size from 4.86 $cm^2$ to 0.06 $cm^2$. This reduction in lesion size was accompanied by a three-fold reduction in mortality (60% to 20%) when compared to experimental animals receiving either no treatment or saline irrigation. Histology of these lesions showed no evidence of vegetative Bacillus organisms and minimal disruption of the epidermis (Hamouda et al., 1999).

Subcutaneous Injection

CD-1 mice were injected with inventive emulsion diluted 1:10 in saline as a control and did not exhibit signs of distress or inflammatory reaction, either in gross or histological analysis. To test the pathogenic effect of *B. cereus* spores in vivo and the sporicidal effect of inventive emulsion, a suspension of $4 \times 10^7$ *B. cereus* spores was mixed with saline or with inventive emulsion at a final dilution of 1:10 and then immediately injected subcutaneously into the back of CD-1 mice.

Mice that were infected subcutaneously with *B. cereus* spores without inventive emulsion developed severe edema at 6–8 hours. This was followed by a gray, necrotic area surrounding the injection site at 18–24 hours, with severe sloughing of the skin present by 48 hours, leaving a dry, red-colored lesion.

Simultaneous injection of spores and inventive emulsion resulted in a greater than 98% reduction in the size of the necrotic lesion from 1.68 $cm^2$ to 0.02 $cm^2$ when the spores were premixed with inventive emulsion. This was associated with minimal edema or inflammation (Hamouda et al., 1999).

Rabbit Cornea

The cornea of rabbits were irrigated with various concentrations of the inventive emulsions and monitored at 24 and 48 hours. No irritations or abnormalities were observed when compositions were used in therapeutic amounts.

Mucous Membrane

Intranasal toxicity was preformed in mice by installation of 25 $\mu$L of 4% of the nanoemulsion per nare. No clinical or histopathological changes were observed in these mice.

Oral toxicity testing in rats was performed by gavaging up to 8 mL per kg of 25% nanoemulsion. The rats did not lose weight or show signs of toxicity either clinically or histopathologically. There were no observed changes in the gut bacterial flora as a result of oral administration of the emulsions.

In a particular embodiment, *Bacillus cereus* was passed three times on blood agar (TSA with 5% sheep blood, REMEL). *B. cereus* was scraped from the third passage plate and resuspended in Trypticase soy broth (TSB) (available from BBL). The *B. cereus* suspension was divided into two tubes. An equal volume of sterile saline was added to one tube and mixed 0.1 cc of the *B. cereus* suspension/saline was injected subcutaneously into 5 CD-1 mice. An equal volume of BCTP (diluted 1:5 in sterile saline) was added to one tube and mixed, giving a final dilution of BCTP at 1:10. The *B. cereus* suspension/BCTP was incubated at 37° C. for 10 minutes while being mixed 0.1 cc of the *B. cereus* suspension/BCTP was injected subcutaneously into 5 CD-1 mice. Equal volumes of BCTP (diluted 1:5 in sterile saline) and TSB were mixed, giving a final dilution of BCTP at 1:10. 0.1 cc of the BCTP/TSB was injected subcutaneously into 5 CD-1 mice.

The number of colony forming units (cfu) of *B. cereus* in the inocula were quantitated as follows: 10-fold serial dilutions of the *B. cereus* and *B. cereus*/BCTP suspensions were made in distilled $H_2O$. Duplicate plates of TSA were inoculated from each dilution (10 $\mu$l per plate). The TSA plates were incubated overnight at 37° C. Colony counts were made and the number of cfu/cc was calculated. Necrotic lesions appears to be smaller in mice which were inoculated with *B. cereus* which was pretreated with BCTP. The following Table 9 shows the results of the experiment.

TABLE 9

| Inoculum | ID# | Observation (24 hours) |
|---|---|---|
| *B. cereus* | 1528 | necrosis at injection site |
| $3.1 \times 10^7$ | 1529 | site |
| cfu/mouse | 1530 | necrosis at injection site |
| | 1531 | site |
| | 1532 | dead |
| | | dead |
| | | necrosis at injection site |
| *B. cereus* | 1348 | necrosis at injection site |
| $8.0 \times 10^5$ | 1349 | site |
| cfu/mouse | 1360 | no reaction |
| (BCTP treated) | 1526 | no reaction |
| | 1527 | necrosis at injection site |
| | | necrosis at injection site |
| BCTP/TSB | 1326 | no reaction |
| | 1400 | no reaction |
| | 1375 | no reaction |
| | 1346 | no reaction |
| | 1347 | no reaction |

*Bacillus cereus* was grown on Nutrient Agar (Difco) with 0.1% Yeast Extract (Difco) and 50 $\mu$g/ml $MnSO_4$ for induction of spore formation. The plate was scraped and suspended in sterile 50% ethanol and incubated at room temperature for 2 hours with agitation in order to lyse remaining vegetation bacteria. The suspension was centrifuged at 2,500×g for 20 minutes and the supernatant discarded. The pellet was resuspended in di$H_2O$, centrifuged at 2,500×g for 20 minutes, and the supernatant discarded. The spore suspension was divided. The pellet was resuspended into TSB. 0.1 cc of the *B. cereus* spore suspension diluted 1:2 with saline was injected subcutanneously into 3 CD-1 mice. Equal volumes of BCTP (diluted 1:5 in sterile saline) and *B. cereus* spore suspension were mixed, giving a final dilution of BCTP at 1:10 (preincubation time). 0.1 cc of the BCTP/*B. cereus* spore suspension was injected suncutaneously into 3 CD-1 mice. The number of colony forming units (cfu) of *B. cereus* in the inoculum was quantitated as follows. 10-fold serial dilutions of the *B. cereus* and *B. cereus*/BCTP suspensions were made in distilled $H_2O$. Duplicate plates of TSA were inoculated from each dilusion (10 $\mu$l per plate).

The TSA plates were incubated overnight at 37° C. Colony counts were made and the number of cfu/cc was calculated. Necrotic lesions appeared to be smaller in mice which were inoculated with *B. cereus* spores which were pretreated with BCTP. The observations from these studies are shown in Table 10.

TABLE 10

| Inoculum | Observation (24 hours) |
| --- | --- |
| *B. cereus* $6.4 \times 10^6$ spores/mouse | ⅔ (66%) mice exhibited necrosis at injection site |
| *B. cereus* $4.8 \times 10^6$ spores/mouse (BCTP treated) | ⅓ (33%) mice exhibited necrosis at injection site |
| *B. cereus* $4.8 \times 10^6$ vegetative forms/mouse | 3/3 (100%) mice exhibited necrosis at injection site |
| Lysed *B. cereus* $4.8 \times 10^6$ cfu/mouse | 3/3 (100%) mice did not exhibit symptoms |
| BCTP/TSB | ⅓ (33%) mice appeared to have some skin necrosis |

*Bacillus cereus* was grown on Nutrient Agar (Difco) with 0.1% Yeast Extract (Difco) and 50 (g/ml MnSO$_4$ for induction of spore formation). The plate was scraped and suspended in sterile 50% ethanol and incubated at room temperature for 2 hours with agitation in order to lyse remaining vegetative bacteria. The suspension was centrifuged at 2,500×g for 20 minutes and the supernatant discarded. The pellet was resuspended in distilled H$_2$O, centrifuged at 2,500×g for 20 minutes, and the supernatant discarded. The pellet was resuspended in TSB. The *B. cereus* spore suspension was divided into three tubes. An equal volume of sterile saline was added to one tube and mixed. 0.1 cc of the *B. cereus* suspension/saline was injected subcutaneously into 10 CD-1 mice. An equal volume of BCTP (diluted 1:5 in sterile saline) was added to the second tube and mixed, giving a final dilution of BCTP at 1:10. The *B. cereus* spore suspension/BCTP (1:10) was incubated at 37° C. for 4 hours while being mixed. 0.1 cc of the *B. cereus* spore suspension/BCTP (1:10) was injected subcutaneously into 10 CD-1 mice. An equal volume of BCTP (diluted 1:50 in sterile saline) was added to the third tube and mixed, giving a final dilution of BCTP at 1:100. The *B. cereus* spore suspension/BCTP (1:100) was incubated at 37° C. for 4 hours while being mixed. 0.1 cc of the *B. cereus* spore suspension/BCTP (1:100) was injected subcutaneously into 10 CD-1 mice. Equal volumes of BCTP (diluted 1:5 in sterile saline) and TSB were mixed, giving a final dilution of BCTP at 1:10. 0.1 cc of the BCTPFTSB was injected subcutaneously into 10 CD-1 mice. Equal volumes of BCTP (diluted 1:50 in sterile saline) and TSB were mixed, giving a final dilution of BCTP at 1:100. 0.1 cc of the BCTP/TSB was injected subcutaneously into 10 CD-1 mice. The observations form these studies are shown in Table 11 and Table 12.

TABLE 11

| Inoculum sc | ID# | Observation at 24 hours |
| --- | --- | --- |
| *B. cereus* $5.5 \times 10^7$ Spores/mouse No treatment group | 1 | 2.4 cm$^2$ skin lesion with 0.08 cm$^2$ necrotic area |
| | 2 | no abnormalities observed |
| | 3 | Moribund with 8 cm$^2$ skin lesion and hind limb paralysis |
| | 4 | limb paralysis |

TABLE 11-continued

| Inoculum sc | ID# | Observation at 24 hours |
| --- | --- | --- |
| | 5 | 3.52 cm$^2$ skin lesion |
| | 6 | 1.44 cm$^2$ skin lesion |
| | 7 | 3.4 cm$^2$ skin lesion |
| | 8 | 5.5 cm$^2$ skin lesion |
| | 9 | 5.5 cm$^2$ skin lesion |
| | 10 | 3.3 cm$^2$ skin lesion with 0.72 cm$^2$ necrotic area |
| | | 2.64 cm$^2$ skin lesion with two necrotic areas (0.33 cm$^2$ and 0.1 cm$^2$) Mean lesion size in Spore group alone 3.97 cm$^2$ (¹⁰⁄₁₀ (10%) with no abnormalities observed) |

Note:
Skin lesions grey in color with edema, necrotic areas red/dry.

TABLE 12

| Inoculum sc | ID # | Observation at 24 hours |
| --- | --- | --- |
| *B. cereus* $2.8 \times 10^7$ spores/mouse in the BCTP 1:10 treated group | 41 | no abnormalities observed |
| | 42 | no abnormalities observed |
| | 43 | 1.2 cm$^2$ white skin lesion with grey center, slight edema |
| | 44 | 0.78 cm$^2$ white skin lesion |
| | 45 | 0.13 cm$^2$ white skin lesion |
| | 46 | 2.2 cm$^2$ white skin lesion |
| | 47 | 1.8 cm$^2$ white skin lesion with 0.1 cm$^2$ brown area in center |
| | 48 | 1 cm$^2$ white skin lesion with grey center |
| | 49 | 0.78 cm$^2$ white skin lesion |
| | 50 | no abnormalities observed Mean lesion size in BCTP 1:10 treatment group = 1.13 cm$^2$ (³⁄₁₀ (30%) with no abnormalities observed) |
| *B. cereus* $1.8 \times 10^7$ spores/mouse in the BCTP 1:100 treated group | 51 | 2.1 cm3 grey skin lesion |
| | 52 | 0.72 cm$^2$ grey skin lesion |
| | 53 | 1.5 cm$^2$ grey skin lesion |
| | 54 | 1.2 cm$^2$ grey skin lesion |
| | 55 | 3.15 cm$^2$ grey skin lesion |
| | 56 | 0.6 cm$^2$ grey skin lesion |
| | 57 | 0.5 cm$^2$ grey skin lesion |
| | 58 | 2.25 cm$^2$ grey skin lesion |
| | 59 | 4.8 cm$^2$ grey skin lesion with necrotic area 1 cm diameter |
| | 60 | 2.7 cm$^2$ grey skin lesion Mean lesion size In BCTP 1:100 treatment group = 1.9 cm$^2$ (⁰⁄₁₀ (0%) with no abnormalities observed) |
| BCTP 1:10 alone | 11 | 2.6 cm$^2$ white area |
| | 12 | 0.15 cm$^2$ white area |
| | 13 | no abnormalities observed |
| | 14 | 0.15 cm$^2$ white area |
| | 15 | 0.35 cm$^2$ white area |
| | 16 | no abnormalities observed |
| | 17 | 0.12 cm$^2$ white area |
| | 18 | no abnormalities observed |
| | 19 | 0.56 cm$^2$ white area |
| | 20 | 0.3 cm$^2$ white area Mean lesion size In BCTP 1:10 alone group = 0.60 cm$^2$ (³⁄₁₀ (30%) with no abnormalities observed) |
| BCTP 1:100 alone | 21–30 | no abnormalities observed Mean lesion size in BCTP 1:100 alone group = 0 cm$^2$ (¹⁰⁄₁₀ (100%) with no abnormalities observed) |
| TSB alone | 31–40 | no abnormalities observed Mean lesion size In the TSB alone group = 0 cm$^2$ (¹⁰⁄₁₀ (100%) with no abnormalities observed) |

Re-isolation of *B. cereus* was attempted from skin lesions, blood, liver, and spleen (Table 13). Skin lesions were cleansed with betadine followed by 70% sterile isopropyl alcohol. An incision was made at the margin of the lesion and swabbed. The chest was cleansed with betadine followed by 70% sterile isopropyl alcohol. Blood was drawn by cardiac puncture. The abdomen was cleansed with betadine followed by 70% sterile isopropyl alcohol. The skin and abdominal muscles were opened with separate sterile instruments. Samples of liver and spleen were removed using separate sterile instruments. Liver and spleen samples were passed briefly through a flame and cut using sterile instruments. The freshly exposed surface was used for culture. BHI agar (Difco) was inoculated and incubated aerobically at 37° C. overnight.

TABLE 13

Figure 8:
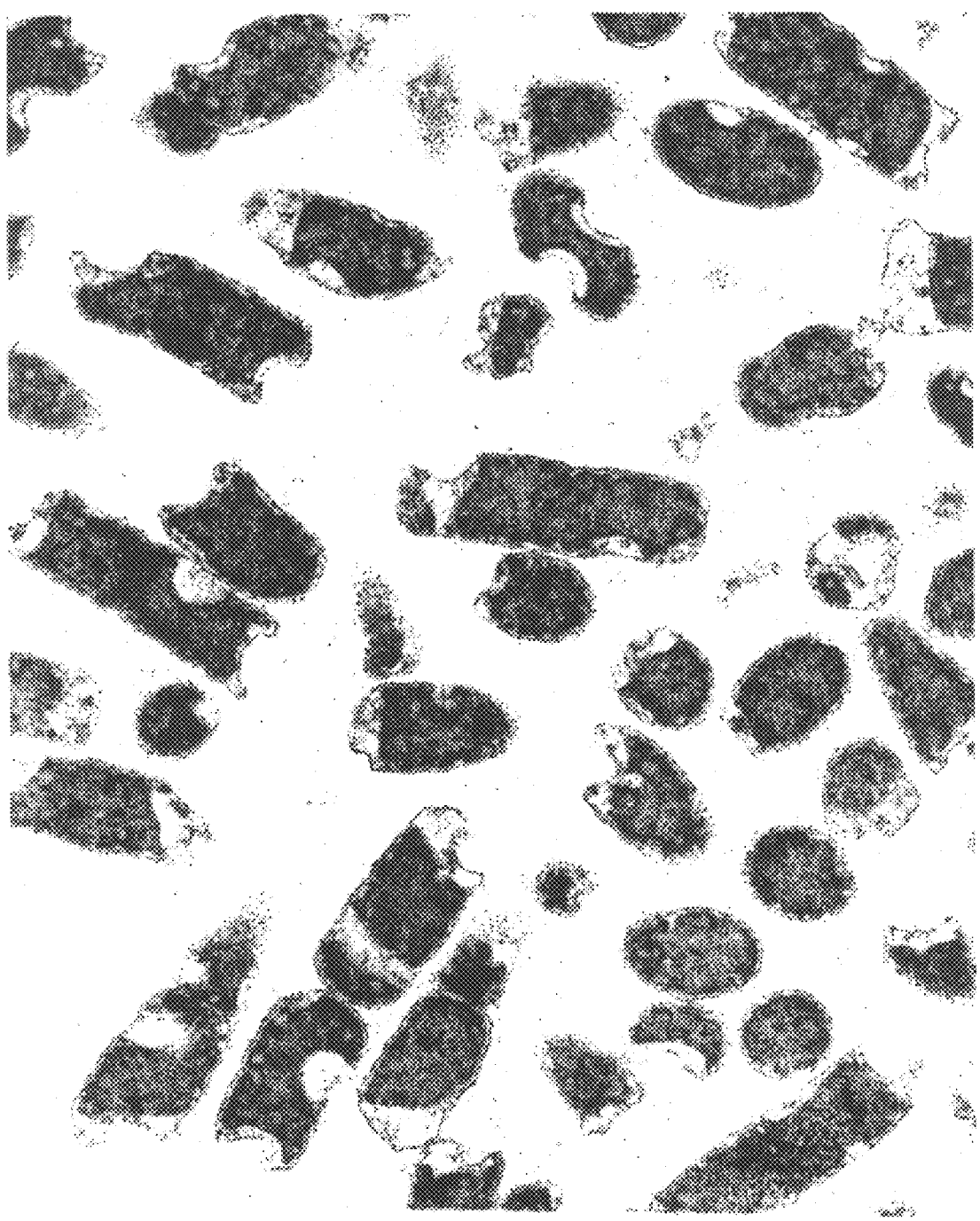
FIG. 8 depicts an electromicrograph of *E. coli* (10,000×).
Figure 9:
FIG. 9 depicts an electromicrograph of *E. coli* treated with BCTP (10,000×).
Figure 10:
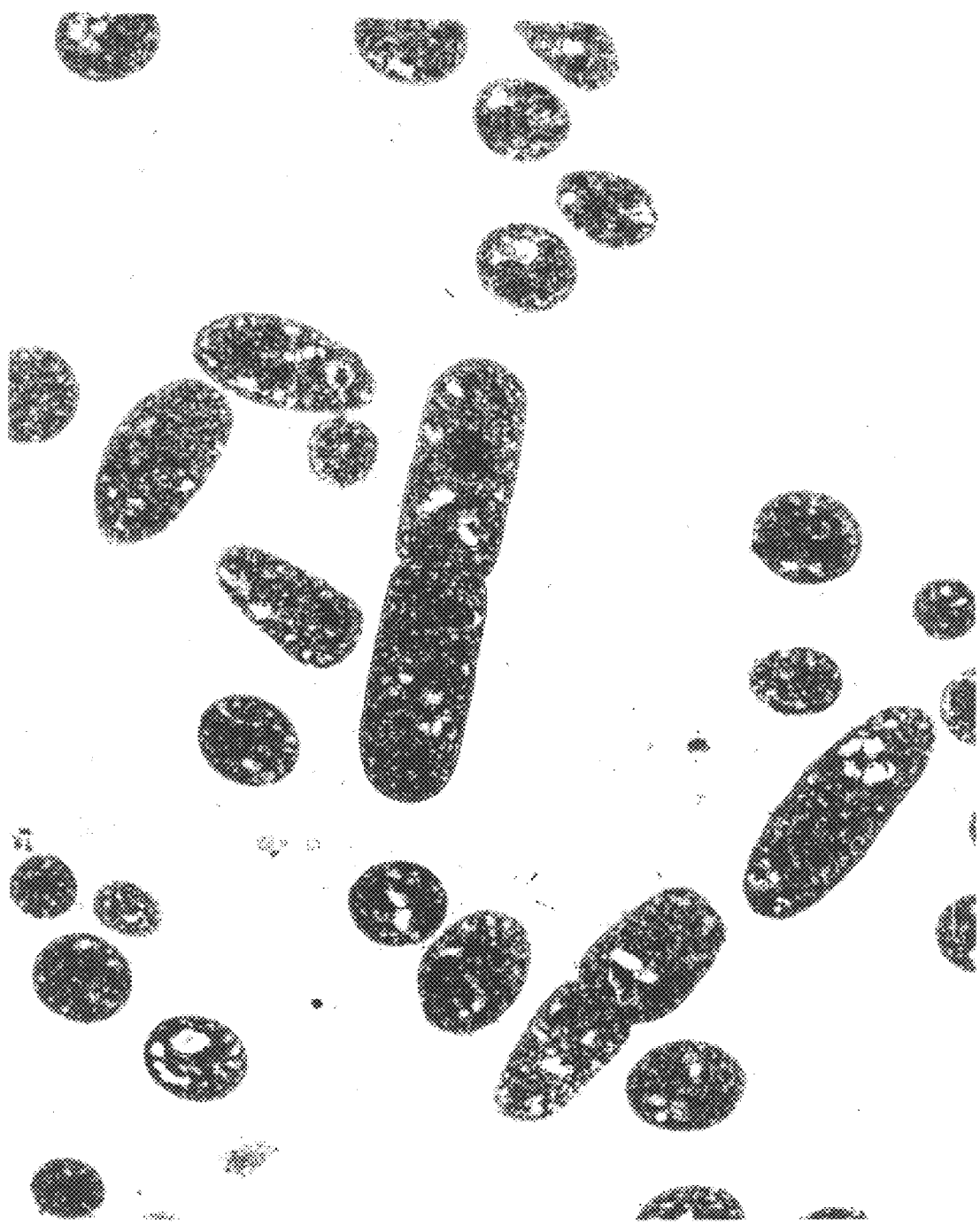
FIG. 10 depicts an electromicrograph of *E. coli* treated with P10 (10,000×).

| Inoculum sc | ID# | Necrospy | *B. cereus* Re-isolation from site of skin lesion |
|---|---|---|---|
| *B. cereus* | 3 | 24 hours | skin lesion >300 cfu |
| $5.5 \times 10^7$ | 6 | 48 hours | skin lesion >300 cfu |
| spores/mouse | 7 | 48 hours | skin lesion >300 cfu |
| in the | 8 | 72 hours | skin lesion 100 cfu |
| Untreated group | 9 | 72 hours | skin lesion 25 cfu |
| | 10 | 72 hours | skin lesion 100 |
| | 1 | 96 hours | skin lesion >300 cfu |
| | 4 | 96 hours | skin lesion >300 cfu |
| | 5 | 96 hours | skin lesion >300 cfu |
| | | | Mean CFU In Untreated Spore group = 214* |
| | | | *(6/9 (67%) > 300 CFU) |
| *B. cereus* | 48 | 48 hours | skin lesion 17 cfu |
| $2.8 \times 10^7$ | 50 | 48 hours | skin lesion >300 cfu |
| spores/mouse | 46 | 72 hours | skin lesion >200 cfu |
| in the | 47 | 72 hours | skin lesion 100 cfu |
| BCTP 1:10 | 49 | 72 hours | skin lesion >300 cfu |
| treated group | 41 | 96 hours | skin lesion >300 cfu |
| | 42* | 96 hours | skin lesion 20 cfu |
| | 43 | | cultures not done |
| | 44 | 96 hours | skin lesion >300 cfu |
| | 45 | | cultures not done |
| | 46 | | cultures not done |
| | | | Mean CFU in BCTP 1:10 group = 192* |
| | | | *(318 (38%) >300 CFU) |
| *B. cereus* | 48 | 48 hours | skin lesion 18 cfu |
| $1.8 \times 10^7$ | 50* | 48 hours | skin lesion >300 cfu |
| spores/mouse | 52 | 72 hours | skin lesion 1 cfu |
| in the | 54 | 72 hours | re-isolation negative |
| BCTP 1:100 | 56 | 72 hours | skin lesion >300 cfu |
| treated group | 58 | 96 hours | skin lesion 173 cfu |
| | 59 | 96 hours | skin lesion 4 cfu |
| | 60 | 96 hours | skin lesion 6 cfu |
| | | | Mean CFU in BCTP 1:100 group = 100 |
| | | | *(2/8 (25%) >00 CFU) |

*Although no lesions were present in these mice, organisms were removed from the injection site.

Pretreatment of both vegetative *B. cereus* and *B. cereus* spores reduce their ability to cause disease symptoms when introduced into experimental animals. This is reflected in the smaller size of skin lesions and the generally lower numbers of *B. cereus* recovered from the lesions. In addition, less frequent re-isolation of *B. cereus* from blood, liver, and spleen occurs suggesting that septicemia may be preventable.

Example 7

In Vivo Toxicity Study I

CD-1 mice were injected subcutaneously with 0.1 cc of the compounds of the present invention and observed for 4 days for signs of inflammation and/or necrosis. Dilutions of the compounds were made in sterile saline. Tissue samples from mice were preserved in 10% neutral buffered formalin for histopathologic examination. Samples of skin and muscle (from mice which were injected with undiluted compounds) sent for histological review were reported to show indications of tissue necrosis. Tissue samples from mice which were injected with diluted compounds were not histologically examined. Tables 14 and 15 show the results of two individual experiments.

TABLE 14

| Compound | Mouse ID # | Dilution | Observation |
|---|---|---|---|
| BCTP | 1326 | undiluted | necrosis |
| | 1327 | undiluted | no reaction |
| | 1328 | 1:10 | no reaction |
| | 1329 | 1:10 | no reaction |
| | 1324 | 1:100 | no reaction |
| | 1331 | 1:100 | no reaction |
| Saline | 1344 | | no reaction |
| | 1345 | | no reaction |

TABLE 15

| Compound | Mouse ID # | Dilution | Observation |
|---|---|---|---|
| BCTP | 1376 | undiluted | necrosis |
| | 1377 | undiluted | minimal necrosis |
| | 1378 | 1:10 | no reaction |
| | 1379 | 1:10 | no reaction |
| | 1380 | 1:100 | no reaction |
| | 1381 | 1:100 | no reaction |
| Saline | 1394 | | no reaction |
| | 1395 | | no reaction |

Guinea pigs were injected intramuscularly (in both hind legs) with 1.0 cc of compounds of the present invention per site and observed for 4 days for signs of inflammation and/or necrosis. Dilutions of the compounds were made in sterile saline.

Tissue samples from guinea pigs were preserved in 10% neutral buffered formalin for histological examination. Tissue samples were not histologically examined.

TABLE 16

| Compound | Guinea Pig | Dilution | Observation |
|---|---|---|---|
| BCTP | 1023-1 | undiluted | no reaction |
| | 1023-2 | 1:10 | no reaction |
| | 1023-3 | 1:100 | no reaction |
| Saline | 1023-10 | | no reaction |

The results of In Vivo Toxicity Study I show that subcutaneous and intramuscular injection of the compounds tested did not result in grossly observable tissue damage and did not appear to cause distress in the experimental animals (Table 16).

Example 8

In Vivo Toxicity Study II

One group of Sprague-Dawley rats each consisting of five males and five females were placed in individual cages and acclimated for five days before dosing. Rats were dosed daily for 14 days. On day 0–13, for 14 consecutive days each rat in Group 1 received by gavage three milliliters of BCTP, 1:100 concentration, respectively. The three-milliliter volume was determined to be the maximum allowable oral dose for rats. Prior to dosing on Day 0 and Day 7, each rat was weighed. Thereafter rats were weighed weekly for the duration of the study. Animals were observed daily for sickness or mortality. Animals were allowed to rest for 14 days. On Day 28 the rats were weighed and euthanized. The mean weight results of the oral toxicity study are shown in Table 17. Mean weights for males and females on Days 0, 7, and 14, 21 and 28 and the mean weight gains from Day 0–Day 28, are also shown in Table 17. One rat died due to mechanical trauma from manipulation of the gavage tubing during dosing on Day 14. All surviving rats gained weight over the 28 day course of the study and there was no illness reported. Thus, although tributyl phosphate alone is known to be toxic and irritating to mucous membranes, when incorporated into the emulsions of the present invention, these characteristics are not in evidence. The BCTP emulsion, 1:100 concentration, was also tested for dermal toxicity in rabbits according to the protocols provided in 16 CFR §1500.3. The emulsion was not irritating to skin in the animals tested.

practice the present invention, and the present invention is not limited to any particular mechanism. The effect of a GMO/CPC lipid emulsion ("P10") and BCTP on *E. coli* was examined. P10 killed the *E. coli* (in deionized $H_2O$) but BCTP was ineffective against this organism. FIG. 8 shows the control and FIG. 9 shows the *E. coli* treated with BCTP. As shown in FIG. 9, the BCTP treated *E. coli* look normal, with defined structure and intact lipid membranes. FIG. 10 shows the P10 treated *E. coli*, wherein the bacteria have vacuoles inside and the contents have swollen so that the defined structure of the organism is lost. Without being bound to a particular theory (an understanding of the mechanism is not necessary to practice the present invention, and the present invention is not limited to any particular mechanism), this observation suggests that P10 kills the bacteria without lysing them and instead causes a change in the internal structure, evident by the vacuolization and swelling. A second study was performed with *Vibrio cholerae*. Despite *Vibrio cholerae* being closely related to *E.*

TABLE 17

| Rat Number | Sex | Dose Volume mL | Body Weight (g) Day 0 | Body Weight (g) Day 7 | Body Weight (g) Day 14 | Body Weight (g) Day 21 | Body Weight (g) Day 28 | Weight Gain (g) Day 0 Day 28 |
|---|---|---|---|---|---|---|---|---|
| 9028 | m | 3 | 332.01 | 356.52 | 388.66 | 429.9 | 394.07 | 62.06 |
| 9029 | m | 3 | 278.62 | 294.65 | 296.23 | 310.7 | 392.6 | 113.98 |
| 9030 | m | 3 | 329.02 | 360.67 | 325.26 | 403.43 | 443.16 | 114.14 |
| 9031 | m | 3 | 334.64 | 297.04 | 338.82 | 357.5 | 416.89 | 82.25 |
| 9032 | m | 3 | 339.03 | 394.39 | 347.9 | 331.38 | 357.53 | 18.5 |
| MEAN WTS | | | 266.26 | 340.65 | 339.37 | 400.85 | 78.18 | |
| 9063 | F | 3 | 302 | 298.08 | 388.66 | 338.41 | 347.98 | 45.98 |
| 9064 | F | 3 | 254.54 | 247.97 | 256.78 | 278.17 | 279.2 | 24.66 |
| 9065 | F | 3 | 225.99 | 253.81 | 273.38 | 290.54 | 308.68 | 82.69 |
| 9066 | F | 3 | 246.56 | 260.38 | 266.21 | 235.12 | 272.6 | 26.04 |
| 9067 | F | 3 | 279.39 | 250.97 | deceased | | | |
| MEAN WTS | | | 261.69 | 262.24 | 296.25 | 285.56 | 302.11 | 53 |

Example 9

In Vitro Study With Bacillus Anthracis

Figure 3:
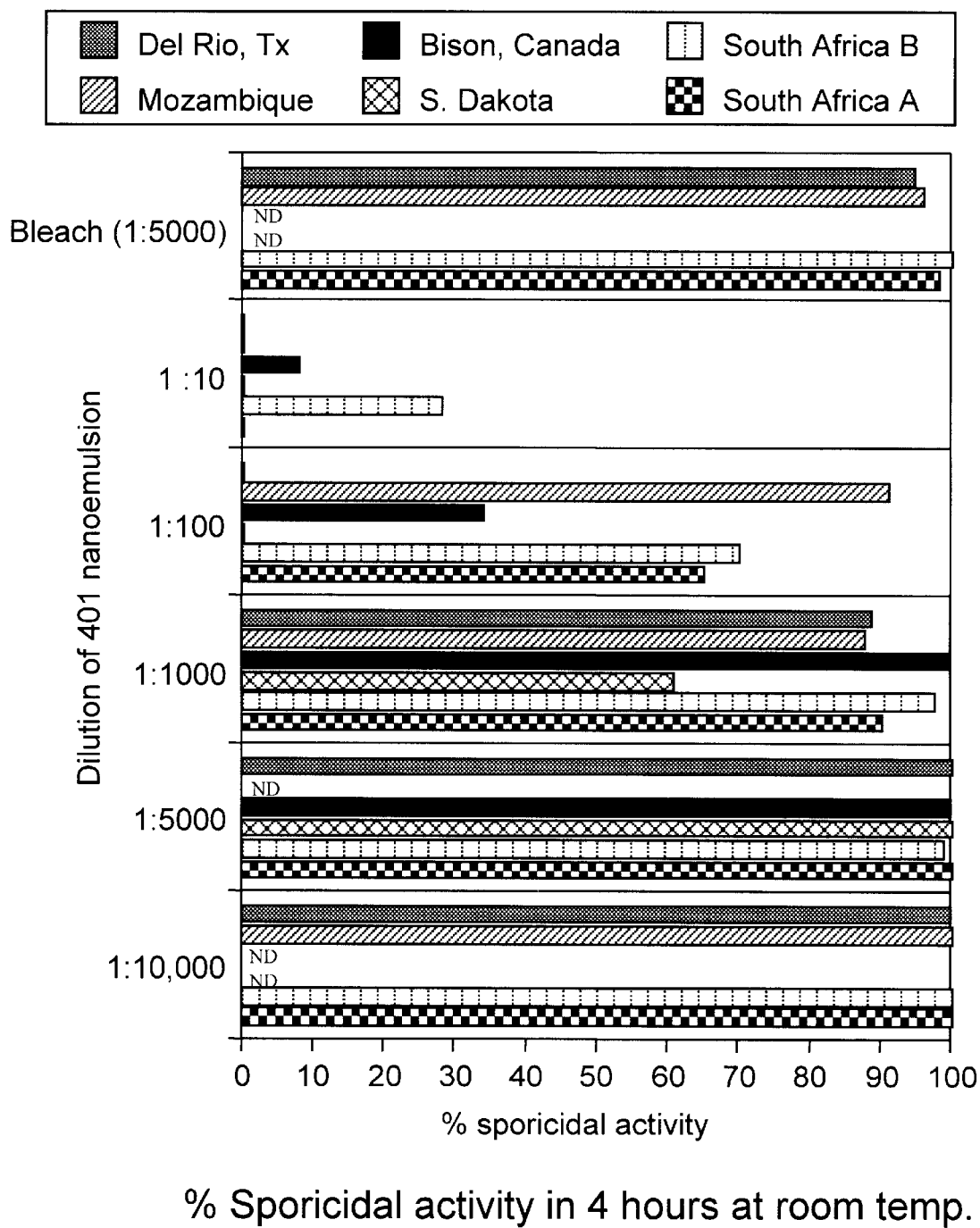
FIG. 3 illustrates the sporicidal activity of different dilutions of an emulsion of the present invention on different *B. anthracis* spores.
Figure 4:
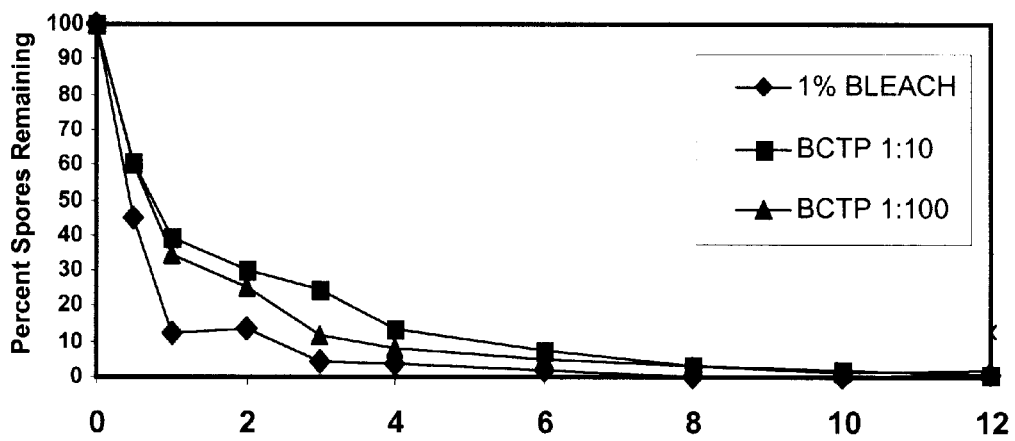
FIG. 4 and FIG. 5 illustrates a comparison of the sporicidal activity of an emulsion of the present invention and bleach over time.
Figure 5:
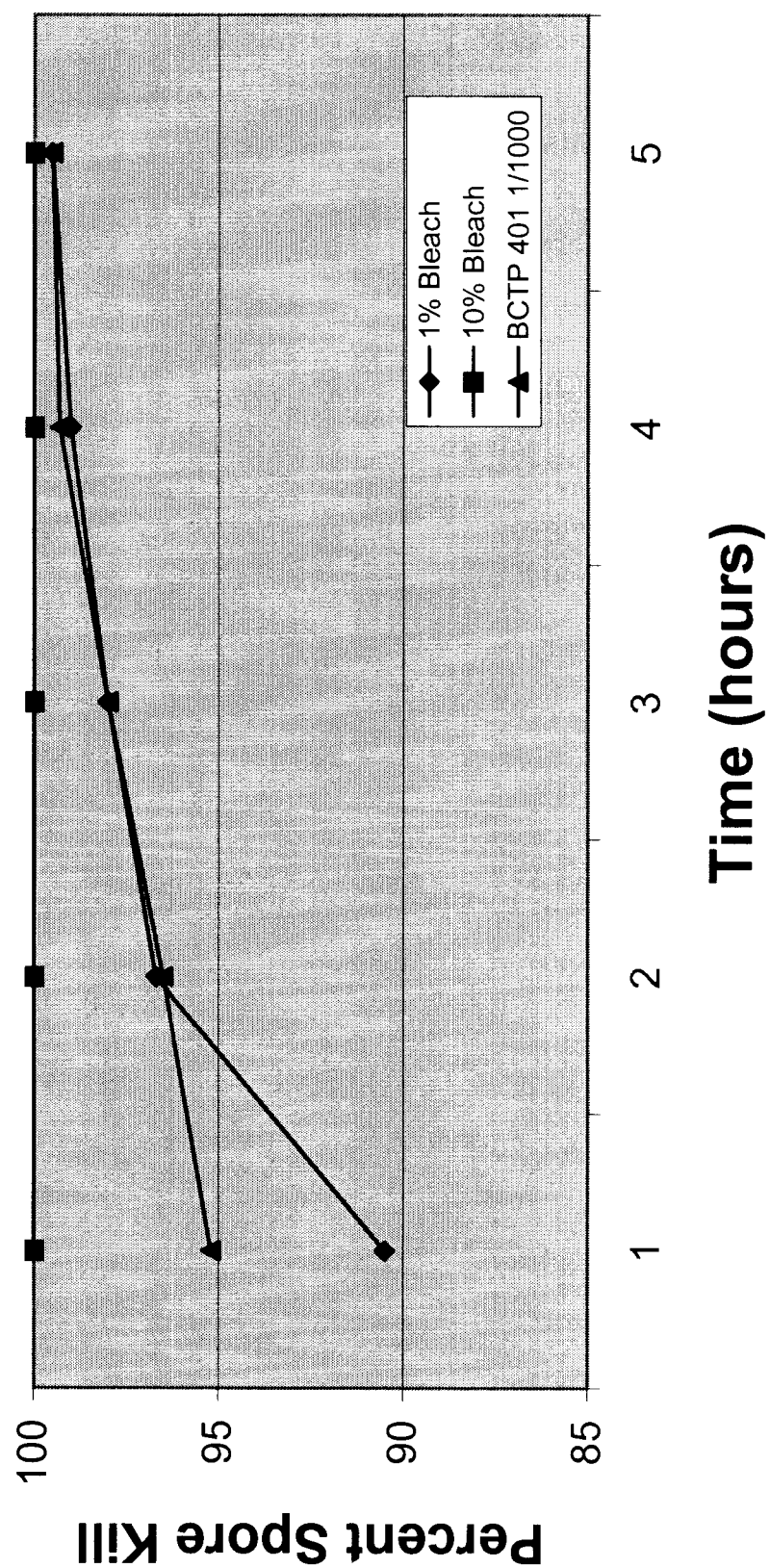
Figure 6:
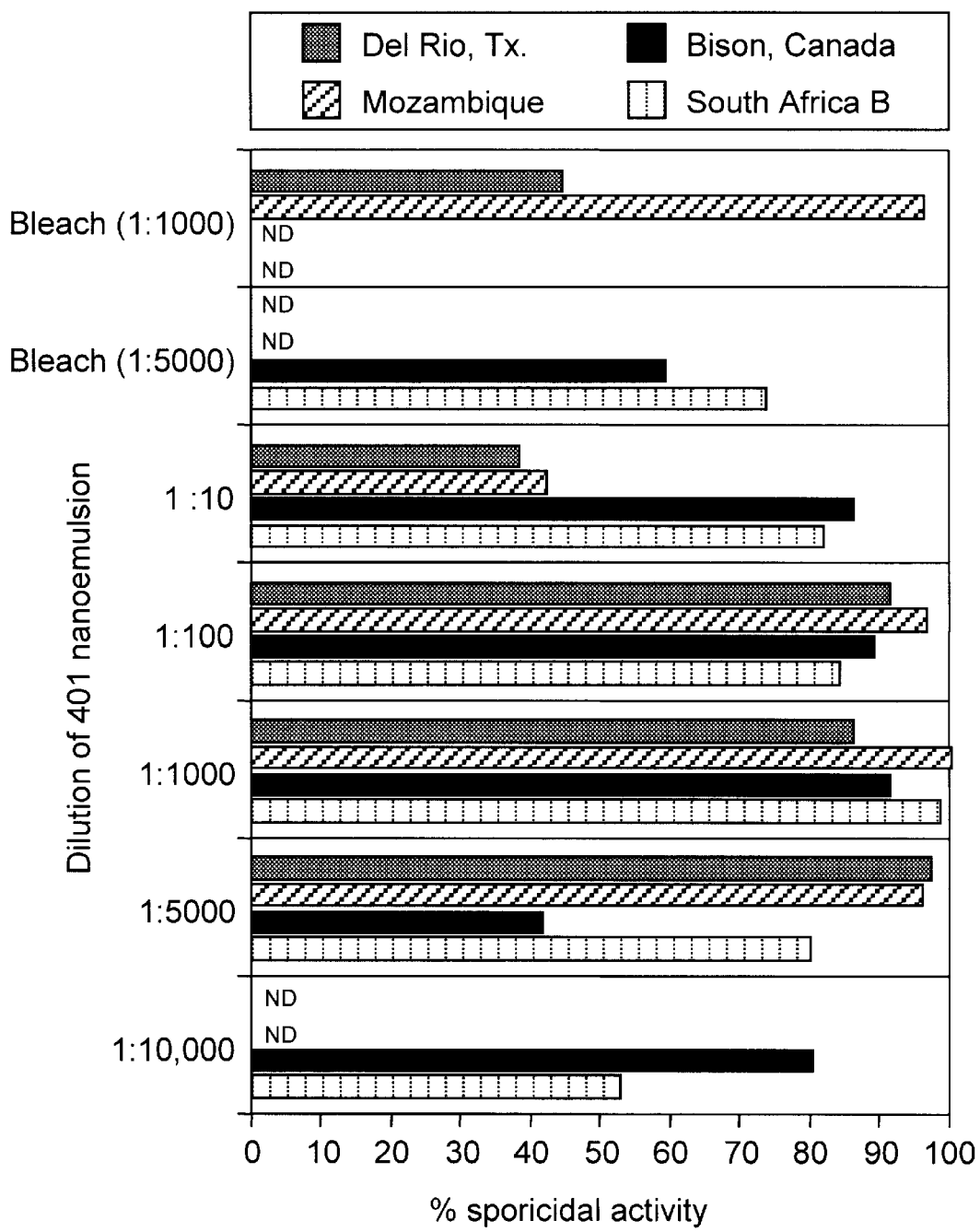
FIG. 6 illustrates the sporicidal activity of different dilutions of an emulsion of the present invention in media on different *B. anthracis* spores.
Figure 7:
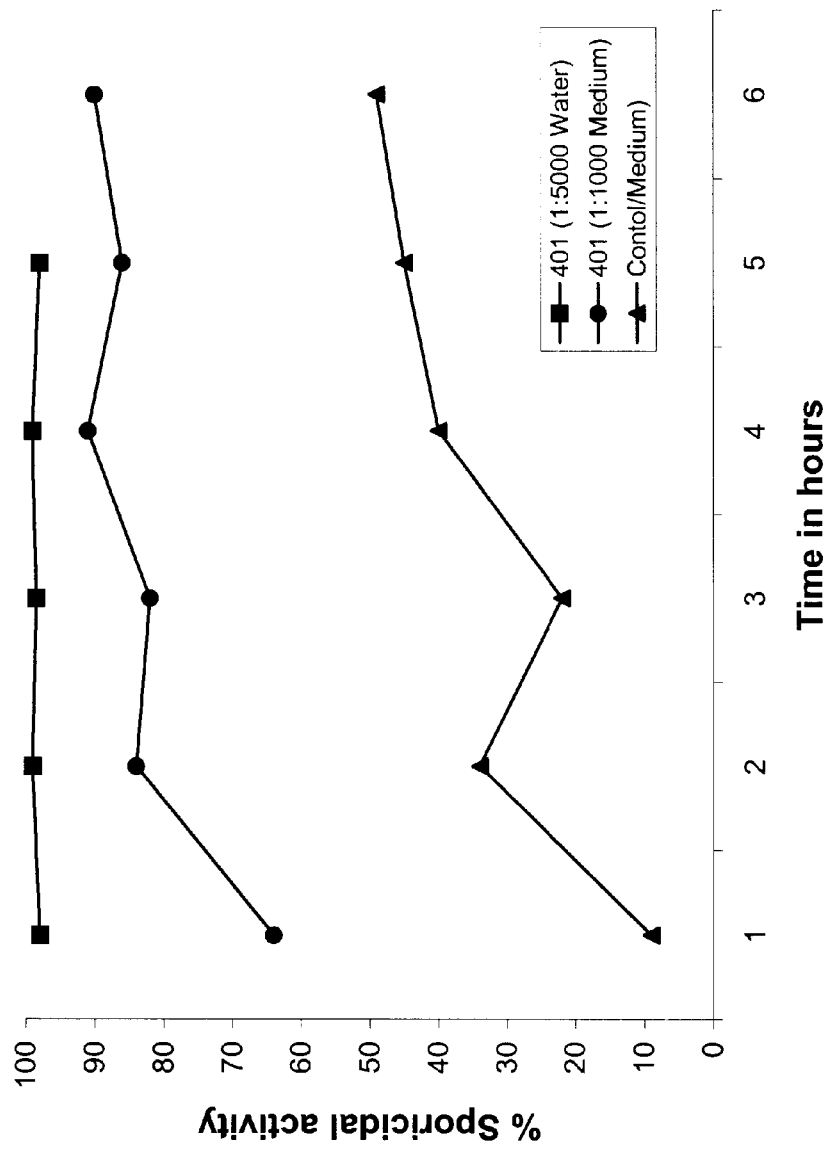
FIG. 7 illustrates the time course for the sporicidal activity of an emulsion of the present invention against *B. anthracis* from Del Rio, Tex.

Experiments with Novaclor 401 preparations to study the bactericidal effect of the compounds of the present invention on the spore form of *B. anthracis* were performed. The sporicidal activity of different dilutions of Novaclor 401 (in water) on six different strains of *B. anthracis* is shown in FIG. 3. As shown in FIGS. 4 and 5, Novaclor 401 killed over 98% of seven different strains of anthrax (those of FIG. 3 and Ames, USAMRID) within 4 hours and is as efficient as 1–10% bleach. Similar sporicidal activity is found with different dilutions of Novaclor 401 in media (FIG. 6). FIG. 7 shows the time course for the sporicidal activity of Novaclor 401 against the Del Rio, Tex. strain of *B. anthracis* compared with zero time at room temperature. As shown, Novaclor 401 can kill anthrax spores in as little as 30 minutes.

Example 10

Mechanisms Of Action

The following Example provides an insight into a proposed the mechanisms of action of the emulsions of the present invention and to show their sporicidal activity. This mechanism is not intended to limit the scope of the invention an understanding of the mechanism is not necessary to

Figure 11:
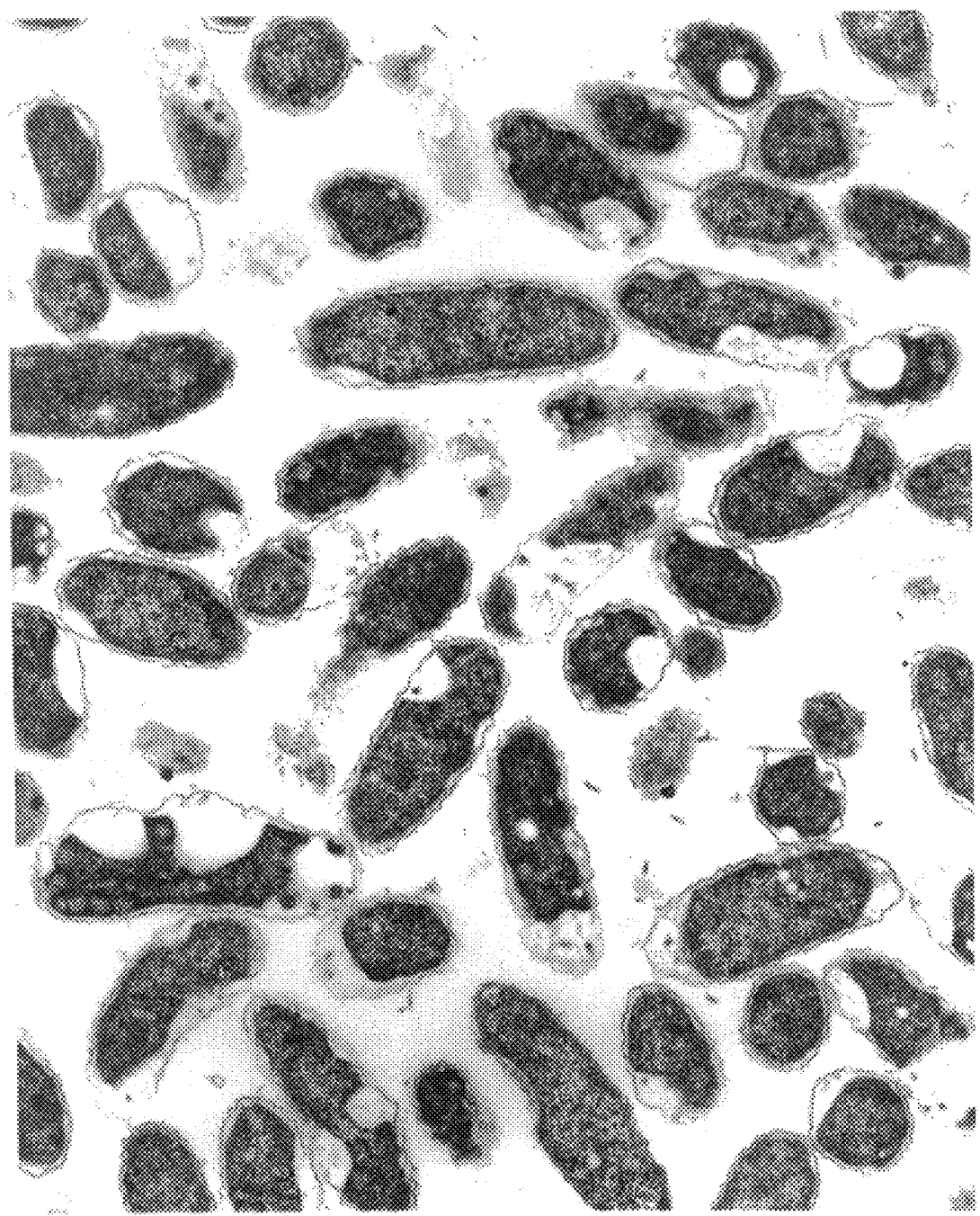
FIG. 11 depicts an electromicrograph of *Vibrio cholerae* (25,000×).
Figure 12:
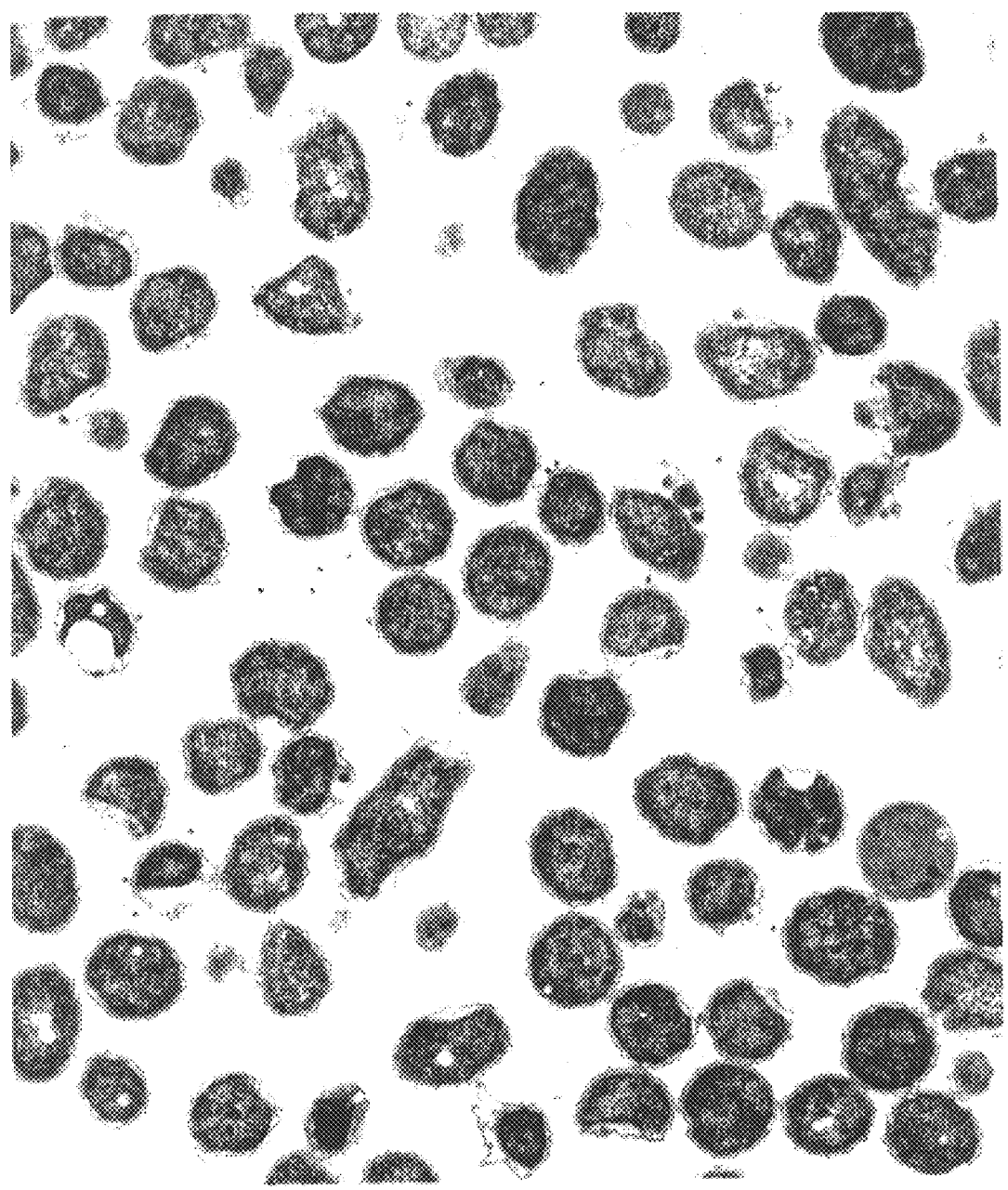
FIG. 12 depicts an electromicrograph of *Vibrio cholerae* treated with P10 (25,000×).
Figure 13:
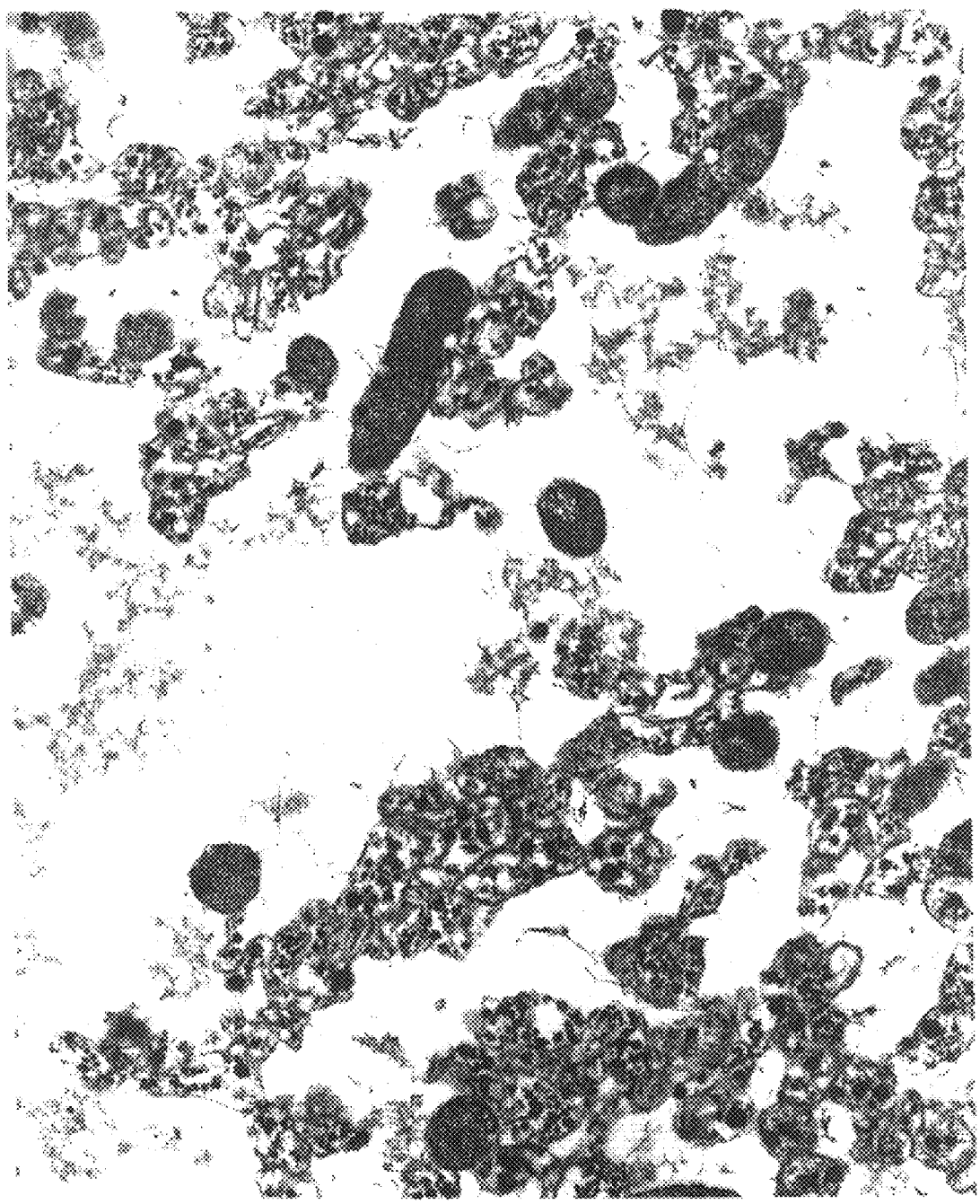
FIG. 13 depicts an electromicrograph of *Vibrio cholerae* treated with BCTP (25,000×).
Figure 14:
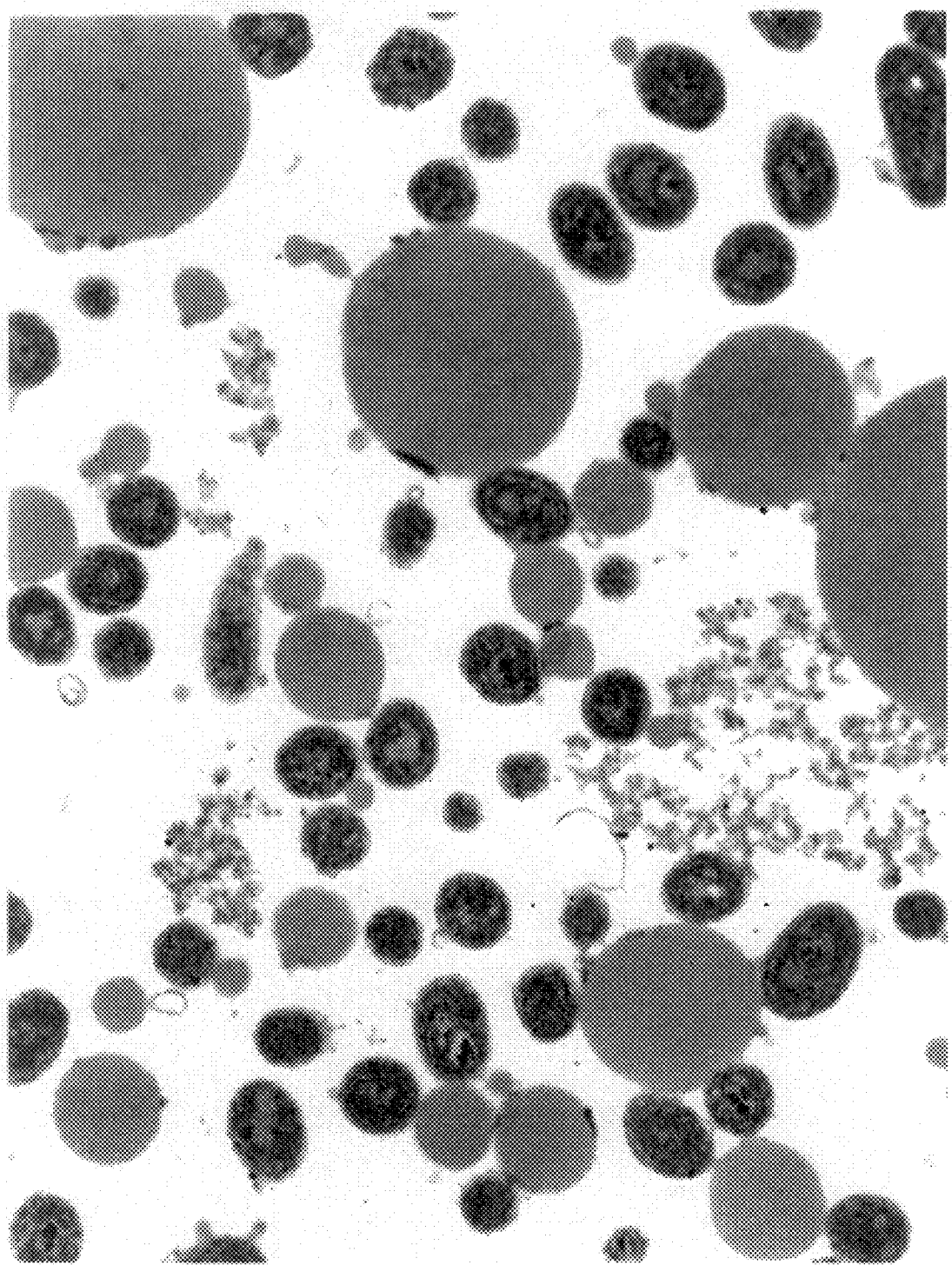
FIG. 14 depicts an electromicrograph of *Vibrio cholerae* treated with Novaclor 401 (25,000×).

*coli*, both the BCTP, P10 and Novaclor 401 killed this organism. Compared to the control electromicrograph (FIG. 11), the P10 treated *Vibrio cholerae* (FIG. 12) again shows swelling and changes in the interior of the organism, but the cells remain intact. In contrast, the BCTP treated *Vibrio cholerae* (FIG. 13) are completely lysed with only cellular debris remaining. Novaclor 401 (FIG. 14) showed a combination of effects, where some of the organisms are swelled but intact and some are lysed. This clearly suggests that BCTP, P10 and Novaclor 401 work by different mechanisms.

Figure 15:
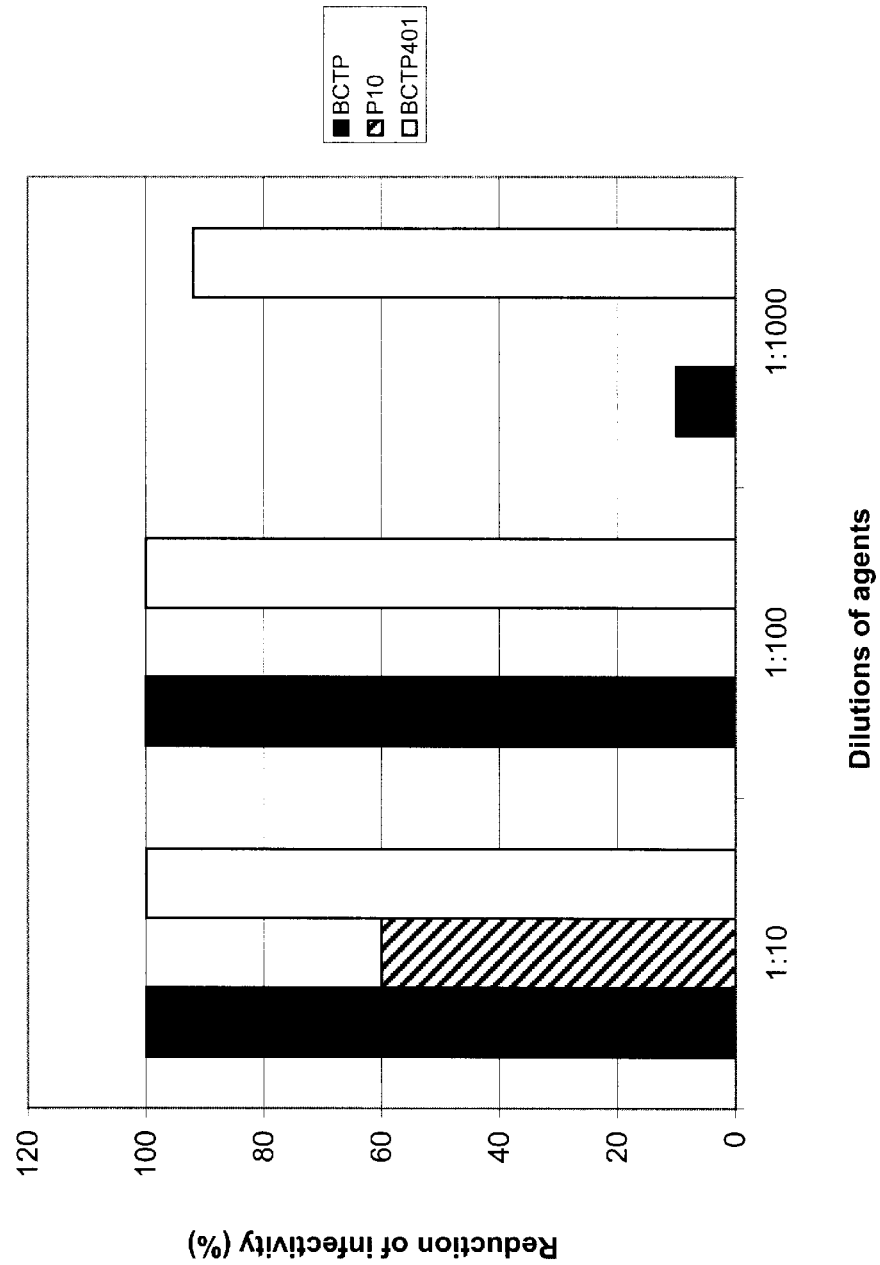
FIG. 15 illustrates the effect of BCTP, P10 and Novaclor 401 on influenza A activity.

A third comparative study was performed to evaluate efficacy of the emulsions at various concentrations. As shown in Table 18, Novaclor 401 is more effective as a biocide at lower concentrations (higher dilutions) in bacteria sensitive to either P10 or BCTP. In addition, six other bacteria that are resistant to P10 and BCTP are all susceptible to Novaclor 401. This difference in activity is also seen when comparing P10 and BCTP and Novaclor 401 in influenza infectivity assays. As shown in FIG. 15, both BCTP and Novaclor 401 are effective at a 1:10 and 1:100 dilutions and additionally, Novaclor 401 is effective at the lowest concentration, 1:1,000 dilution. In contrast, P10 has little activity even at 1:10 dilution, suggesting that it is not an effective treatment for this enveloped organism. In addition, Novaclor 401 kills yeast species that are not killed by either P10 or BCTP.

TABLE 18

Lowest Nanoemulsion Concentration Required to Achieve Over 90% Killing of Selected Microorganisms

| Bacteria | P10 | BCTP | Novaclor 401 |
|---|---|---|---|
| *Streptococcus pyogenes* | No killing | 10% | 0.1% |
| *Streptococcus aglactiae* | 1%* | 1% | ND |
| *Streptococcus pneumonia* | 10%* | 1% | 0.1% |
| *Staphylococcus aureus* | No killing | No killing | 0.1% |
| *Neissetia gonoffhoeae* | ND | 1% | 0.1% |
| *Haemophilus influenzae* | 10% | 1% | 0.1% |
| *Vibrio cholerae* | 1% | 0.1% | 0.1% |
| *E. coli* | No killing # | No killing | 0.1% |
| *Salmonella typhimurium* | No killing # | No killing | 10% |
| *Shigella dysenteriae* | No killing # | No killing | 0.1% |
| *Proteus mirabilis* | No killing # | No killing | 1% |
| *Pseudomonas aeruginosa* | No killing | No killing | 10% |
| *Bacillus anthracis* spores | No killing @ 4H | 0.1% @ 4H | 0.1%–0.02% @ 4H |
| *Bacillus cereus* spores | 10% @ 4H | 1% @ 4H | 0.1% @ 4H |
| *Bacillus subtilus* spores | No killing @ 24H | No killing @ 24H | 0.1% @ 4H |
| *Yersinia enterocolitica* | ND | ND | 0.1% |
| *Yersinia pseudotuberculosis* | ND | ND | 0.1% |
| Fungi | | | |
| *Candida albicans* (ATCC 90028) | No Killing | No Killing | 1% |
| *Candida tropicalis* | No Killing | No Killing | 1% |
| Viruses | | | |
| Influenza A H2N2 | No Killing | 1% | 0.1% |
| Influenza B/Hong Kong/5/72 | ND | 1% | ND |
| Vaccinia | ND | 1% | % |
| Herpes simplex type I | ND | 1% | 0.1% |
| Sendai | ND | 1% | ND |
| Sindbis | ND | 1% | ND |
| Adenovirus | ND | No Killing | ND |

*Data for lower concentrations not available.
No killing except in deionized water.
10 ND = Not determined.

Example 11

Further Evidence Of The Sporicidal Activity of the Nanoemulsion Against Bacillus Species The present Example provides the results of additional investigations of the ability of particular embodiments of the emulsions of the present invention to inactivate different *Bacillus spores*. The methods and results from these studies are outlined below.

METHODS

Surfactant lipid preparations: BCTP, a water-in-oil nanoemulsion, in which the oil phase was made from soybean oil, tri-n-butyl phosphate, and Triton X-100 in 80% water. Novaclor 401 was prepared by mixing equal volumes of BCTP with P10 which is a liposome-like compound made of glycerol monostearate, refined Soya sterols, TWEEN 60, soybean oil, a cationic ion halogen-containing CPC and peppermint oil.

Spore preparation: For induction of spore formation, *Bacillus cereus* (ATTC 14579), *B. circulans* (ATC 4513), *B. megaterium* (ATCC 14581), and *B. subtilis* (ATCC 11774) were grown for a week at 37° C. on NAYEMn agar (Nutrient Agar with 0.1% Yeast Extract and 5 mg/l $MnSO_4$). The plates were scraped and the bacteria/spores suspended in sterile 50% ethanol and incubated at room temperature (27° C.) for 2 hours with agitation in order to lyse the remaining vegetative bacteria. The suspension was centrifuged at 2,500×g for 20 minutes and the pellet washed twice in cold $diH_2O$. The spore pellet was resuspended in Trypticase soy broth (TSB) and used immediately for experiments. *B. anthracis* spores, Ames and Vollum 1 B strains, were kindly supplied by Dr. Bruce Ivins (USAMRIID, Fort Detrick, Frederick, Md.), and prepared as previously described (Ivins et al., 1995). Four other strains of anthrax were kindly provided by Dr. Martin Hugh-Jones (LSU, Baton Rouge, La.). These strains represent isolates with high allelic dissimilarity from South Africa; Mozambique; Bison, Canada; and Del Rio, Tex.

In vitro sporicidal assays: For assessment of sporicidal activity of solid medium, Trypticase Soy Agar (TSA) was autoclaved and cooled to 55° C. The BCTP was added to the TSA at a 1:100 final dilution and continuously stirred while the plates were poured. The spore preparations were serially diluted (ten-fold) and 10 μl aliquots were plated in duplicate (highest inoculum was $10^5$ spores per plate). Plates were incubated for 48 hours aerobically at 37° C. and evaluated for growth.

For assessment of sporicidal activity in liquid medium, spores were resuspended in TSB. 1 ml of spore suspension containing $2×10^6$ spores (final concentration $10^6$ spores/ml) was mixed with 1 ml of BCTP or Novaclor 401 (at 2× final concentration in $diH_2O$) in a test tube. The tubes were incubated in a tube rotator at 37° C. for four hours. After treatment, the suspensions were diluted 10-fold in $diH_2O$. Duplicate aliquots (25 μl) from each dilution were streaked on TSA, incubated overnight at 37° C., and then colonies were counted. Sporicidal activity expressed as a percentage killing was calculated:

$$\frac{cfu \, [\text{initial}] - cfu \, [\text{post-treatment}]}{cfu \, [\text{initial}]} \times 100.$$

The experiments were repeated at least 3 times and the mean of the percentage killing was calculated.

Electron microscopy: *B. cereus* spores were treated with BCTP at a 1:100 final dilution in TSB using Edenmeyer flasks in a 37° C. shaker incubator. Fifty ml samples were taken at intervals and centrifuged at 2,500×g for 20 minutes and the supernatant discarded. The pellet was fixed in 4% glutaraldehyde in 0.1 M cacodylate (pH 7.3). Spore pellets were processed for transmission electron microscopy and thin sections examined after staining with uranyl acetate and lead citrate.

Germination inhibitors/stimulators: *B. cereus* spores (at a final concentration $10^6$ spores/ml) were suspended in TSB with either the germination inhibitor D-alanine (at final concentration of 1 μM) or with the germination stimulator L-alanine +inosine (at final concentration of 50 μM each) (Titball and Manchee, 1987; Foster and Johnston., 1990; Shibata et al., 1976) and then immediately mixed with BCTP (at a final dilution of 1:100) and incubated for variable interval. Then the mixtures were serially diluted, plated and incubated overnight. The next day the plates were counted and percentage sporicidal activity was calculated.

In vivo sporicidal activity: Two animal models were developed; in the first *B. cereus* spores (suspended in sterile saline) were mixed with an equal volume of BCTP at a final dilution of 1:10. As a control, the same B. cereus spore suspension was mixed with an equal volume of sterile saline. 100 μl of the suspensions containing 4×10$^7$ spores was then immediately injected subcutaneously into CD-1 mice.

In the second model, a simulated wound was created by making an incision in the skin of the back of the mice. The skin was separated from the underlying muscle by blunt dissection. The "pocket" was inoculated with 200 μl containing 2.5×10$^7$ spores (in saline) and closed using wound clips. One hour later, the clips were removed and the wound irrigated with either 2 ml of sterile saline or with 2 ml of BCTP (1:10 in sterile saline). The wounds were then closed using wound clips. The animals were observed for clinical signs. Gross and histopathology were performed when the animals were euthanized 5 days later. The wound size was calculated by the following formula: ½ a ×½ b ×π where a and b are two perpendicular diameters of the wound.

RESULTS

Figure 16:
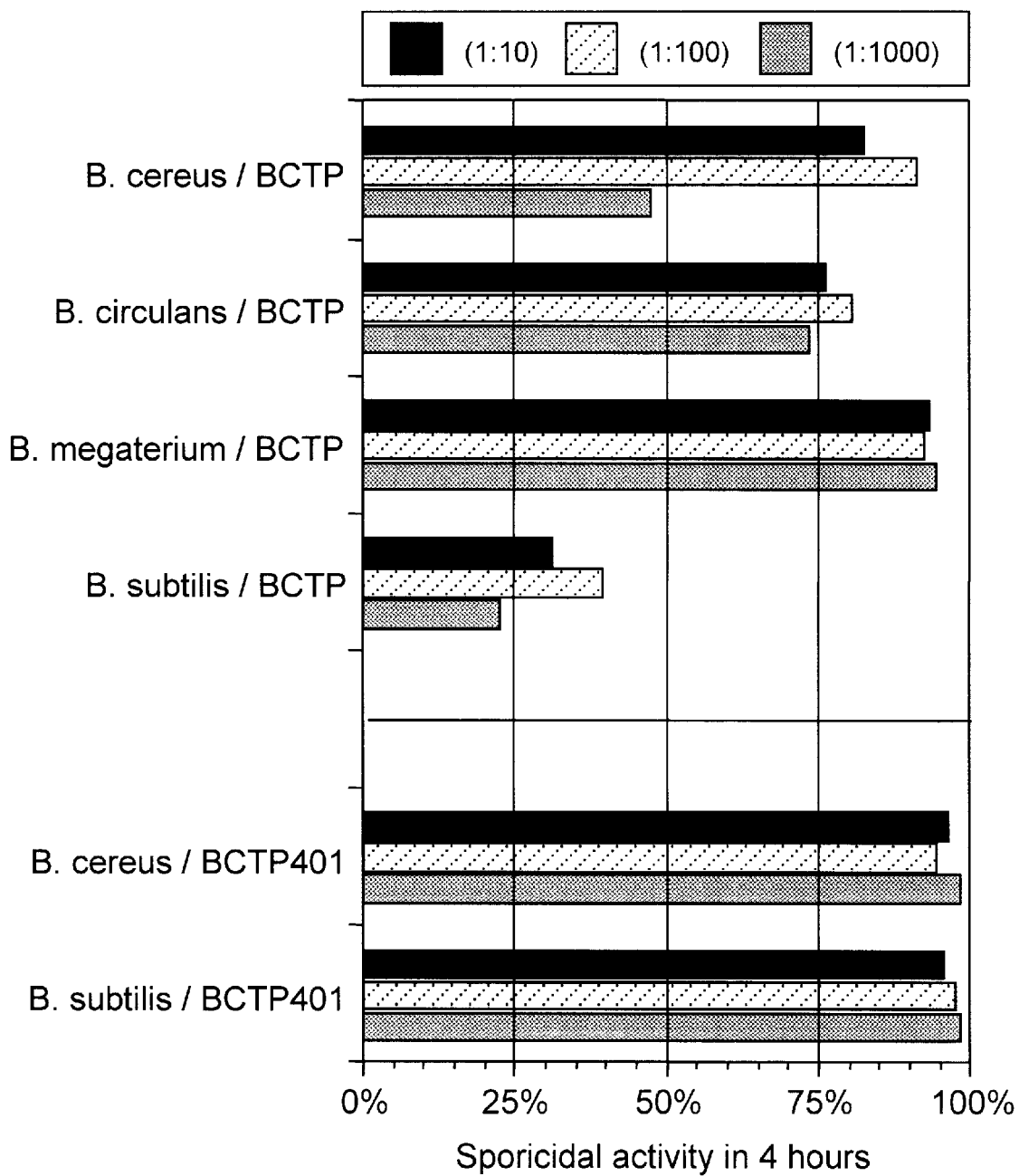
FIG. 16 illustrates the sporicidal activity of BCTP against 4 different Bacillus species compared to that of Novaclor 401 against 2 Bacillus species. BCTP showed a significant sporicidal activity after 4 hours of treatment against *Bacillus cereus, Bacillus circulans*, and *Bacillus megaterium* spores, but not against *Bacillus subtilis* spores. Novaclor 401, in 4 hours, showed more effective killing against *B. cereus* and also had a sporicidal activity against *B. subtilis* which was resistant to BCTP.

In vitro sporicidal activity: To assess the sporicidal activity of BCTP, spores from four species of Bacillus genus, B. cereus, B. circulans, B. megatetium, and B. subtilis were tested. BCTP at 1:100 dilution showed over 91% sporicidal activity against B. cereus and B. megaterium in 4 hours (FIG. 16). B. circulans was less sensitive to BCTP showing 80% reduction in spore count, while B. subtilis appeared resistant to BCTP in 4 hours. A comparison of the sporicidal effect of BCTP (at dilutions of 1:10 and 1:100) on B. cereus spores was made with a 1:100 dilution of bleach (i.e., 0.0525% sodium hypochlorite), and no significant difference was apparent in either the rate or extent of sporicidal effect. The other nanoemulsion, Novaclor 401, was more efficient in killing the Bacillus spores. At 1:1000 dilution, it showed 98% killing of B. cereus spores in 4 hours (compared to 47% with 1:1000 dilution of BCTP). Novaclor 401 at 1:1000 dilution resulted in 97.6% killing of B. subtilis spores in 4 hours, in contrast to its resistance to BCTP.

Figure 17:
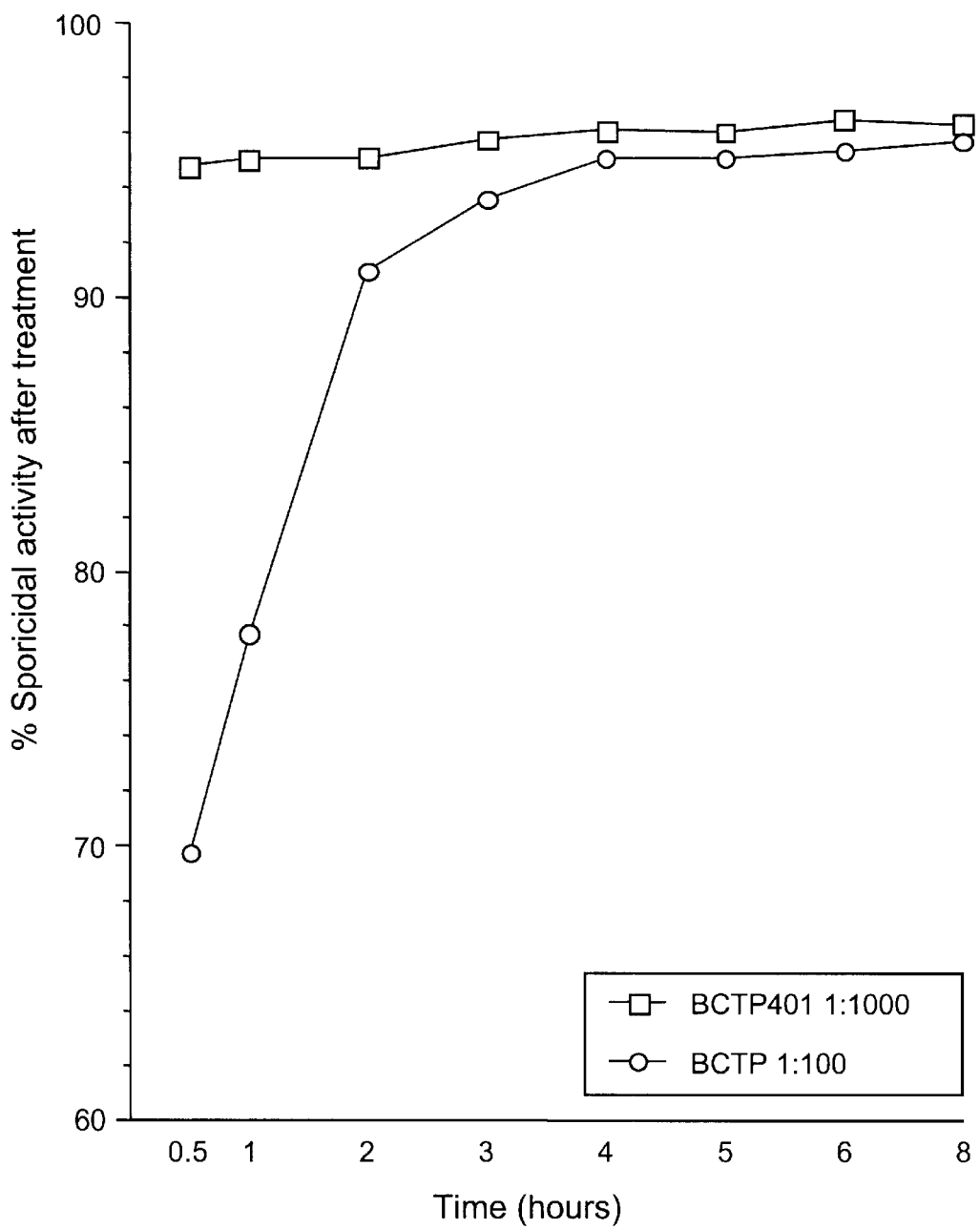
FIG. 17 illustrates the time course of the nanoemulsion sporicidal activity against *Bacillus cereus*. Incubation with BCTP diluted 1:100 resulted in 95% killing in 4 hours. Incubation with Novaclor 401 diluted 1:1000 resulted in 95% killing in only 30 minutes.

B. cereus sporicidal time course: A time course was performed to analyze the sporicidal activity of BCTP diluted 1:100 and Novaclor 401 diluted 1:1000 against B. cereus over an eight hour period. Incubation of BCTP diluted 1:100 with B. cereus spores resulted in a 77% reduction in the number of viable spores in one hour and a 95% reduction after 4 hours. Again, Novaclor 401 diluted 1:1000 was more effective than BCTP 1:100 and resulted in about 95% reduction in count after 30 minutes (FIG. 17).

BCTP B. anthracis sporicidal activity: Following initial in vitro experiments, BCTP sporicidal activity was tested against two virulent strains of B. anthracis (Ames and Vollum 1B). It was found that BCTP at a 1:100 final dilution incorporated into growth medium completely inhibited the growth of 1×10$^5$ B. anthracis spores. Also, 4 hours incubation with BCTP at dilutions up to 1:1000 with either the Ames or the Vollum 1 B spores resulted in over 91% sporicidal activity when the mixtures were incubated at RT, and over 96% sporicidal activity when the mixtures were incubated at 37° C. (Table 19).

Table 19: BCTP sporicidal activity against 2 different strains of Bacillus anthracis spores as determined by colony reduction assay (% killing). BCTP at dilutions up to 1:1000 effectively killed>91% of both spore strains in 4 hours at either 27 or 37° C.; conditions that differed markedly in the extent of spore germination. Sporicidal activity was consistent at spore concentrations up to 1×10$^6$/ml.

| B. anthracis | Ames Room Temp. | Ames (cont) 37° C. | Vollum 1 B Room Temp. | Vollum 1 B 37° C. |
|---|---|---|---|---|
| BCTP 1:10 | 91% | 96% | 97% | 99% |
| BCTP 1:100 | 93% | 97% | 97% | 98% |
| BCTP 1:1000 | 93% | 97% | 98% | 99% |

Novaclor 401 B. anthracis sporicidal activity: Since Novaclor 401 was effective at higher dilutions and against more species of Bacillus spores than BCTP, it was tested against 4 different strains of B. anthracis at dilutions up to 1:10,000 at RT to prevent germination. Novaclor 401 showed peak killing between 86% and 99.9% at 1:1000 dilution (Table 20).

Table 20: Novaclor 401 sporicidal activity against 4 different strains of B. anthracis representing different clinical isolates. The spores were treated with Novaclor 401 at different dilutions in RT to reduce germination. There as no significant killing at low dilutions. The maximum sporicidal effect was observed at 1:1000 dilution.

| B. Anthracis | South Africa | Bison, Canada | Mozambigue | Del Rio, Texas |
|---|---|---|---|---|
| Novaclor 401 1:10 | 81.8 | 85.9 | 41.9 | 38 |
| Novaclor 401 1:100 | 84 | 88.9 | 96.5 | 91.3 |
| Novaclor 401 1:1000 | 98.4 | 91.1 | 99.9 | 86 |
| Novaclor 401 1:5,000 | 79.7 | 41.3 | 95.7 | 97.1 |
| Novaclor 401 1:10,000 | 52.4 | 80 | ND | ND |

Figure 18A:
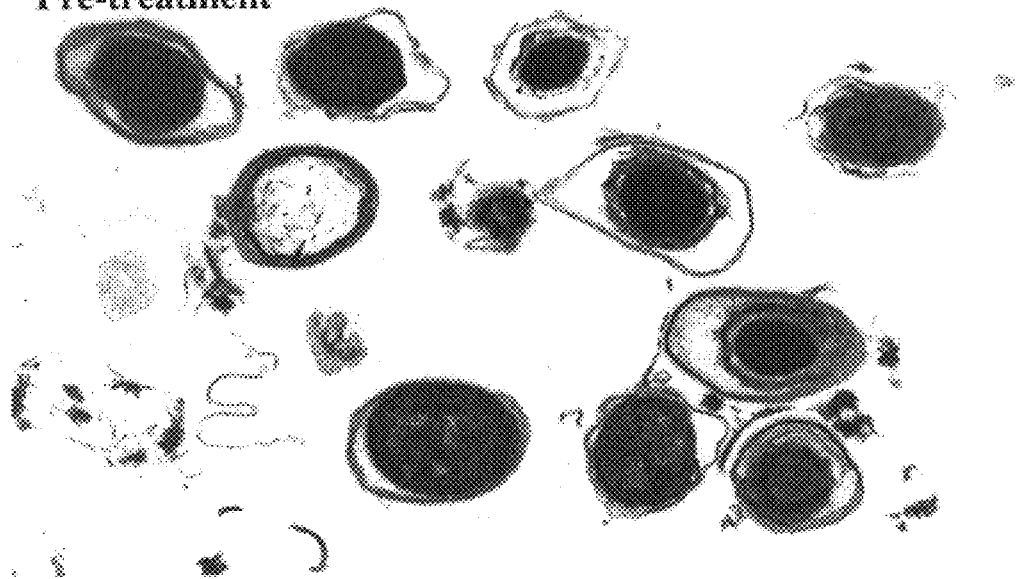
FIG. 18 depicts electronmicrographs of *Bacillus cereus* spores pre- and post-treatment with BCTP. Note, the uniform density in the cortex and the well-defined spore coat before treatment with BCTP. Spores after 4 hours of BCTP treatment show disruption in both the spore coat and the cortex with loss of core components.
Figure 18B:

Electron microscopy examination of the spores: Investigations were carried out using B. cereus because it is the most closely related to B. anthracis. Transmission electron microscopy examination of the B. cereus spores treated with BCTP diluted 1:100 in TSB for four hours revealed physical damage to the B. cereus spores, including extensive disruption of the spore coat and cortex with distortion and loss of density in the core (FIG. 18).

Figure 19:
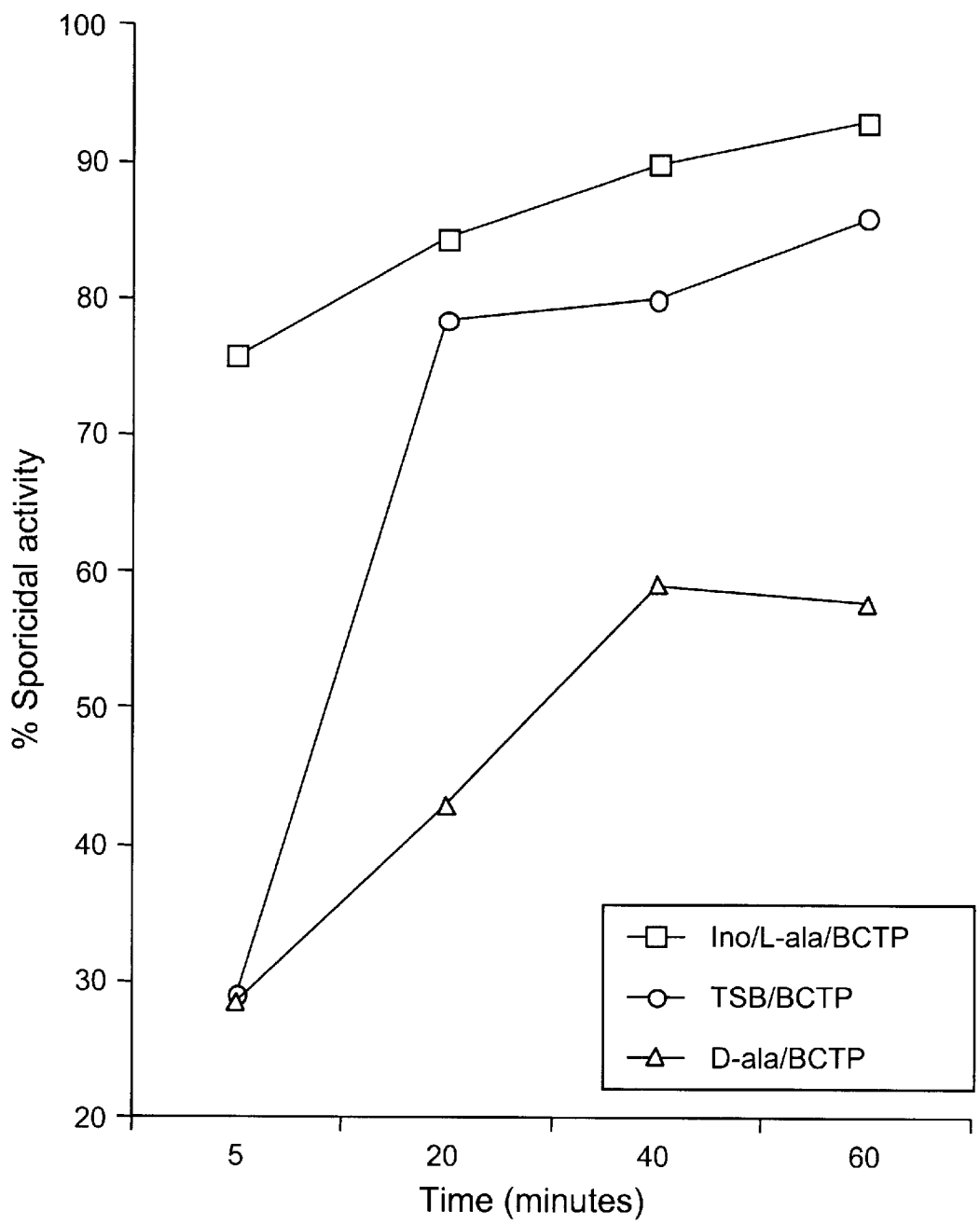
FIG. 19 illustrates the effects of germination inhibition and stimulation on the sporicidal activity of BCTP diluted 1:100. BCTP sporicidal activity was delayed in the presence of 10 mM D-alanine (germination inhibition), and accelerated in the presence of 50 $\mu$M L-alanine and 50 $\mu$M inosine (germination stimulation).

Germination stimulation and inhibition: To investigate the effect of initiation of germination on the sporicidal effect of BCTP on Bacillus spores, the germination inhibitors D-alanine (Titball and Manchee, 1987; Foster and Johnston, 1990), and germination stimulators L-alanine and inosine (Shibata et al., 1976) were incubated with the spores and BCTP for 1 hour. The sporicidal effect of BCTP was delayed in the presence of 10 mM D-alanine and accelerated in the presence of 50 μM L-alanine and 50 μM inosine (FIG. 19).

Figure 20:
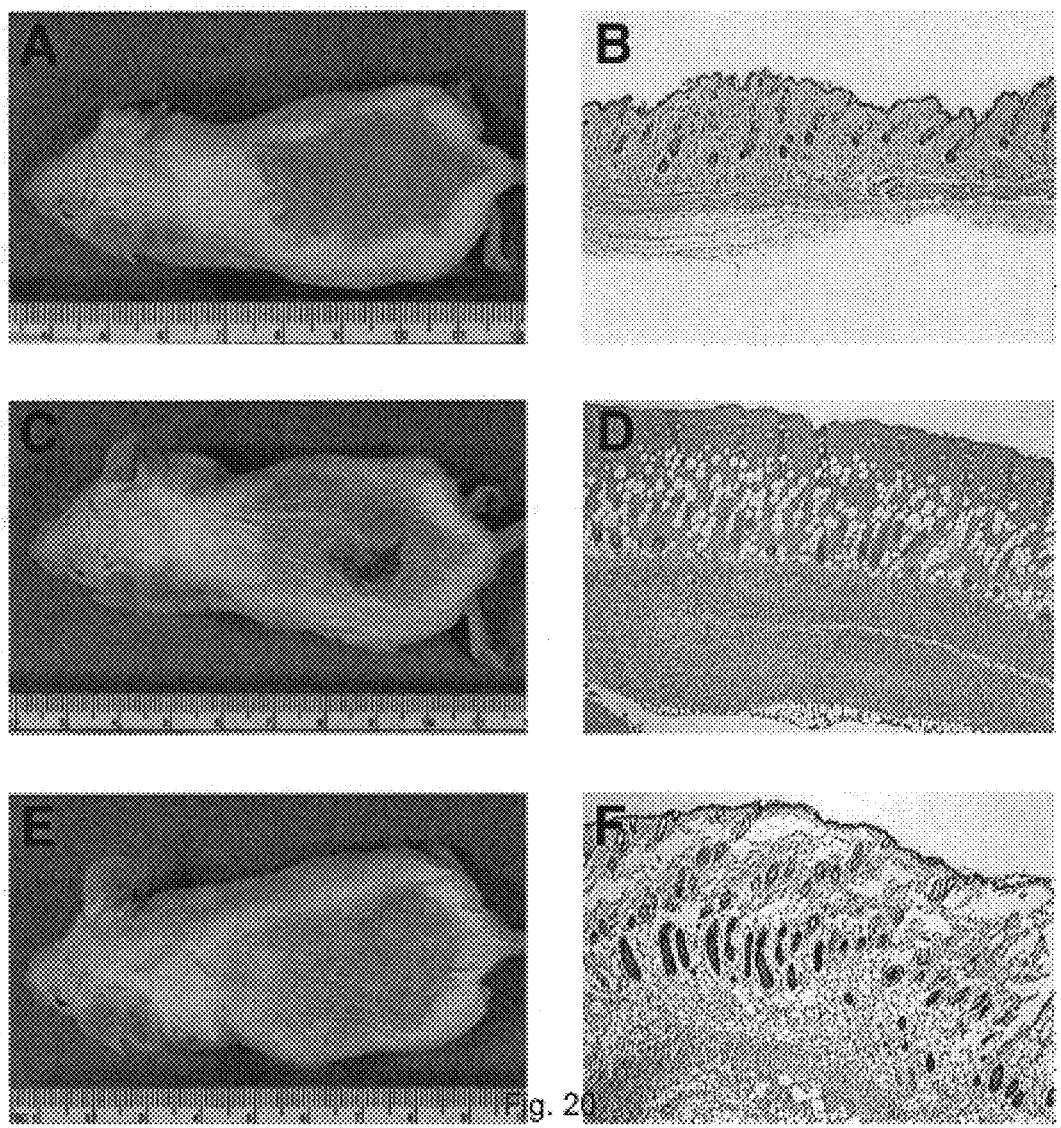
Figure 21:
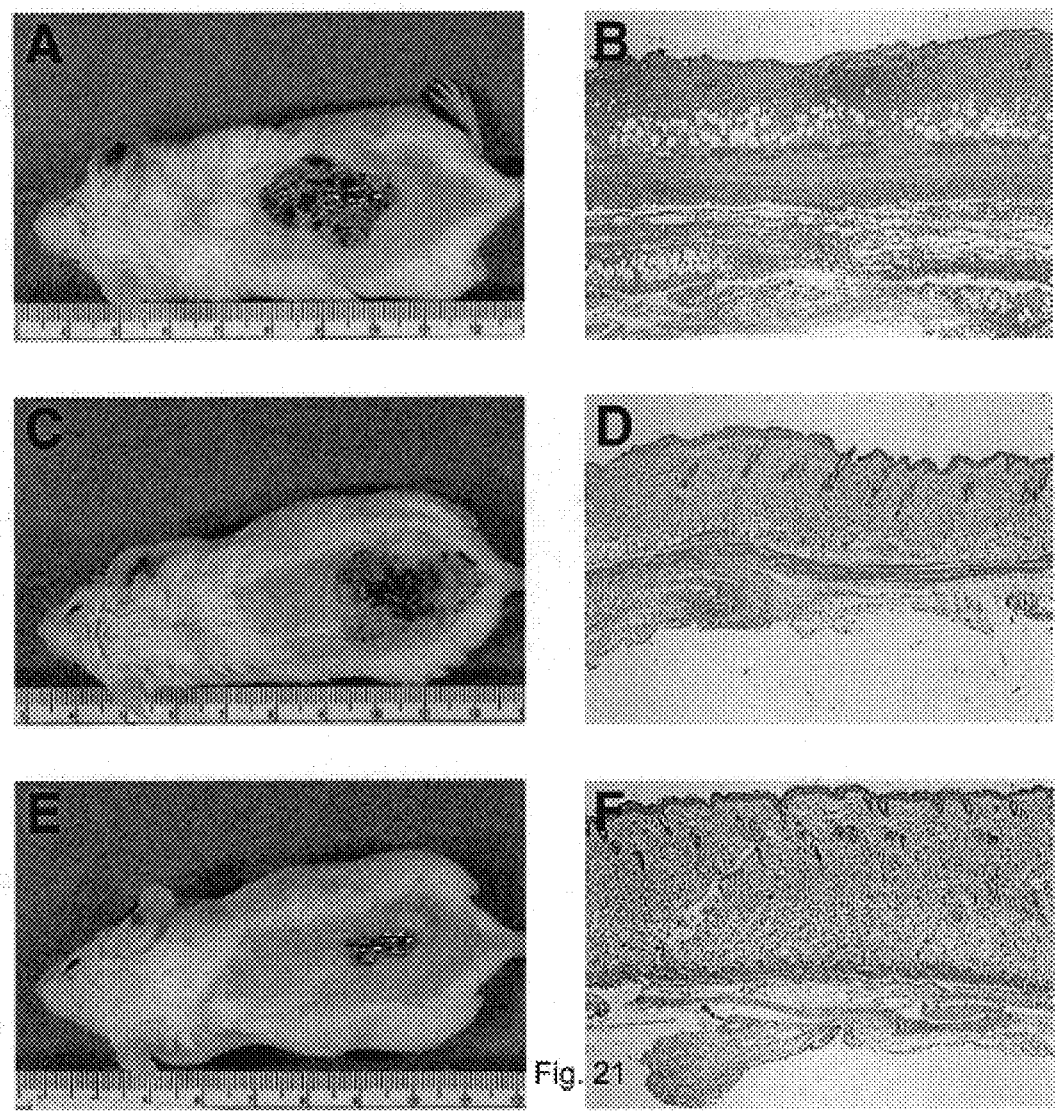
FIG. 21A–FIG. 21F depict gross and histological photographs of animals with experimental wounds infected with *Bacillus cereus* spores.

In vivo sporicidal activity: Bacillus cereus infection in experimental animals had been previously used as a model system for the study of anthrax and causes an illness similar to experimental anthrax infection (Welkos et al., 1986; Drobniewski, 1993; Burdon and Wende, 1960; Burdon et al., 1967; Fritz et al.1995 et al., 1995; Welkos and Friedlander, 1988). Two animal models of cutaneous B. cereus disease were developed to assess the in vivo efficacy of BCTP. Because these models involve subcutaneous administration of the nanoemulsion, in vivo toxicity testing of BCTP was performed prior to this application. CD-1 mice injected with BCTP diluted 1:10 in saline as a control did not exhibit signs of distress or inflammatory reaction, either in gross or histological analysis (FIG. 2A, FIG. 20B). To test the pathogenic effect of B. cereus spores in vivo and the sporicidal effect of BCTP, a suspension of 4×10$^7$ B. cereus spores was mixed with saline or with BCTP at a final dilution of 1:10 and then immediately injected subcutaneously into the back of CD-1 mice. Mice which were infected subcutaneously with *B. cereus* spores without BCTP developed severe edema at 6–8 hours. This was followed by a gray, necrotic area surrounding the injection site at 18–24 hours, with severe sloughing of the skin present by 48 hours, leaving a dry, red-colored lesion (FIG. 20C, FIG. 2D). Simultaneous injection of spores and BCTP resulted in a greater than 98% reduction in the size of the necrotic lesion from 1.68 $cm^2$ to 0.02 $cm^2$ when the spores were premixed with BCTP. This was associated with minimal edema or inflammation (FIG. 20E, FIG. 20 F).

In additional studies, a 1 cm skin wound was infected with $2.5\times10^7$ *B. cereus* spores then closed without any further treatment (FIG. 21A, FIG. 21B). The other groups were infected with the same number of spores, then 1 hour later the wounds were irrigated with either BCTP or saline to simulate post-exposure decontamination. Irrigation of experimentally infected wounds with saline did not result in any apparent benefit (FIG. 21C, FIG. 21D). BCTP irrigation of wounds infected with *B. cereus* spores showed substantial benefit, resulting in a consistent 98% reduction in the lesion size from 4.86 $cm^2$ to 0.06 $cm^2$ (FIG. 21E, FIG. 21F). This reduction in lesion size was accompanied by a four-fold reduction in mortality (80% to 20%) when compared to experimental animals receiving either no treatment or saline irrigation.

Example 12

Effect Of Surfactant Lipid Preparations (SLPS) On Influenza A Virus Infectivity In Vitro Enveloped viruses are of great concern as pathogens. They spread rapidly and are capable of surviving out of a host for extended periods. Influenza A virus was chosen because it is a well accepted model to test anti-viral agents (Karaivanova and Spiro, 1998; Mammen et al, 1995; Huang et al, 1991). Influenza is a clinically important respiratory pathogen that is highly contagious and responsible for severe pandemic disease (Mulder and Hers, 1972).

The envelope glycoproteins, hemagglutinin (HA) and neuraminidase (NA) not only determine the antigenic specificity of influenza subtypes (Schulze, 1997), but they mutate readily and, as a result, may allow the virus to evade host defense systems. This may result in the initiation of disease in individuals that are immune to closely related strains. The following is a description of the methods and composition used for determining the efficacy of SLPs in preventing influenza A infectivity.

METHODS

Surfactant lipid preparations (SLPs): The SLPs were made in a two-step procedure. An oil phase was prepared by blending soybean oil with reagents listed in Table 1 and heating at 86° C. for one hour (Florence, 1993). The SLPs were then formed by injecting water or 1% bismuth in water (SS) into the oil phase at a volume/volume ratio using a reciprocating syringe pump.

Viruses: Influenza virus A/AA/6/60 (Hedocher et al., 1996) was kindly provided by Dr. Hunein F. Maassab (School of Public Health, University of Michigan). Influenza A virus was propagated in the allantoic cavities of fertilized pathogen-free hen eggs (SPAFAS, Norwich, Conn.) using standard methods (Barrett and Inglis, 1985). Virus stock was kept in aliquots ($10^8$ pfu/ml) of infectious allantoic fluids at −80° C. Adenoviral vector (AD.RSV ntlacZ) was provided by Vector Core Facility (University of Michigan Medical Center, Ann Arbor, Mich.) and was kept in aliquots ($10^{12}$ pfu/ml at −80° C.). The vector is based on a human adenoviral (serotype 5) genomic backbone deleted of the nucleotide sequence spanning E1A and E1B and a portion of E3 region. This impairs the ability of the virus to replicate or transform nonpermissive cells. It carries the *Eschetichia coli* LacZ gene, encoding, β-galactosidase, under control of the promoter from the Rouse sarcoma virus long terminal repeat (RSV-LTR). It contains a nuclear targeting (designated as nt) epitope linked to the 5' end of the LacZ gene to facilitate the detection of protein expression (Baragi et al., 1995).

Cells: Madin Darby Canine Kidney (MDCK) cells were purchased from the American Type Culture Collection (ATCC; Rockville, Md.) and 293 cells (CRL 1573; transformed primary embryonic human kidney) were obtained from the Vector Core Facility (University of Michigan Medical Center, Ann Arbor, Mich.). The 293 cells express the transforming gene of adenovirus 5 and therefore restore the ability of Ad.RSV ntlacZ vector to replicate in the host cell (Graham et al., 1977).

Cell maintenance media: MDCK cells were maintained in Eagle's minimal essential medium with Earle's salts, 2 mM L-glutamine, and 1.5 g/l sodium bicarbonate (Mediatech, Inc., Hemdon, Va.) containing 10% fetal bovine serum (FBS; Hyclone Laboratories, Logan, Utah). The medium was supplemented with 0.1 mM non-essential amino acids, 1.0 mM sodium pyruvate, 100 U penicillin/ml and streptomycin 100 $\mu$g/ml (Life Technologies, Gaithersburg, Md.). The 293 cells were maintained in Dulbecco's modified Eagle medium (Mediatech, Inc., Herndon, Va.), containing 2 mM L-glutamine, 0.1 mM non-essential amino acids, and 1.0 mM sodium pyruvate. It also contained 100 U penicillin/ml and streptomycin 100 $\mu$g/ml (Life Technologies, Gaithersburg, Md.) and was supplemented with 10% FBS (Hyclone Laboratories, Logan, Utah).

Virus infection media: Influenza A infection medium was the MDCK cell maintenance medium (without FBS) supplemented with 3.0 $\mu$g/ml of tolylsulfonyl phenylalanyl chloromethyl ketone (TPCK)-treated trypsin (Worthington Biochemical Corporation, Lakewood, N.J.). Adenovirus infection medium was 293) cell maintenance medium with a reduced concentration of serum (2% FBS).

Influenza A overlay medium: Overlay medium consisted of equal amounts of 2× infection medium and 1.6% SEAKEM ME agarose (FMC BioProducts, Rockland, Md.). Staining agarose overlay medium consisted of agarose overlay medium plus 0.01% neutral red solution (Life Technologies, Gaithersburg, Md.) without TPCK-treated trypsin.

Plaque reduction assays (PRA): The plaque reduction assay was performed with a modification of the method described elsewhere (Hayden et al., 1980). MDCK cells were seeded at $1\times10^5$ cells/well in 12-well FALCON plates and incubated at 37° C./5% $CO_2$ for days. Approximately $1\times10^8$ pfu of influenza A virus was incubated with surfactant lipid preparations as described below. The influenza A virus-SLP treatments and controls were diluted in infection medium to contain 30–100 pfu/250 $\mu$l. Confluent cell monolayers were inoculated in triplicate on 3 plates and incubated at 37° C./5% $CO_2$ for 1 h. The inoculum/medium was aspirated and 1 ml of agarose overlay medium/well was added and plates were incubated at 37° C./5% $CO_2$ until plaques appeared. Monolayers were stained with the agarose overlay medium and incubation was continued at 37° C./5%

$CO_2$. Plaques were counted 6–12 h after staining. The average plaque count from 9 wells with lipid preparation concentration was compared with the average plaque count of untreated virus wells.

In situ cellular enzyme-linked immunosorbent assay (ELISA): To detect and quantitate viral proteins in MDCK cells infected with influenza A virus, the in situ cellular ELISA was optimized. Briefly, $2\times10^4$ MDCK cells in 100 µl complete medium were added to flat-bottom 96-well microtitre plates and incubated overnight. On the next day, the culture medium was removed and cells were washed with serum free maintenance medium. One hundred µl of viral inoculum was added to the wells and incubated for 1 hour. The viral inoculum was removed and replaced with 100 µl of MDCK cell maintained medium plus 2% FBS. The infected MDCK cells were incubated for an additional 24 h. Then the cells were washed once with PBS and fixed with ice cold ethanol:acetone mixture (1:1) and stored at −20° C. On the day of the assay, the wells of fixed cells were washed with PBS and blocked with 1% dry milk in PBS for 30 min. at 37° C. One hundred µl of ferret anti-influenza A virus polyclonal antibody at 1:1000 dilution (kindly provided by Dr. Hunein F. Maassab, School of Public Health, University of Michigan) was added to the wells for 1 hr at 37° C. The cells were washed 4 times with washing buffer (PBS and 0.05% TWEEN-20), and incubated with 100 µl at 1:1000 dilution of goat anti-ferret peroxidase conjugated antibody (Kirkegaard & Perry Laboratories, Gaithersburg, Mass.) for 30 min. at 37° C. Cells were washed 4 times and incubated with 100 µl of 1-STEP TURBO TMB-ELISA substrate (Pierce, Rockford, Ill.) until color had developed. The reaction was stopped with 1 N sulfuric acid and plates were read at a wavelength of 450 nm in an ELISA microtiter reader.

β-galactosidase assay: β-galactosidase assay was performed on cell extracts as described elsewhere (Lim, 1989). Briefly, 293 cells were seeded on 96-well "U"—bottom tissue culture plates at approximately $4\times10^4$ cells/well and incubated overnight at 37° C./5% $CO_2$ in maintenance medium. The next day, the medium was removed and the cells were washed with 100 µl Dulbecco's phosphate buffered saline (DPBS). Adenovirus stock was diluted in infection medium to a concentration of $5\times10^7$ pfu/mi and mixed with different concentrations of BCTP as described below. After treatment with BCTP, virus was diluted with infection medium to a concentration of $1\times10^4$ pfu/mi and overlaid on 293 cells. Cells were incubated at 37° C./5% $CO_2$ for 5 days, after which the plates were centrifuged, the medium was removed and the cells were washed three times with PBS without Ca++ and Mg++. After the third wash, the PBS was aspirated and 100 µl of 1× Reporter Lysis Buffer (Promega, Madison, Wis.) was placed in each well. To enhance cell lysis, plates were frozen and thawed three times and the β-galactosidase assay was performed following the instruction provided by the vendor of β-galactosidase (Promega, Madison, Wis.) with some modifications. Five microliters of cell extract was transferred to a 96-well flat bottom plate and mixed with 45 µl of 1× Reporter Lysis Buffer (1:10). Subsequently 50 µl of 2× assay buffer (120 mM $Na_2HPO_4$, 80 mM $NaH_2PO_4$, 2 mM $MgCl_2$, 100 mM β-mercaptoethanol, 1.33 mg/ml ONPG (Sigma, St. Louis, Mo.) were added and mixed with the cell extract. The plates were incubated at RT until a faint yellow color developed. At that time the reaction was stopped by adding 100 (1 of 1 M sodium bicarbonate. Plates were read at a wavelength of 420 nm in an ELISA microplate reader. A standard, consisting of (u/µl β-galactosidase (Sigma, St. Louis, Mo.) supplemented in 50 mM bicine buffer (Sigma, St. Louis, Mo.), pH 7.5 and 100 (g/ml BSA) diluted in the 1× Reporter Lysis Buffer, was run with all assays. The units of β-galactosidase in each cell extract was calculated by regression analysis by reference to the levels in the standard and divided by milligrams of protein in the cell extract sample.

Cellular toxicity and virus treatment with lipid preparations: Prior to viral susceptibility testing, cytotoxicity of SLPs on MDCK and 293) cells was assessed by microscope inspection and MTT assay. The dilutions of the mixture of virus and SLPs applied in susceptibility testing were made to be at least one order of magnitude higher than the safe concentration of SLP assessed. Approximately $1\times10^8$ pfu of either influenza A or adenovirus were incubated with lipid preparation at final concentrations of 1:10, 1:100, and 1:1000 for different time periods as indicated in results on a shaker. After incubation, serial dilutions of the SLP/virus mixture were made in proper infection media and overlaid on MDCK (influenza A) or 293 (adenovirus) cells to perform PRA, cellular ELISA or β-galactosidase assays as described above.

Electron microscopy: Influenza A virus was semipurified from allantoic fluid by passing through a 30% sucrose cushion prepared with GTNE (glycine 200 mM, Tris-HCI 10 mM (pH 8.8), NaCl 100 mM, and EDTA 1 mM) using ultra centrifugation (Beckman rotor SW 28 Ti, at 20,000 rpm for 16 hours). Pelleted virus was reconstituted in GTNE. Ten microliters of respective samples (adenovirus, influenza virus, adenovirus +BCTP, influenza virus +BCTP) were incubated for 15 and 60 min, then placed on parlodian coated 200 mesh copper grids for 2 min. Then 5 µl of 2% cacodylated-buffered glutaraldehyde was added. The fluid was removed with filter paper after 3 min. Ten microliters of 7% uranyl acetate was added to the grid and drawn off with filter paper after 30 sec. The grids were allowed to dry 10 min and examined on a Philips EM400T transmission electron microscope. Micrographs were recorded in Fuji FG film at magnifications of 200,000×.

RESULTS

Figure 22A:
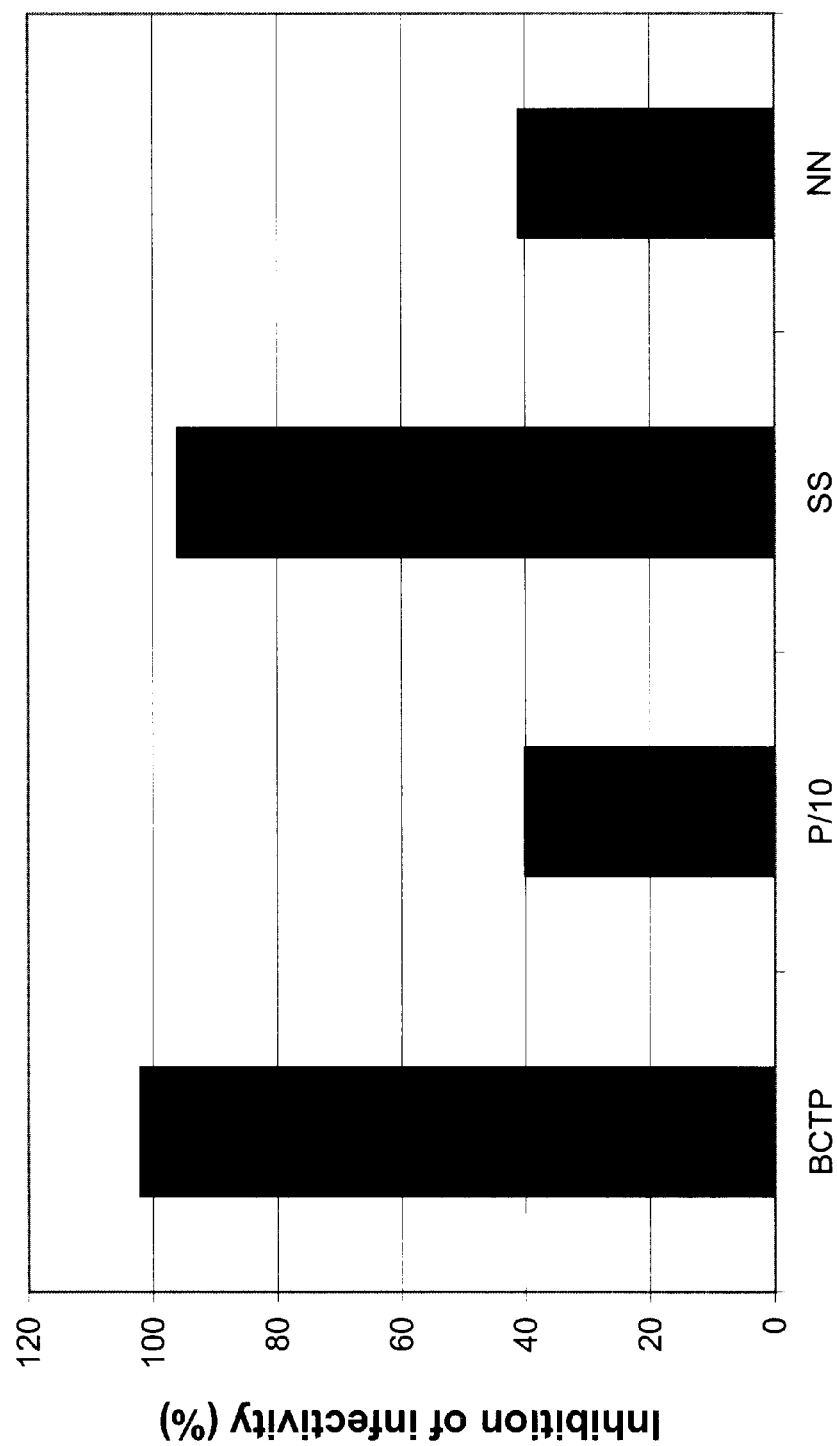
FIG. 22A represents BCTP, P10, SS, and NN.
Figure 22B:
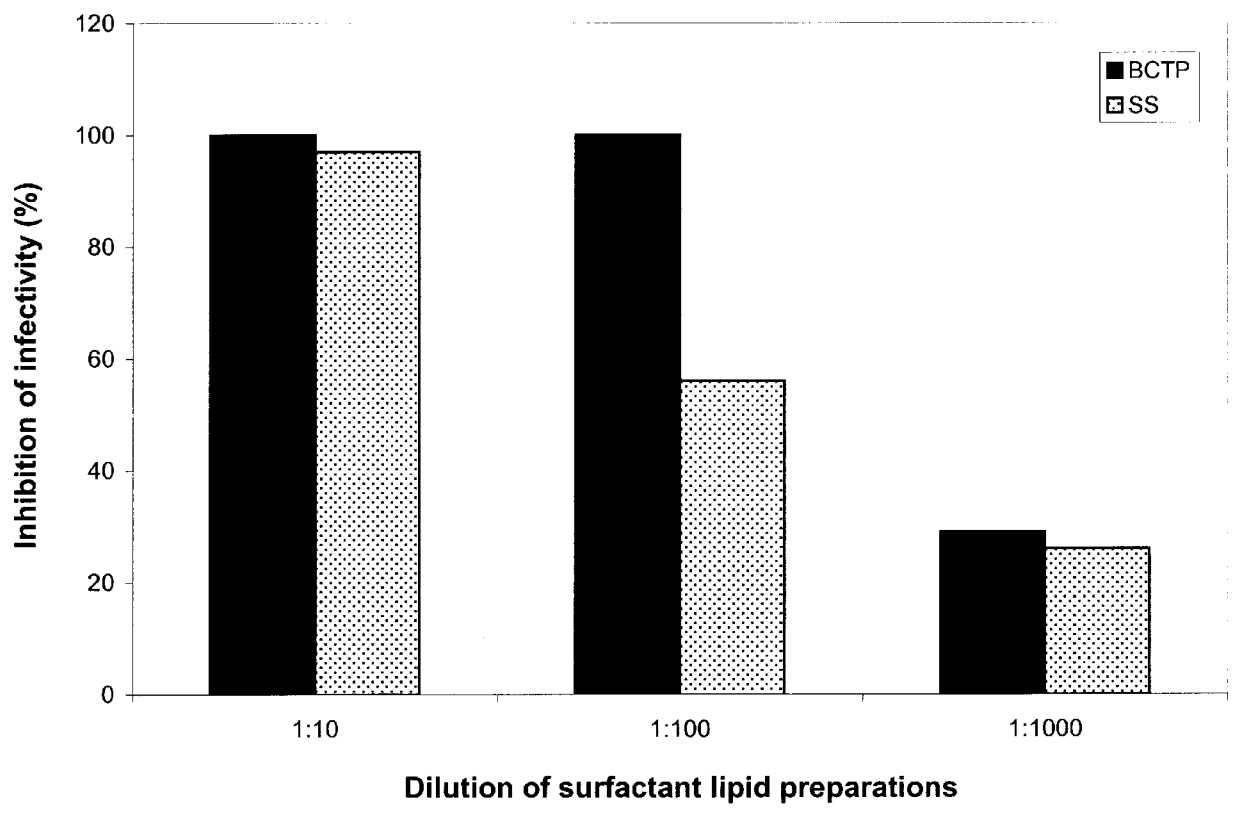

Susceptibility testing of influenza A to SLPS: the effect of four surfactant lipid preparations (BCTP, NN, P10, and SS) on influenza A infection of MDCK cells was investigated. All tested preparations inhibited influenza A virus infection to varying degrees as shown in FIG. 22. BCTP and SS exhibited over 95% inhibition of influenza A infection at a 1:10 dilution. NN and P10 showed only an intermediate effect on influenza A virus, reducing infection by approximately 40%. BCTP's virucidal effect was undiminished even at a 1:100 dilution. SS showed less effect at a 1:100 dilution inhibiting influenza A infection by 55%. These two lipid preparations at 1:1000 dilution displayed only weak inhibitory effect on virus infectivity at the range of 22–29% (FIG. 23B).

Since BCTP and SS both showed strong inhibitory effect on virus infectivity, PRA was used to verify data obtained from cellular ELISA. PRA confirmed the efficacy of BCTP and SS. BCTP reduced the number of plaques from an average of 50.88 to 0 at a 1:10 dilution (Table 21). At dilution 1:100, BCTP maintained virucidal effectiveness. At dilution 1:100 SS reduced the number of plaques only approximately 7% as compared with untreated virus.

TABLE 21

| Treatment Dilution of the agent: | Plaque forming units BCTP | Plaque forming units SS |
|---|---|---|
| 1:10[a] | 0.00[b] (+/−0.00)[c] | 0.00 (+/−0.00) |
| 1:100 | 0.00 (+/−0.00) | 1.55 (+1 − 0.12) |
| Untreated virus | 50.88 (+/−1−0.25) | 23.52 (+/−0.18) |

[a]Virus was incubate with SLPs for 30 minutes.
[b]Number of plaques.

Kinetics of BCTP action on influenza A virus: To investigate the time requirement for BCTP to act on influenza A infectivity, virus was incubated with BCTP at two dilutions (1:10, 1:100) and four different time intervals (5, 10, 15, 30 min). Subsequently, plaque reduction assay was performed. As shown in Table 22, after five min of incubation with BCTP at either dilution, influenza A virus infectivity of MDCK cells was completely abolished. There was no significant difference between the interaction of BCTP with influenza A virus regardless of concentration or time.

TABLE 22

| Time (min) | BCTP treatment/dilution | | |
|---|---|---|---|
| | 1:10 | 1:100 | untreated |
| 5 | 0.00[a] (+/−0.00)[b] | 0.00 (+/−0.00) | 35.25 (+/−0.94) |
| 10 | 0.00 (+/−0.00) | 0.25 (+/−0.12) | 39.25 (+/−1.95) |
| 15 | 0.00 (+/−0.00) | 0.25 (+/−0.12) | 31.50 (+/−1.05) |
| 30 | 0.00 (+/−0.00) | 0.00 (+/−0.00) | 26.50 (+/−0.08) |

Figure 23:
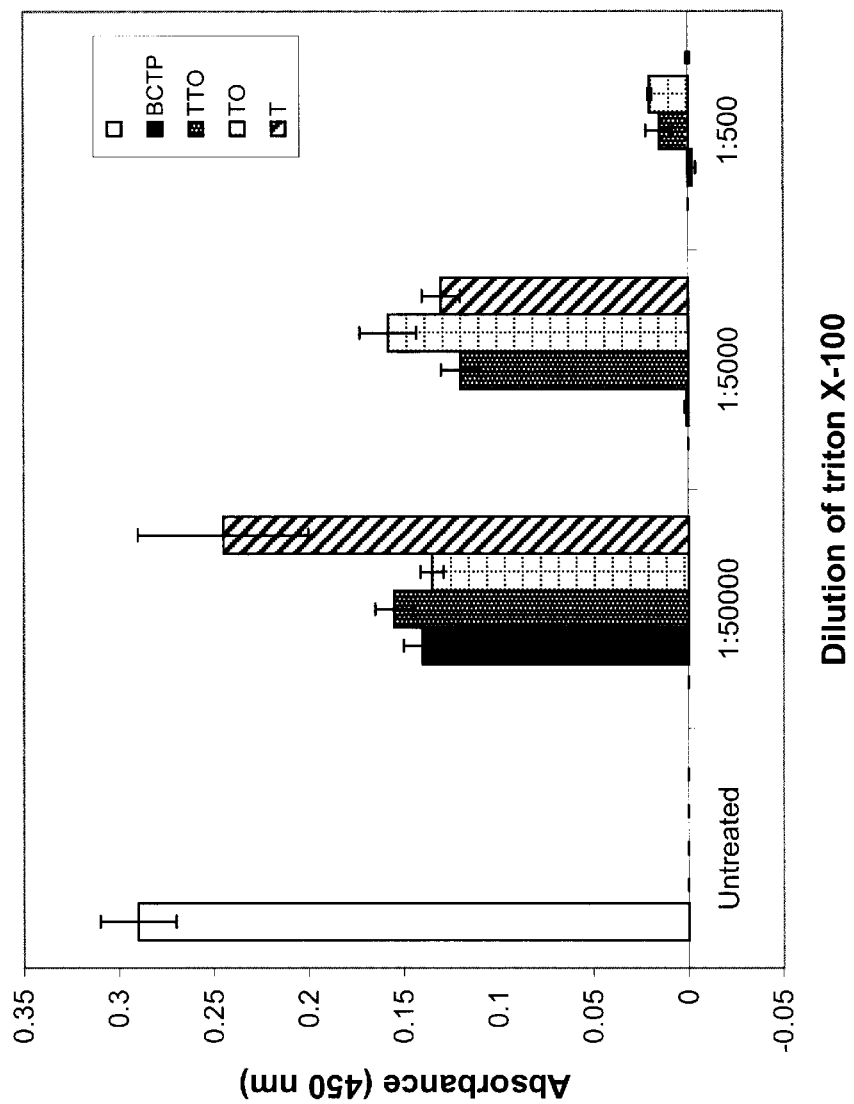
FIG. 23 illustrates the efficacy of BCTP as an anti-influenza agent as compared to Triton X-100. Influenza A virus was treated with BCTP, tri(n-butyl)phosphate/Triton X-100/soybean oil (TTO), Triton X-100/soybean oil (TO), and Triton X-100 (T) alone for 30 min. The concentration of Triton X-100 was the same in all preparations used for treatment. Inhibition of influenza A infection was measured using cellular ELISA. Each data point represents the mean of three replicates +/− one standard error.

Anti-influenza A efficacy of BCTP: Since Triton X-100 detergent has anti-viral activity (Maha and Igarashi, 1997; Portocala et al., 1976), it was investigated whether Triton X-100 alone or combined with individual BCTP components inhibits influenza A infectivity to the same extent as BCTP. Influenza A virus was treated with: 1) BCTP, 2) the combination of tri(n-butyl)phosphate, Triton X-100, and soybean oil (TTO), 3) Triton X-100 and soybean oil (TO), or 4) Triton X-100 (T) alone. BCTP was significantly more effective against influenza A virus at 1:10 and 1:100 dilutions (Triton X-100 dilution of 1:500, and 1:5000) than Triton X-100 alone or mixed with the other components tested (FIG. 23). At the dilution 1:1000, BCTP (Triton X-100 dilution of 1:50,000) was able to reduce influenza A infection of MDCK cells by approximately 50% while Triton X-100 alone at the same concentration was completely ineffective.

Figure 24:
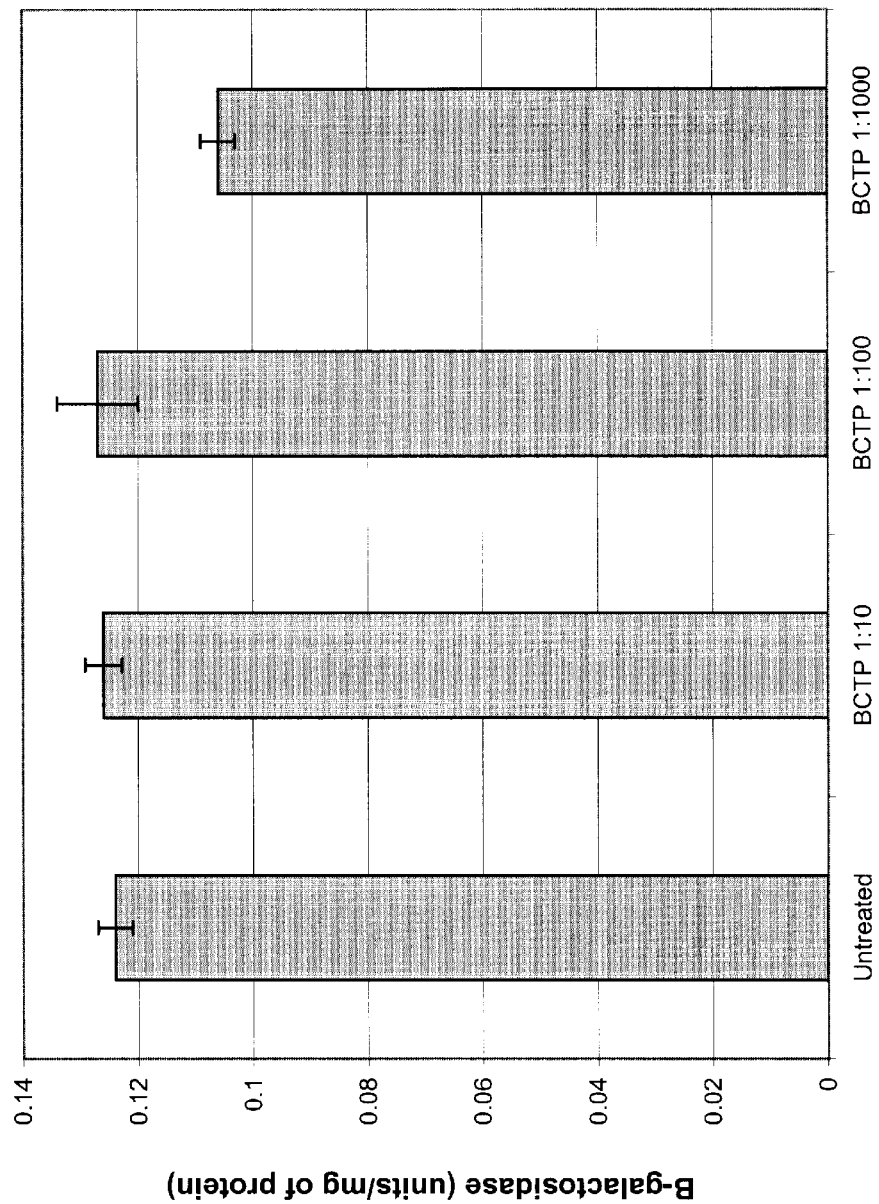
FIG. 24 shows that BCTP does not affect adenovirus infectivity. Adenoviral vector (AD.RSV ntlacZ) was treated with three dilutions of BCTP for 30 min. and subsequently used for transfection of 293 cells. Five days later the 6-galactosidase assay was performed. Each data point represents the mean of eight replicates +/− one standard error.

BCTP does not affect infectivity of non-enveloped virus: To investigate whether BCTP may affect the infectivity of non-enveloped virus, genetically engineered adenovirus containing LacZ gene was used, encoding β-galactosidase. This adenovirus construct was deficient in the transforming gene and therefore can replicate and transform only permissive cells containing the transforming gene of adenovirus 5. The 293 cells, which constitutively express transforming gene, were employed to promote adenovirus replication and production of β-galactosidase enzyme. As shown in FIG. 24, BCTP treatment did not affect the ability of adenovirus to replicate and express β-galactosidase activity in 293 cells. Both BCTP treated and untreated adenovirus produced approximately 0.11 units of β-galactosidase enzyme.

Figure 25:
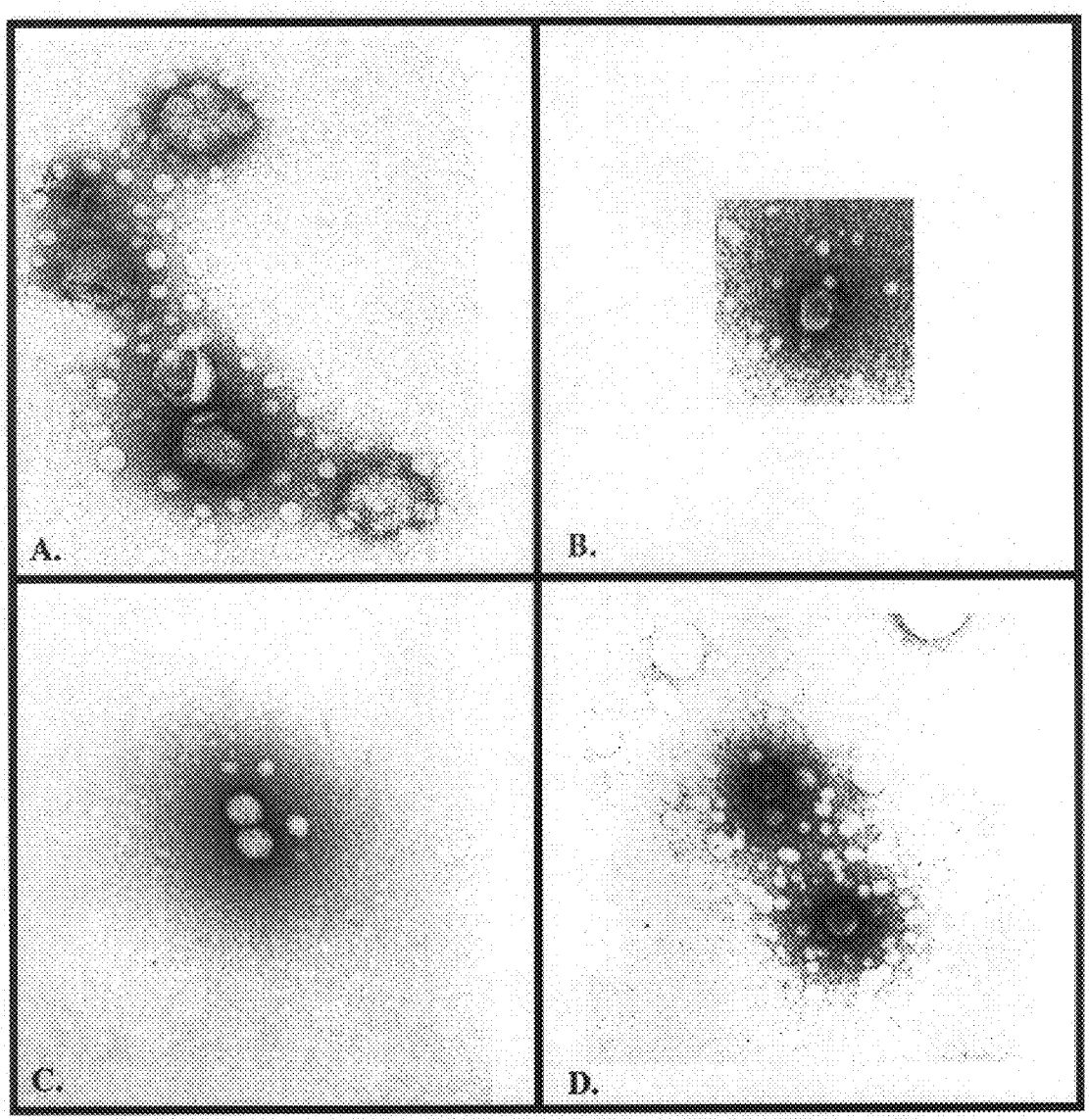
FIG. 25 illustrates the structures of influenza A and adenovirus viewed with electron microscopy. Viruses were either untreated or incubated with BCTP at 1:100 dilution for 15 and 60 min at room temperature and were subjected to electron microscopy fixation procedure as described in the Examples.

Action of BCTP on enveloped virus: Since BCTP only altered the infectivity of enveloped viruses, the action of this nanoemulsion on enveloped virus integrity was further investigated using electron microscopy. As shown in FIG. 25D, after a 60 min incubation with 1:100 dilution of BCTP, the structure of adenovirus is unchanged. A few recognizable influenza A virions were located after 15 min incubation with BCTP (FIG. 25B), however, no recognizable influenza A virions were found after 1 h incubation. BCTP's efficacy against influenza A virus and its minimal toxicity to mucous membranes demonstrates its potential as an effective disinfectant and agent for prevention of diseases resulting from infection with enveloped viruses.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in relevant fields are intended to be within the scope of the following claims.

REFERENCES

The following references, to the extent that they provide exemplary procedural or other details supplementary to those set forth herein, are specifically incorporated herein by reference.

Alasri et al., "Sporicidal properties of peracetic acid and hydrogen peroxide, alone and in combination, in comparison with chlorine and formaldehyde for ultrafiltration membrane disinfection." Can. J. Microbiol 1993; 39: 52–60.

Baragi et al., "Transplantation of transdiced Chondrocytes protects articular cartilage from intedeukin 1-induced extracellular matrix degradation." J Clin Invest 1995; 96: 2454–2460.

Barrett and Inglis "Growth purification and titration of influenza viruses." In: Mahy WJ. ed. Virology. a Practical approach. IRL. Press, 1985; 119–151.

Beauchamp et al., "A critical review of the toxicology of glutaraldphyde." Crit. Rev. ToxicoL 1992; 22:143–174.

Berkelman et al., "Emerging infectious diseases in the United States, 1993." J Infect Dis. 1994 Aug; 170(2):272–7. Review.

Burdon et al., "Experimental infection of mice with Bacillus cereus: studies of pathogenesis and pathologic changes." J. Infect. Dis. 1967; 117: 307–316.

Burdon and Wende. "On the differentiation of anthrax bacilli from Bacillus cereus." J. Infect. Dis. 1960; 107: 224–234.

Chatlyyne et al., "A lipid emulsion with effective virucidal activity against H IV-1 and other common viruses." Foundation for Retrovirology and Human Health, 3rd Conference on Retroviruses and Opportunistic Infections, Washington D.C., U.S.A., 1996; Abstract #351.

Dragon and Rennie "The ecology of anthrax spores: Tough but not invincible." Can. Vet. J. 1995; 36: 295–301.

Drobniewski "Bacillus cereus and related species." Clin. MicrobioL Rev. 1993; 6: 324–338.

Eriksson et al., "Virus validation of plasma-derived products produced by Pharmacia, with particular reference to immuno Globulins." Blood Coagulation and Fibtinolysis 1994; 5 (Suppl. 3): S37–S44.

Florence "Non-ionic surfactant vesicles: preparation and characterization." In:. Gregoriadis G. ed. Liposome Technology. Liposome Preparations and Related Techniques. 2nd ed. Vol. 1. CRC Press, 1993.

Foster and Johnstone "Pulling the trigger: the mechanism of bacterial spore germination." *MolecularMicrobiology* 1990;4:137–141.

Franz et al., "Clinical recognition and management of patients exposed to biological warfare agents." *JAMA* 1997;278: 399–411.

Fritz et al., "Pathology of experimental anthrax in the rhesus monkey." *Lab. Invest.* 1995; 73: 691–702.

Goodman & Gilman's "The Pharmacological Basis of Therapeutics" Eds. Hardman et al., 9th Edition, Pubi. McGraw Hill, 1996; chapters 43 through 50.

Graham et al., "Characteristics of a human cell line transformed by DNA from human adenovirus type 5." *J Gen Virol* 1977; 36: 59–74.

Halvorson and Church, Bacteriol Rev 1957, 21:112

Hamouda et al., "Microbiocidal effects of liposome-like microemulsions on pathogenic Gram negative bacteria." In: *American Society for Microbiology*, 98th General Meeting, Atlanta, Ga., U.S.A., 1998; Abstract A-52.

Hamouda et al., "A novel surfactant nanoemulsion with broad-spectrum sporicidal activity against Bacillus species". Journal Infectious Disease 1999. 180:1939–1949.

Hayden et al., "Plaque inhibition assay for drug susceptibility testing of influenza viruses." *Antimicrob Agents Chemother.* 1980 17: 865–870.

Herlocher et al., "Sequence comparison of AIAA/6/60 influenza viruses: mutations, which may contribute to attenuation." *Virus Res.* 1996; 42:11–25.

Hermonat et al., "The spermicide nonoxynol-9 does not inactivate papillomavirus." *Sexually Trans Dis* 1992; 19: 203–205.

Hess et al., "Epidermal toxicity of disinfectants." *Amer. J Dent.* 1991; 4: 51–56.

Hills, *J Gen Microbiol* 4:38,1950

Horowitz et al., "Solvent/detergent-treated plasma: a vi rus-in activated substitute for fresh frozen plasma." *Blood* 1992; 79: 826–831.

Huang et al., "Antiviral activity of some natural and synthetic sugar analogues." *FEBS Letters.* 1991; 291: 199–202.

Ivins et al., "Experimental anthrax vaccines: efficacy of adjuvants combined with protective antigen against an aerosol *Bacillus anthracis* spore challenge in guinea pigs." *Vaccine* 1995; 13: 1779–1784.

Jackson et al., "PCR analysis of tissue samples from the 1979 Sverdlovsk anthrax victims: The presence of multiple *Bacillus anthracis* strains in 10different victims." *PNAS* 1998; 95:1224–1229.

Karalvanova and Spiro RG. "Sulphation of N-linked oligosacchaddes of vesicular stomatitis and influenza virus envelope glycoproteins: host cell specificity, subcellular localization and identification of substituted saccharides." *Bioch J* 1998; 329: 511–518.

Lamanna and Jones "Lethality for mice of vegetative and spore forms of *Bacillus cereus* and Bacillus cereus-like insect pathogens injected intraperitoneally and subcutaneously." *J Bact.* 1963; 85: 532–535.

Lamb and Krug "Orthomyxoviride: The viruses and their replication." In: Fields BN. Knipe DM. Howley PM. eds. Fields Virology, 3rd ed., Philadelphia Pennsylvania, U.S.A., Lippincoft-Raven Publishers, 1996; 1353–1395.

Lee "Review: in vitro spermicidal tests." Contraception 1996; 54: 131–147.

Lim and Chae "A simple assay for DNA transfection by incubation of the cells in culture dishes with substrates for beta-galactosidase." *Biotechniques* 1989;7: 576–579.

Lineaweaver et al., "Topical antimicrobial toxicity." *Arch. Surg.* 1985;120: 267–270.

Maha and Igarashi "The effect of nonionic detergent on dengue and Japanese encephalitis virus antigens in antigen detection ELISA and IgM-capture ELISA." *Southeast Asian J Trop Med Pub Health* 1997; 28: 718–722.

Mammen et al., "Effective inhibitors of hemagglutination by influenza virus synthesized from polymers having active ester groups. Insight into mechanism of inhibition." *J. Med Chem* 1995; 38: 4179–4190.

Mendel et al., "Oral administration of a prodrug of the influenza virus neuraminidase inhibitor GS 4071 protects mice and ferrets against influenza infection." *Antimicrob Agents Chemother* 1998; 42: 640–646.

Meselson et al., "The Sverdlovsk anthrax outbreak of 1979." *Science* 1994; 266:1202–1208.

Mobley "Biological warfare in the twentieth century: lessons from the past, challenges for the future." *Military Med.* 1995; 160: 547–553.

Morgan "A brief review of formaldehyde carcinogenesis in relation to rat nasal pathology and human health risk assessment." *ToxicoL PathoL* 1997; 25: 291–307.

Mosmann J. Immun. *Methods* 1983, 65, 55–63 Mulder and Hers "Influenza." Wolter-Noordhoff Publishing, 1972.

O'Hagan "Recent advances in vaccine adjuvants for systemic and mucosal administration." *J Pharmacy Pharmacol* 1998; 50: 1–10.

Pile et al., "Anthrax as a potential biological weapon." *Arch. Intem. Med.* 1998; 158: 429–434.

Portocala et al., "Immunoelectrophoretic characterization of Sendai virus antigens." *Virologie* 1976; 27: 261–264.

Russell "Bacterial spores and chemical sporicidal agents." *Clin. Micro* 1990; 3: 99–119.

Schulze "Effects of glycolysation on the properties and functions of influenza virus hemagglutinin." *J Infect Dis* 1997; 176 (Suppl. 1): S24–28.

Shibata "Germination of inactivated spores of *Bacillus cereus* T. Effect of preincubation with L-alanine or inosine on the subsequent germination." *Japan. J. Microbiol.* 1976; 20: 529–535.

Smith et al., "Dihydropyrancarboxamides related to Zanamivir: a new series of inhibitors of influenza virus sialidases. 1. Discovery, synthesis biological activity, and structure-activity relationships of 4-guanidino and 4-amino-4H-pyran-6-carboxamides." *J. Med Chem* 1998; 41: 787–797.

Titball and Manchee "Factors affecting the germination of spores of *Bacillus anthracis*." *J. Appi. Bact.* 1987; 62: 269–273.

U.S. Pat. No. 4,895,452
U.S. Pat. No. 5,103,497
U.S. Pat. No. 5,510,104
U.S. Pat. No. 5,547,677
U.S. Pat. No. 5,549,901
U.S. Pat. No. 5,618,840
U. S. Patent 5,700,679
U.S. Pat. No. 5,547,677
U.S. Pat. No. 5,662,957

Waghom and Goa, "Zanamivir." *Drugs* 1998; 55: 721–725.

Welkos and Friedlander "Pathogenesis and genetic control of resistance to the Steme strain of *Bacillus anthracis*." *Microb. Path.* 1988; 4: 53–69.

Welkos et al., "Differences in susceptibility of inbred mice to *Bacillus anthracis*" *Infect. Immun.* 1986; 51: 795–800.

Yanagita, 1957, *Arch Mikrobiol* 26:329

Zeitlin et al., "Tests of vaginal microbicides in the mouse genital herpes model." *Contraception* 1997; 56: 329–335.

We claim:

1. A composition comprising a germination enhancer and an emulsion, said emulsion comprising:
   (i) an aqueous phase;
   (ii) an oil phase comprising an oil and ethanol; and
   (iii) a surfactant.

2. The composition of claim 1, wherein said germination enhancer is selected from the group consisting of a-amino acids, glucose, fructose, asparagine, sodium chloride, ammonium chloride, calcium chloride, and potassium chloride.

3. The composition of claim 1, wherein said surfactant comprises tyloxapol.

4. The composition of claim 1, wherein said oil is selected from the group consisting of soybean oil, avocado oil, squalene oil, olive oil, canola oil, corn oil, rapeseed oil, safflower oil, sunflower oil, fish oil, flavor oil, and water insoluble vitamins.

5. The composition of claim 1, wherein said surfactant is selected from the group consisting of nonionic and ionic surfactants.

6. The composition of claim 1, wherein said emulsion further comprises an organic phosphate-based solvent.

7. The composition of claim 6, wherein said organic phosphate-based solvent is selected from the group consisting of dialkyl phosphates and trialkyl phosphates.

8. The composition of claim 7, wherein said tialkyl phosphate comprises tri-n-butyl phosphate.

9. The composition of claim 1, further comprising an interaction enhancer.

10. The composition of claim 9, wherein said interaction enhancer comprises a chelating agent.

11. The composition of claim 10, wherein said chelating agent is selected from the group consisting of ethylenediaminetetraacetic acid and ethylenebis(oxyethylenenitrilo)tetraacetic acid.

12. The composition of claim 1, further comprising a cationic halogen containing compound.

13. The composition of claim 12, wherein said cationic halogen containing compound comprises a halide selected from the group consisting of chloride, fluoride, bromide, and iodide.

14. The composition of claim 12, wherein said cationic halogen containing compound is selected form the group consisting of cetylpyridinium halides, cetyltrimethylammonium halides, cetyldimethylethylammonium halides, cetyldimethylbenzylammonium halides, cetyltributylphosphonium halides, dodecyltrimethylammonium halides, and tetradecyltrimethylammonium halides.

15. A method of killing or neutralizing a microbial agent on or in a human subject, comprising contacting said subject with an antimicrobial amount of a composition comprising an emulsion, said emulsion comprising:

(i) an aqueous phase;

(ii) an oil phase comprising an oil and ethanol; and (iii) a surfactant.

16. The method of claim 15, wherein said microbial agent comprises a bacteria.

17. The method of claim 16, wherein said bacteria comprises a gram positive bacteria.

18. The method of claim 16, wherein said bacteria comprises a gram negative bacteria.

19. The method of claim 15, wherein said microbial agent comprises a bacterial spore.

20. The method of claim 15, wherein said microbial agent comprises a virus.

21. The method of claim 15, wherein said microbial agent comprises a fungus.

22. The method of claim 15, wherein said composition further comprises a germination enhancer.

23. The method of claim 22, wherein said germination enhancer is selected from the group-consisting of α-mino acids, glucose, fructose, asparagine, sodium chloride, ammonium chloride, calcium chloride, and potassium chloride.

24. The method of claim 15, wherein said surfactant comprises tyloxapol.

25. The method of claim 15, wherein said oil is selected from the group consisting of soybean oil, avocado oil, squalene oil, olive oil, canola oil, corn oil, rapeseed oil, safflower oil, sunflower oil, fish oil, flavor oil, and water insoluble vitamins.

26. The method of claim 15, wherein said strfactant is selected from the group consisting of nonionic and ionic surfactants.

27. The method of claim 15, wherein said emulsion further comprises an organic phosphate-based solvent.

28. The method of claim 27, wherein said organic phosphate-based solvent is selected from the group consisting of dialkyl phosphates and trialkyl phosphates.

29. The method of claim 28, wherein said trialkyl phosphate comprises tri-n-butyl phosphate.

30. The method of claim 15, further comprising an interaction enhancer.

31. The method of claim 30, wherein said interaction enhancer comprises a chelating agent.

32. The method of claim 31, wherein said chelating agent is selected from the group consisting of ethylenediaminetetraacetic acid and ethylenebis(oxyethyleneitrilo)tetraacetic acid.

33. The method of claim 15, further comprising a cationic halogen containing compound.

34. The method of claim 33, wherein said cationic halogen containing compound comprises a halide selected from the group consisting of chloride, fluoride, bromide, and iodide.

35. The method of claim 33, wherein said cationic halogen containing compound is selected form the group consisting of cetylpyridinium halides, cetyltrimethylammoniun halides, cetyldimethylethylammoniun halides, cetyldimethylbenzylammonium halides, cetyltributylphosphonium halides, dodecyltrinethylammonium halides, and tetradecyltrimethylammonium halides.

* * * * *